US010973686B2

(12) United States Patent
Gast et al.

(10) Patent No.: US 10,973,686 B2
(45) Date of Patent: Apr. 13, 2021

(54) TREATMENT AND PREVENTION OF RETINAL VASCULAR DISEASE BY PHOTOCOAGULATION

(71) Applicant: Indiana University Research and Technology Corporation, Indianapolis, IN (US)

(72) Inventors: Thomas J. Gast, Bloomington, IN (US); Xiao Fu, London (GB); James A. Glazier, Bloomington, IN (US)

(73) Assignee: The Trustees of Indiana University, Bloomington, IN (US)

( * ) Notice: Subject to any disclaimer, the term of this patent is extended or adjusted under 35 U.S.C. 154(b) by 265 days.

(21) Appl. No.: 16/071,353

(22) PCT Filed: Jan. 20, 2017

(86) PCT No.: PCT/US2017/014412
§ 371 (c)(1),
(2) Date: Jul. 19, 2018

(87) PCT Pub. No.: WO2017/127732
PCT Pub. Date: Jul. 27, 2017

(65) Prior Publication Data
US 2019/0192345 A1    Jun. 27, 2019

Related U.S. Application Data

(60) Provisional application No. 62/417,199, filed on Nov. 3, 2016, provisional application No. 62/416,641, filed
(Continued)

(51) Int. Cl.
*A61F 9/008*   (2006.01)
*A61B 34/10*   (2016.01)
(Continued)

(52) U.S. Cl.
CPC ...... *A61F 9/00821* (2013.01); *A61F 9/00802* (2013.01); *A61B 3/1241* (2013.01);
(Continued)

(58) Field of Classification Search
None
See application file for complete search history.

(56) References Cited

U.S. PATENT DOCUMENTS

2006/0100677 A1* 5/2006 Blumenkranz ......... A61F 9/008
607/89
2014/0228824 A1    8/2014 Yee
(Continued)

FOREIGN PATENT DOCUMENTS

| CN | 103997948 | 8/2014 |
|----|-----------|--------|
| CN | 105246426 | 1/2016 |

(Continued)

OTHER PUBLICATIONS

Godara et al., "Adaptive Optics Retinal Imaging: Emerging Clinical Applications," NIH Public Access, Optim Vis Sci., Dec. 2010, 87(12) : 930-941. (Year: 2010).*
(Continued)

*Primary Examiner* — Kennedy Schaetzle
(74) *Attorney, Agent, or Firm* — Faegre Drinker Biddle & Reath LLP

(57) ABSTRACT

This disclosure relates to methods for treatment or prevention of retinal vascular disease by photocoagulation. More specifically, this disclosure relates to an improved technique for the placement of retinal burns so as to prevent the development of hypoxia and progression of ischemia in retinal tissue, including the macula. The methods can also be employed to prevent potential ischemic tissue damage in
(Continued)

diabetic, pre-diabetic or other patients with ischemic retinal vascular disease, or those at risk of ischemic retinal vascular disease.

35 Claims, 24 Drawing Sheets

Related U.S. Application Data on Nov. 2, 2016, provisional application No. 62/415,240, filed on Oct. 31, 2016, provisional application No. 62/291,358, filed on Feb. 4, 2016, provisional application No. 62/281,707, filed on Jan. 21, 2016.

(51) Int. Cl.
  *A61B 3/12* (2006.01)
  *A61B 5/00* (2006.01)

(52) U.S. Cl.
  CPC ............. *A61B 5/0066* (2013.01); *A61B 34/10* (2016.02); *A61F 2009/00863* (2013.01); *A61F 2009/00878* (2013.01); *A61F 2009/00897* (2013.01)

(56) References Cited

U.S. PATENT DOCUMENTS

| | | |
|---|---|---|
| 2015/0228076 A1 | 8/2015 | Mouridsen |
| 2015/0265465 A1 | 9/2015 | Charles |
| 2017/0304119 A1 | 10/2017 | Yee |

FOREIGN PATENT DOCUMENTS

| | | |
|---|---|---|
| WO | WO 2001/056466 A2 | 8/2001 |
| WO | 2013059564 A1 | 4/2013 |

OTHER PUBLICATIONS

Paulus, Yannis, M. et al., "Proliferative and Nonproliferative Diabetic Retinopathy," American Academy of Ophthalmology, Oct. 22, 2013, available on the Internet at https://www.aao.org/current-insight/laser-treatment-of-proliferative-nonproliferative- ; 20 pages.

Yang, Sungwook, PhD, et al, "Handheld Automated Microsurgical Instrumentation for Intraocular Laser Surgery," Lasers in Surgery and Medicine, Oct. 2015, vol. 47, No. 8, available on the Internet at https://www.ncbi.nlm.nih.gov/pmc/articles/PMC4889221/pdf/nihms786257.pdf ; 24 pages.

Chalam, Kakarla, et al, "Evaluation of a Novel, Non Contact, Automated Focal Laser with Integrated (NAVILAS®) Fluorescein Angiography for Diabetic Macular Edema," Middle East African Journal of Ophthalmology, Jan.-Mar. 2012, vol. 19, No. 1, available on the Internet at https://www.ncbi.nlm.nih.gov/pmc/articles/PMC3277016/?report=printable ; 11 pages.

Stefansson, Einar, "The Mechanism of Retinal Photocoagulation—How Does the Laser Work," European Ophthalmic Review, Touch Briefings 2008, available on the Internet at http://www.touchopthalmology.com/sites/www.touchopthalmology.com/files/stefansson.pdf ; 4 pages.

Serlin, Yonatan, et al., "Novel Fluorescein Angiography-Based Computer-Aided Algorithm for Assessment of Retinal Vessel Permeability," PLOS One, Apr. 23, 2013, vol. 8, Issue 4, available on the Internet at http://journals.plos.org/plosone/article/file?id=10.1371/journal.pone.0061599&type=printable ; 7 pages.

Kent, Christopher, "Computer-Guided Laser Photocoagulation," Review of Opthalmology, Jan. 18, 2011, available on the Internet at https://www.reviewofophthalmology.com/article/computer-guided-laser-photocoagulation ; 5 pages.

International Search Report and Written Opinion issued by the ISA/US, Commissioner for Patents, dated May 3, 2017, for International Application No. PCT/US2017/014412; 9 pages.

Extended European Search Report issued by the European Patent Office, Munich, Germany, dated Aug. 5, 2019, or European Patent Application No. 17742049.4.

Fu et al., "Progression of Diabetic Capillary Occlusion: A Model", PLoS Computational Biology, DOI: 10.1371/journal.pcbi.1004932, Jun. 14, 2016.

\* cited by examiner

Model construction          AOSLO image $P_b^{art}$ - Arterial pressure ; $P_b^{ven}$ - Venous pressure
$P_{O_2}^{art}$ - Arterial oxygen tension ; $P_{O_2}^{faz}$ - FAZ oxygen tension

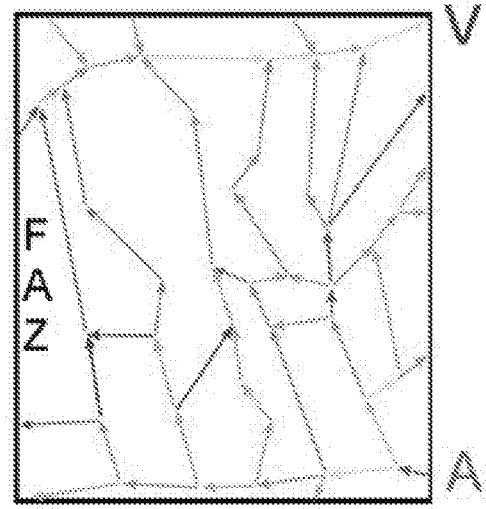
FIG. 18A week 0
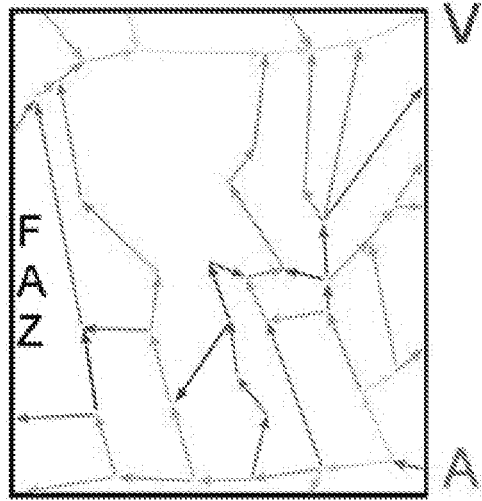
FIG. 18B week 72
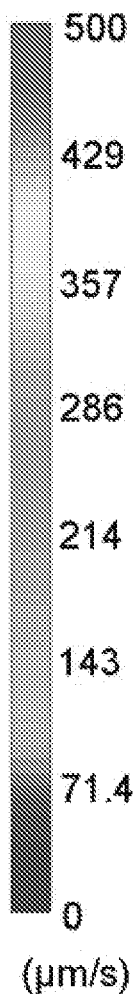
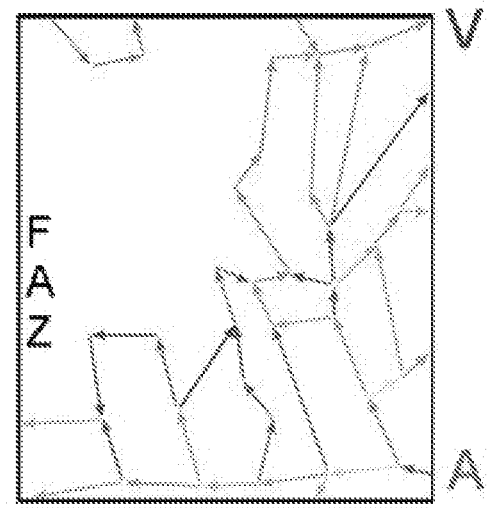
FIG. 18C week 124
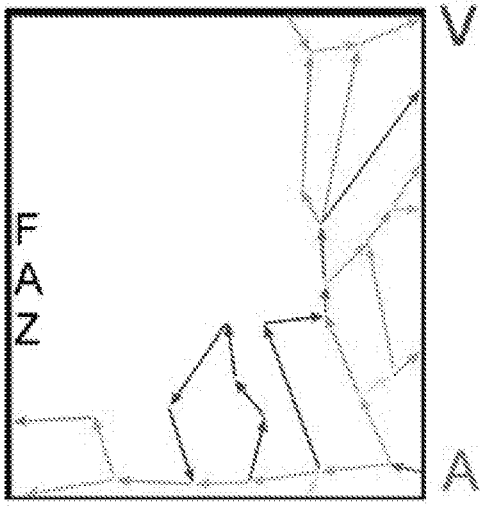
FIG. 18D week 152

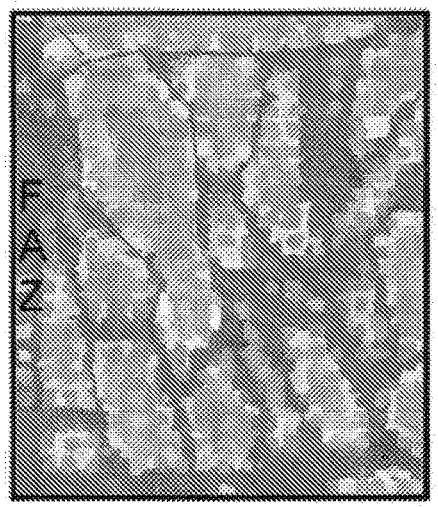
week 0
FIG. 19A
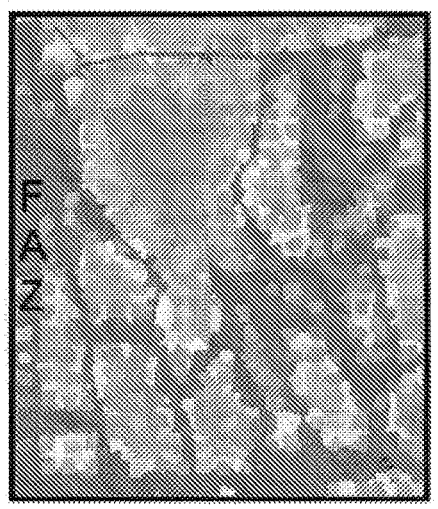
week 72
FIG. 19B
week 124
FIG. 19C
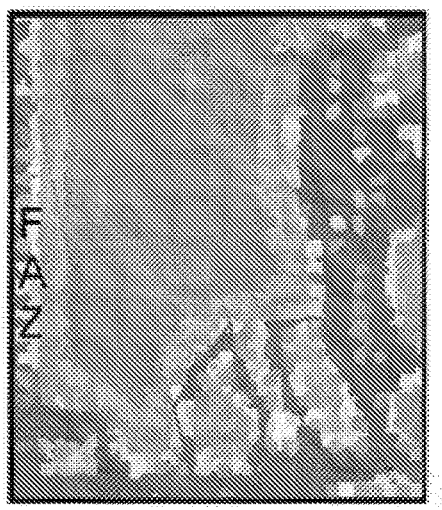
week 152
FIG. 19D
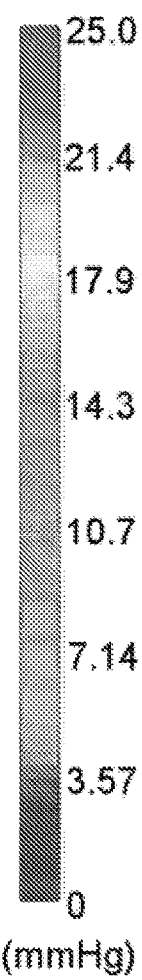
(mmHg)

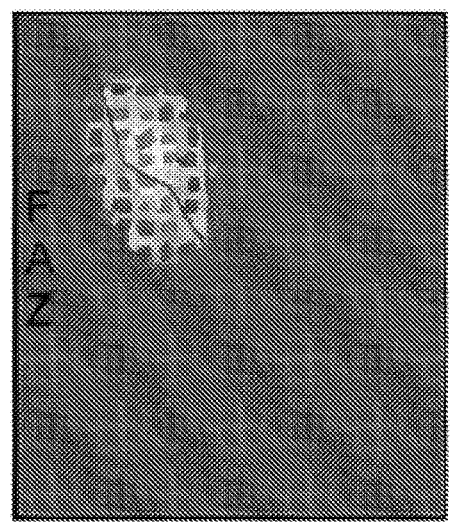
week 0
FIG. 20A
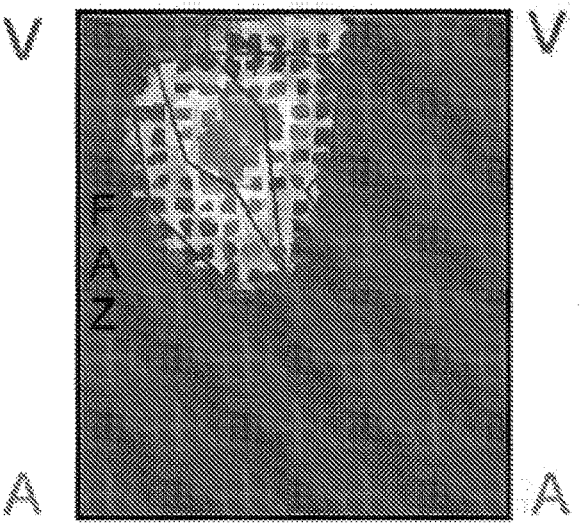
week 72
FIG. 20B
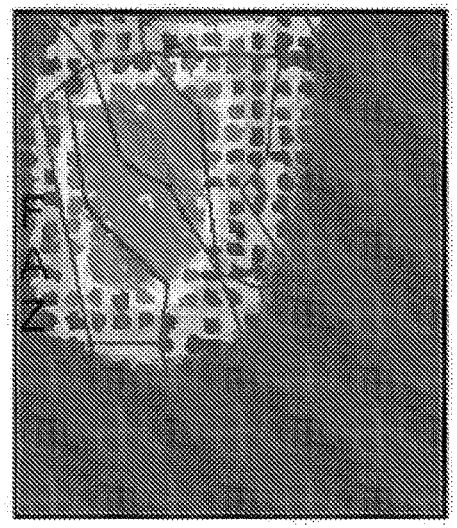
week 124
FIG. 20C
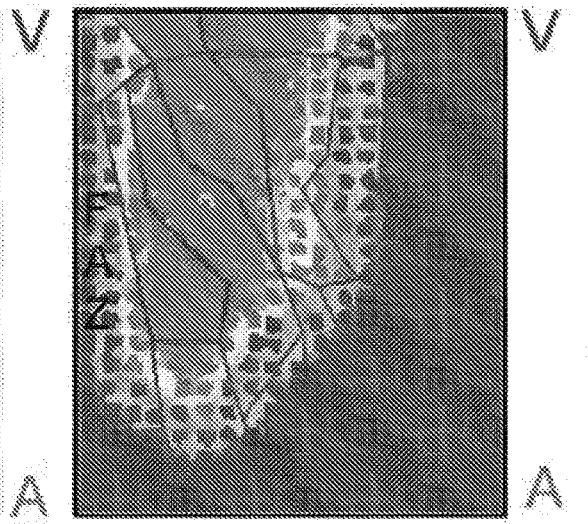
week 152
FIG. 20D
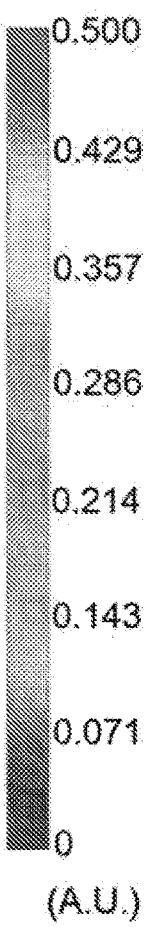
0.500
0.429
0.357
0.286
0.214
0.143
0.071
0
(A.U.)

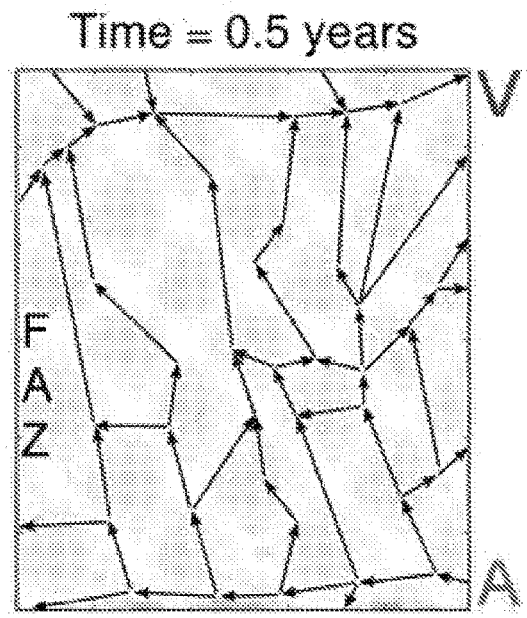
FIG. 21A
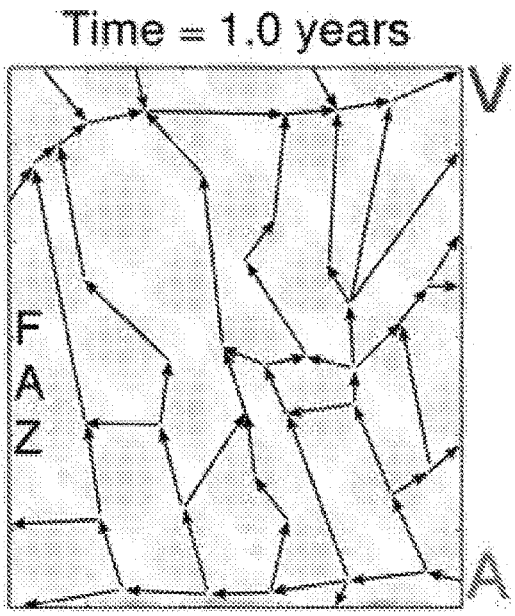
FIG. 21B
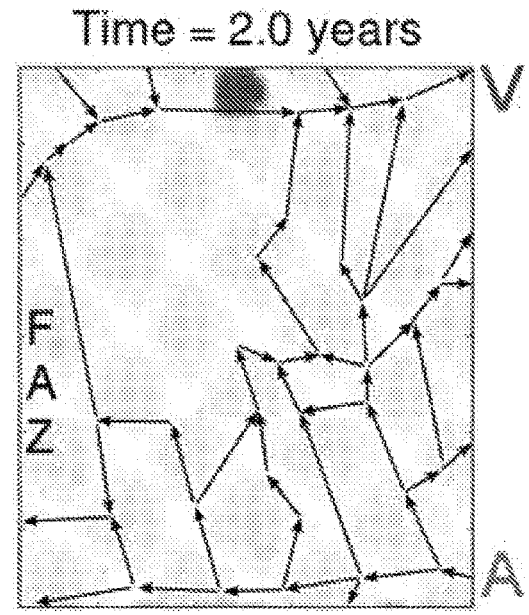
FIG. 21C
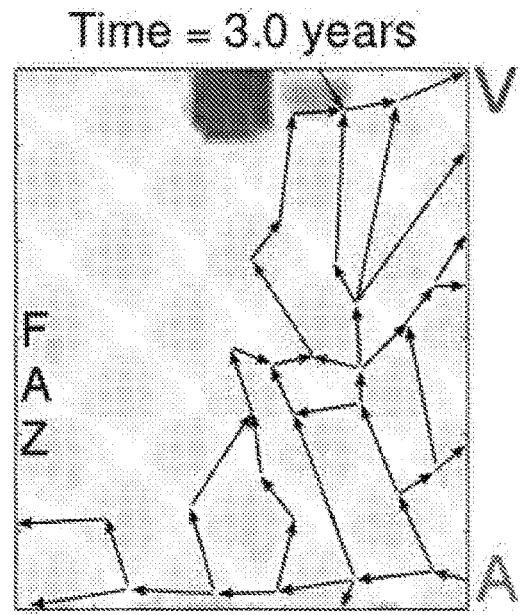
FIG. 21D
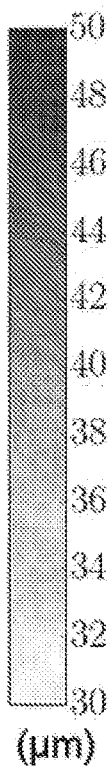

TREATMENT AND PREVENTION OF RETINAL VASCULAR DISEASE BY PHOTOCOAGULATION

CROSS-REFERENCE TO RELATED APPLICATIONS

This application is a U.S. National Stage under 35 U.S.C. § 371 of International Patent Application No. PCT/US2017/014412, filed Jan. 20, 2017, which claims the benefit of U.S. Provisional Application No. 62/417,199, filed Nov. 3, 2016, and U.S. Provisional Application No. 62/416,641, filed Nov. 2, 2016, and U.S. Provisional Application No. 62/415,240, filed Oct. 31, 2016, and U.S. Provisional Application No. 62/291,358, filed Feb. 4, 2016, and U.S. Provisional Application No. 62/281,707, filed Jan. 21, 2016, each of which is incorporated herein by reference in its entirety.

FIELD

This disclosure relates to methods for treatment or prevention of retinal vascular disease and/or macular edema. More specifically, this disclosure relates to improved techniques for the placement of retinal burns in both the retinal periphery and the macula so as to prevent the development of hypoxia in the macula and the propagation of ischemia by the occlusion of retinal vessels. The methods can also be employed to prevent potential ischemic tissue damage in diabetic, pre-diabetic or other patients with ischemic retinal vascular disease.

BACKGROUND

Retinal Vascular Disease

Retinal vascular disease is a significant and growing global problem. The most common form of retinal vascular disease is caused by diabetes mellitus. It is well-known that the incidence of diabetes is increasing at an alarming rate. Diabetic retinopathy is a significant problem in type I and type II diabetes. The hyperglycemia caused by diabetes leads to many complications, and diabetic retinopathy is the leading cause of impaired vision or blindness in people of working age in the United States.

Blood vessels, particularly the capillaries, in the diabetic eye are susceptible to occlusion, producing retinal hypoxia and altering synthesis of various factors and cytokines. These changes in cytokine and other factors can trigger an adverse local feedback cycle which increases the likelihood of occlusion of adjacent capillaries.

Current treatment for such diseases is primarily pan-retinal photocoagulation (PRP). The treatment relies on lasers to destroy photoreceptors in the retina, which are major oxygen consumers. Destruction of some of the eye's photoreceptors by PRP allows for oxygen to be available to lower levels of cytokines such as vascular endothelial growth factor (VEGF). This lowering tends to cause regression of neovascularization and lowers the risk of vision loss. Other methods for producing local damage to the photoreceptors are available and known, but laser treatment is the most common approach. This treatment is somewhat effective in preventing further damage to the retina due to the complications of retinal neovascularization, but can also cause complications such as the loss of peripheral vision and increased macular edema. Generally, this treatment is done by randomly scattering large laser burns in the peripheral retinal or with a grid of laser burns applied to areas of the macula that appear to have leaking vessels.

The complications of diabetes in the eye are largely related to physiological disturbances of the capillaries in the form of confluent capillary occlusion with resultant areas of retinal ischemia leading to elevated production of VEGF and other biological factors. The elevated VEGF leads to increased rates of capillary occlusion in nearby capillaries by elevating local capillary adhesion proteins and to vascular leakage resulting in retinal edema, and if sufficient areas of retina are involved, to neovascularization.

The fundamental pathological process resulting in individual capillary occlusion is believed to be the result of an activated leukocyte adhering to and damaging the retinal capillary endothelial cell ultimately resulting in occlusion of a single capillary, presumably after cycles of damage exhaust endothelial replication. Yet what is observed clinically are large confluent areas of retinal ischemia rather than random capillary occlusions. Therefore, occlusion of an individual capillary is likely dependent on the patency or occlusion of surrounding capillaries. That is, there is non-random occlusion such that occlusion begets further occlusion in the form of an adverse feedback cycle. With capillary occlusion, local retinal tissue becomes ischemic/hypoxic and that tissue releases a factor or factors which increase the likelihood of nearby capillary occlusion.

Macular Edema

Macular edema is the build-up of fluid in the macula, often occurring with diabetic retinopathy, which is the leading cause of moderate visual loss in the working age population in the United States. Macular edema occurs when there is abnormal leakage and accumulation of fluid in the macula from leaking retinal blood vessels, and often presents in the context of diabetic retinopathy. It is well-known that the incidence of diabetes is increasing at an alarming rate. Diabetic retinopathy is a significant problem in type I and type II diabetes. The hyperglycemia caused by diabetes leads to many complications.

Macular edema can also occur following eye surgery, in association with age-related macular degeneration, or as a consequence of inflammatory diseases that affect the eye.

Currently, about 40% of patients with diabetic macular edema receive laser treatment as an adjunct to treatment with intra-ocularly injected anti-vascular endothelial growth factor (VEGF) agents. Lowering VEGF levels tends to reduce vessel leakage and lowers the risk of vision loss. The current laser treatments for macular edema are often in the form of a grid of laser burns, and are largely applied without any guiding rationale.

SUMMARY

Described herein are methods for treating or preventing retinal vascular disease, including macular edema, by photocoagulation. The methods can also be used to prevent potential ischemic tissue damage in diabetic, pre-diabetic, or other patients with ischemic retinal vascular disease. In certain embodiments described herein, the methods can be used for treating ischemic retinal vascular disease, or can prevent or minimize the onset or progression of retinal ischemia in a subject. In some embodiments, the method includes generating on a retina of the subject a pattern of small photocoagulation burns having a spacing sufficiently dense to maintain oxygenation of retinal tissue within a boundary of the pattern of photocoagulation burns. In some embodiments, the spacing of the photocoagulation burns yields gaps of about 140 microns or less between at least one of: (a) a pair of individual photocoagulation burns of the pattern of photocoagulation burns; and (b) an individual photocoagulation burn of the pattern of photocoagulation burns and an arteriole or venule. In other embodiments, the spacing of the photocoagulation burns yields individual photocoagulation burns of the pattern of photocoagulation burns being no farther from another photocoagulation burn, an arteriole, or a venule than about 140 microns. In other embodiments, described herein is an improved technique for the placement of macular burns so as to prevent the development of hypoxia and propagation of ischemia in macular tissue.

In certain embodiments, individual photocoagulation burns of the pattern of photocoagulation burns have a band shape having a length of about 50 microns to about 300 microns and a width of about 20 microns to about 100 microns, wherein the length of the band shape is greater than the width. In other embodiments, individual photocoagulation burns of the pattern of photocoagulation burns have a band shape having dimensions of length of about 300 microns and width of about 100 microns, or length of about 52 microns and a width of about 20 microns. In some embodiments, the individual photocoagulation burns of the pattern of photocoagulation burns are positioned approximately centrally between an arteriole and a venule of the retina.

In other embodiments, individual photocoagulate burns of the pattern of photocoagulation burns are rounded and have diameters of about 20 microns to about 100 microns. In certain embodiments, individual photocoagulate burns of the pattern of photocoagulation burns are rounded and have diameters of about 60 microns or of about 80 microns. In some embodiments, the individual photocoagulation burns of the pattern of photocoagulation burns are positioned approximately centrally between an arteriole and a venule of the retina or are positioned approximately adjacent to an arteriole or a venule.

In some embodiments, the retinal vascular disease to be treated or prevented is diabetic retinopathy. In certain embodiments, subjects at risk of developing diabetic retinopathy can be treated using a method described by the present disclosure, thereby preventing the onset of diabetic retinopathy.

In certain embodiments, the retinal tissue on which the pattern of photocoagulation burns is generated is ischemic retinal tissue, is non-ischemic retinal tissue, or is a combination of ischemic and non-ischemic retinal tissue. In other embodiments, the retinal tissue on which the pattern of photocoagulation burns is generated is non-ischemic retinal tissue and the subject is at risk of developing a retinal vascular disease. In yet other embodiments, the methods are performed on a subject that has a retinal vascular disease.

In some embodiments, the pattern of photocoagulation burns is created by a laser. In certain embodiments, the generation of the pattern of photocoagulation burns is under manual control. In other embodiments, the generation of the pattern of photocoagulation burns is automated or computer guided with medical supervision.

In other embodiments, an angiogram is performed prior to generating the pattern of photocoagulation burns. In some embodiments, the angiogram is used as a reference to position the pattern of photocoagulation burns on the retina.

In certain embodiments, the method for treating or preventing macular edema, or treating or preventing progression of retinal ischemia in a subject includes applying one or more photocoagulation burns to one or more areas of the macula predicted to cause progression of ischemia following occlusion of a capillary or capillary segment at or near the one or more areas.

In some embodiments, the one or more areas of the macula predicted to cause progression of ischemia following occlusion of a capillary or capillary segment at or near the one or more areas are identified by modelling the subject's macular capillary anatomy, generating a risk map for each capillary or capillary segment, and selecting one or more capillaries or capillary segments predicted by the risk maps to cause progression of ischemia if occluded. The one or more capillaries or capillary segments may be selected when a risk map for a capillary or capillary segment indicates a frequency of occlusion of surrounding capillaries of about 0.2 or greater following simulation.

In other embodiments, methods include identifying one or more areas of a subject's macula predicted to cause progression of ischemia following occlusion of a capillary or capillary segment at or near the one or more areas. The method includes determining a distance from each capillary or capillary segment of the subject's macular capillary anatomy to the next nearest capillary or capillary segment, and selecting one or more macular areas or individual capillaries or capillary segments that may benefit from additional modelling predicting capillary occlusion.

In some embodiments, the method includes determining the subject's macular capillary anatomy. The subject's macular capillary anatomy may be determined by, for example, angiography, adaptive optics scanning laser ophthalmoscopy, or optical coherence tomography-angiography or other future imaging technologies.

In certain embodiments, the one or more photocoagulation burns have a diameter of about 20 microns to about 100 micron. In other embodiments, the one or more photocoagulation burns have a diameter of about 50. Photocoagulation burns may be produced by a laser that can be manually applied, computer guided, or fully automated.

Embodiments of the present disclosure also provide a system configured to carry out a method described herein. In certain embodiments, the system includes a processor and a memory comprising one or more computer-readable media having computer-executable instructions embodied thereof. When executed by a processor, the computer executable instructions can cause the processor to identify one or more areas of the macula predicted to cause progression of ischemia following occlusion of a capillary or capillary segment at or near the one or more areas. The processor may be configured to receive an input of the subject's macular capillary anatomy.

BRIEF DESCRIPTION OF THE DRAWINGS

The accompanying drawings are incorporated into and form a part of the specification to illustrate several examples of the present disclosure. The drawings simply illustrate examples of how the disclosure can be made and used and are not to be construed as limiting the disclosure to the illustrated and described examples. Further features and advantages will become apparent from the following, more detailed, description of the various aspects, embodiments, and configurations of the disclosure, as illustrated by the drawings referenced below.

FIGS. 18A-18D depict flow velocity patterns following an initial capillary occlusion for modeled CASE 1 at week 0 (FIG. 18A), week 72 (FIG. 18B), week 124 (FIG. 18C), and week 152 (FIG. 18D).

FIGS. 19A-19D depict oxygen tension patterns following an initial capillary occlusion for modeled CASE 1 at week 0 (FIG. 19A), week 72 (FIG. 19B), week 124 (FIG. 19C), and week 152 (FIG. 19D).

FIGS. 20A-20D depict VEGF level patterns following an initial capillary occlusion for modeled CASE 1 at week 0 (FIG. 20A), week 72 (FIG. 20B), week 124 (FIG. 20C), and week 152 (FIG. 20D).

FIGS. 21A-21D depict retinal thickness over time for modeled CASE 1 at the end of year 0.5 (FIG. 21A), year 1 (FIG. 21B), year 2 (FIG. 21C), and year 3 (FIG. 21D).

DETAILED DESCRIPTION

Figure 1A:
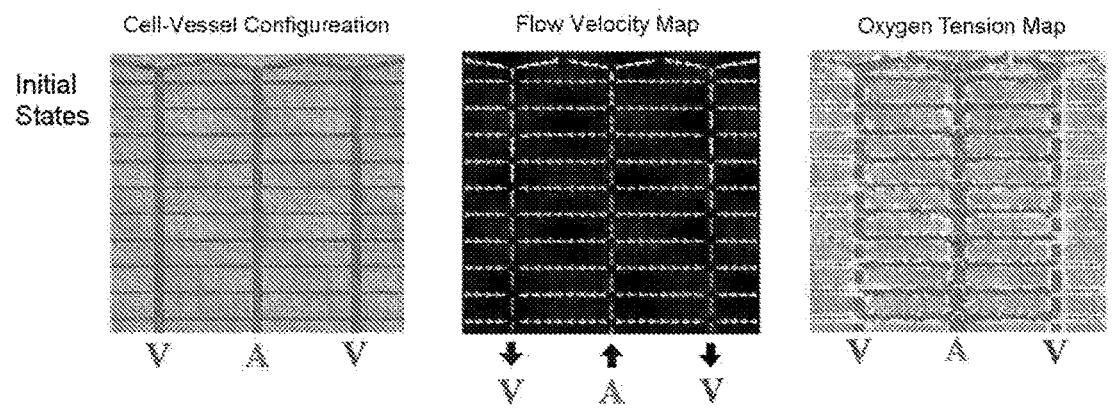
FIG. 1A depicts a 2D view of the configuration of the retinal capillary network, Mueller cells, and other retinal cells in the in silico peripheral retina. The center panel depicts a flow velocity map of the model vascular network. The right panel depicts an oxygen tension map of the modeled section.

Patterned Photocoagulation for the Treatment and Prevention of Retinal Vascular Disease Certain aspects involve production of retinal photocoagulation burns placed with sufficiently close spacing capable of preventing the spread of existing or potential areas of retinal ischemia in diabetic retinopathy or other retinal vascular disease. In certain embodiments, a grid of very small burns to ischemic or non-ischemic retina can be produced by a laser. The grid of small burns may be used to treat existing retinal ischemia and/or to prevent propagation of capillary occlusion. Without wishing to be limited by any particular theory, treatment of existing retinal ischemia or prevention of propagation of capillary occlusion may be a result of improved oxygenation of the burned retina, thereby preventing ischemic-driven elevation of VEGF, which itself may act to drive propagation of capillary occlusion.

The terms "photocoagulation," "photocoagulation burn," and "burn" refer to destruction of the photoreceptor retinal layer of some form. Photocoagulation can be achieved using various lasers, and may cause the destruction of retinal photoreceptors to eliminate them as oxygen consumers, with minimal destruction of either the overlying retinal tissue or of deeper choroidal vascular tissue. These same areas then allow for the diffusion of oxygen from the underlying choroid, which then acts as an oxygen source to the retina.

To accomplish photocoagulation, low-power laser delivery within a short time period can be performed to minimize the spread of energy absorbed in the deep retinal layers, which include the photoreceptor layer and/or retinal pigment epithelium, to more superficial overlying retinal tissue. The overlying retinal tissue contains intermediary retinal neurons, the retinal ganglion cells, glia, the nerve fiber layer and retinal vasculature. Visual field defects may be avoided or minimized by preserving or at least minimizing damage to the overlying retinal tissue. Destruction of the highly oxygen consumptive photoreceptor layer improves oxygenation of the overlying retinal layers and adjacent retinal tissues via diffusion of oxygen from the choroidal vasculature. This improved oxygenation can either prevent the occurrence of hypoxia in overlying retinal tissues or reverse existing retinal hypoxia. Ischemic retinal tissue can produce various factors including VEGF which can have adverse consequences to the functioning of ocular tissue by several mechanisms. Locally elevated VEGF can prompt capillary closure as well as vascular leakage producing retinal edema. Elevated VEGF levels also are fundamental to the development of the most serious ocular diabetic complications, retinal and iris neovascularization.

Individual photocoagulation burns result in the creation of a region of oxygenation. Photocoagulation burns can be produced by lasers to produce light, minimally destructive, or subthreshold burns. The width of a burn can be determined by the width of a photocoagulated area. Laser burns may be rounded (a "dot"), or may be linear or approximately linear, and in some embodiments, may be formed as a continuous burn via plurality of overlapping rounded burns. A linear or approximately linear burn may be an extended burn (a "line"), or relatively short (a "band"). Where a plurality of overlapping rounded burns form a continuous linear or approximately linear burn (e.g., a band), the resulting linear or approximately linear burn is referred to as an "individual" burn. That is, "individual" does not refer to each of the rounded burns of the plurality of overlapping rounded burns, but rather to the resulting band. It is noted that closely spaced but not necessarily contiguous overlapping individual photocoagulation burns can have gaps between two individual burns small enough so that the intervening retina is oxygenated. The term 'grid' refers to individual photocoagulation burns fairly regularly spaced in two dimensions, with the distances between burns of small enough distance that the intervening retina is oxygenated to a level that prevents induction of elevated synthesis of VEGF and other factors produced by retinal hypoxia, and prevents progression of ischemia.

In certain cases, photocoagulation burns are produced to act as barriers of oxygenated retina which block the spread of progressive capillary closure caused by local VEGF or other pro-ischemic factor production in ischemic retina. In some embodiments, photocoagulation burns are created at the border of an existing patch of ischemic retina or act to partition an area of non-ischemic retina into smaller areas. In other embodiments, a grid of photocoagulation burns may be produced on retinal areas with intact capillaries, where the grid may prevent the propagation of capillary closure. In certain embodiments, photocoagulation burns may be produced in the peripheral retina. In peripheral use, the burns may preserve peripheral retinal function and by lessening the development of peripheral ischemia, lower ocular vitreal VEGF levels, and in some cases reduce or prevent macular edema. This may reduce progression of non-local capillary occlusion. In other embodiments, photocoagulation burns may be produced in the posterior pole of the eye, preventing progressive capillary closure.

In some embodiments, the procedure of producing photocoagulation burns, including grids, may be automated. While it would be possible to create a photocoagulation burn pattern with sufficiently closely spaced burns, including a grid pattern manually, it would be time intensive. The procedure may be automated through a computerized imaging/laser delivery system. In certain embodiments, the computerized imaging/laser delivery system may be registered to a fundus image and then applied in a computer assisted but physician-guided fashion. Currently, panretinal photocoagulation is performed if neovascularization of the optic disk or neovascularization elsewhere is discovered. Burns are placed in the retina between large retinal vessels generally without fluorescein angiography imaging guidance as to whether a given region of retina is ischemic or not, rather than being placed with the benefit of a wide field angiogram identifying all areas of ischemic and non-ischemic retina to ensure minimal destruction of non-ischemic retina. Embodiments of the present disclosure place light, minimally destructive, or subthreshold burns in a barrier or a grid fashion on the retina. In some embodiments, burns may be produced only in retina with patent capillaries. However, in certain embodiments angiography may not be required because the burns of the present embodiments would be therapeutic to ischemic retina and the creation of barriers and/or grids would accomplish the technique's goal of preventing progression of ischemia/hypoxia in still vascularized retina even if done without reference to an angiogram.

Figure 7:
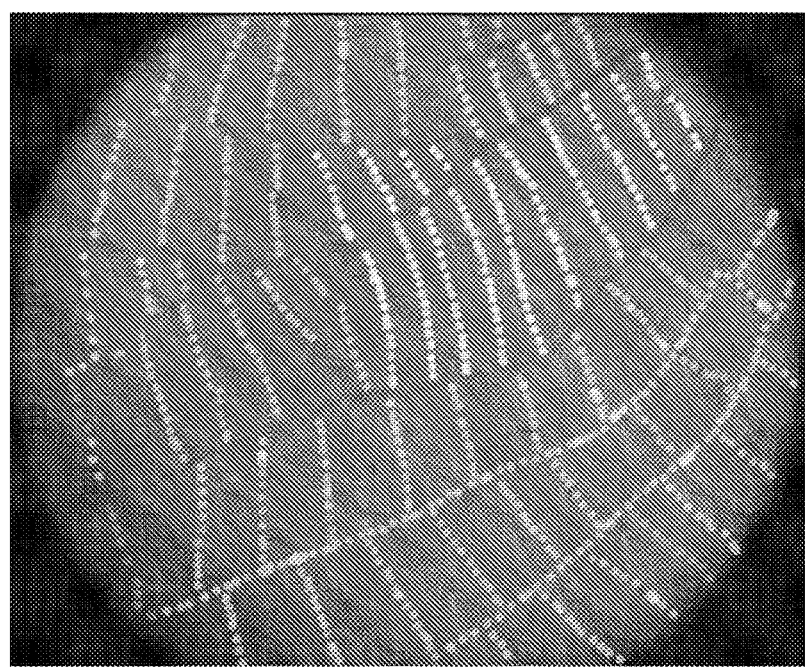
FIG. 7 is a computer-rendered representation of retinal burn patterns according to an embodiment described herein.

Embodiments described in the present disclosure provide methods of treatment of progressive ischemic retinal vascular disease. In some embodiments, methods include partitioning areas of non-ischemic retinal tissue from areas of ischemic retinal tissue by a border of photocoagulation burns producing an oxygenated retinal barrier. In other embodiments, partitioning occurs by the creation of subdivisions within the non-ischemic retina via a pattern of linear photocoagulation burns, thereby creating oxygenated retinal barriers. In other embodiments, the methods include producing a grid of photocoagulation burns on areas of non-ischemic retinal tissue, ischemic retinal tissue, or both non-ischemic and ischemic retinal tissue (see, e.g., FIG. 7). Certain embodiments provide a method for treating ischemic retinal vascular diseases, where the method can include performing an angiogram of a retina. The angiogram may assist in identifying vascularized and ischemic retinal tissue and may assist in the placement of the described photocoagulation burns or pattern (e.g., a grid) of burns. The angiogram may be a wide-field angiogram.

In certain embodiments, the methods may be applied in a preventive fashion by creating a pattern of burns, such as grid. The pattern of closely spaced photocoagulation burns can prevent propagation of ischemia early in the course of the disease, thereby preventing most of the retinal complications of diabetes or other ischemic vascular disease. In comparison to the present methods, existing pan-retinal photocoagulation (PRP) methods treat large areas of ischemic retina utilizing a large spot size laser with the goal of increasing oxygenation of overlying and immediately adjacent retina by lowering oxygen consumption via the local destruction of highly oxygen consuming photoreceptors. The standard PRP procedure creates large, circular, randomly scattered peripheral retinal burns or rectilinear grid patterns of large, circular burns without regard to the ischemia or non-ischemia of the treated retina. PRP is performed with a goal of achieving the net effect of the destruction of a certain more or less standard total amount of peripheral retina. The standard PRP procedure involves creation of 1200-1600 spots of 250-500 microns in size, delivered to the peripheral retina, usually over 2 treatment sessions. The deficiency of standard PRP is that the oxygen sources created by treatment are, because of the standard spacing of the large burns, too far from intervening retina to relieve its existing or potential hypoxia and therefor unable to prevent progressive capillary occlusion in areas of still non-ischemic retina. More recently, modifications have been introduced by the use of the multispot patterned scanning laser (PASCAL), which generally uses a rectangular grid pattern of circular burns. With few exceptions where wide field angiography is employed, traditional PRP and PASCAL generate burns to the entire peripheral retina, i.e., a retinal area is treated regardless of whether that area is ischemic. Both traditional PRP and PASCAL result in the destruction of a large area of otherwise healthy retinal tissue, with the large burns damaging photoreceptors and causing visual field loss. In comparison, the present methods may cause minimal damage to the retina, and can be used to treat and/or prevent ischemic retinal vascular disease, such as diabetic neovascularization, with limited or no visual field defects. In certain embodiments, the present methods can prevent progressive loss of capillaries in those areas not already ischemic, and can prevent visual complications of diabetic retinopathy. In some embodiments, the methods provided can be completed in a single office visit.

The instant photocoagulation burns, patterns, and methods are based on a mathematical model of the spread of ischemic retinopathy (see, e.g., Examples 1-5 and Materials and Methods). The model is described in the Material and Methods section, and in Fu et al., PLoS Comput Biol (2016) June 14; 12(6):e1004932, which is hereby incorporated by reference in its entirety for all purposes. According to the model, local areas of capillary loss spread via a mechanism dependent on progressive capillary closure secondary to elevated local factors such as VEGF. This spreading phenomenon results in extensive areas of capillary loss, that is, extensive contiguous areas of ischemic retina generally localized between and bounded by intact larger retinal blood vessels. Without wishing to be limited by any particular theory, it is thought that the retinal vessels act as barriers to the spread of ischemia because the retina around the vessels remains well oxygenated even when local capillaries are occluded and therefor there is no local VEGF production. Certain methods create, through a grid of small closely spaced burns, areas of retina that remains oxygenated (i.e., is not hypoxic) even if random capillary closure occurs. Propagation of capillary closure and resulting hypoxia is therefore inhibited. In other embodiments, photocoagulation lines are created to act as oxygenated retinal barriers, partitioning retinal tissue into smaller areas with lower ischemic/hypoxia propagation risks, and/or producing borders on ischemic areas, preventing the spread of ischemia into non-ischemic retina. Traditional PRP burns do not oxygenate local retina except the retina overlying and very near to the burn because of the distance between the burns, and therefore will not prevent progression of retinal ischemia in those retinal areas with still patent capillaries. Further, traditional PRP does not relieve local hypoxia due to individual capillary closure because the individual burn and the spacing of the burns are both large relative to the scale of the capillary network. Traditional PRP was designed to treat existing proliferative diabetic retinopathy. It is expected that destruction of the same area of ischemic retina with the present methods and photocoagulation lines would treat proliferative disease but would have the added function of slowing or preventing progressive capillary drop out when applied to non-ischemic retina. By doing so, it may better preserve peripheral vision and by lowering global VEGF production through preservation of functional retina, may lessen or prevent macular edema in those patients without a local macular etiology for that edema. Such a procedure done early in the development of diabetic retinopathy may largely prevent progressive capillary loss in the retinal periphery and also lower the rate of macular edema, as to a degree, it is a consequence of elevated vitreal VEGF levels. However, the methodologies disclosed herein do not require the cause of the adverse feedback cycle to be due to VEGF or that the cycle is stimulated by a particular cell type.

The photocoagulation burns, burn patterns, and methods of the present invention may also be used to treat or prevent other forms of retinal vascular disease.

In certain embodiments, the photocoagulation burns can be arranged in a grid pattern having sufficiently close spacing between individual photocoagulation burns so that the intervening retina can maintain oxygenation at a level that prevents induction of elevated synthesis of VEGF and other factors produced by retinal hypoxia, and can prevent progression of ischemia. In such embodiments, the area of oxygenation surrounding an individual burn overlaps with, or is sufficiently close to an area of oxygenation of, at least one other band or of an arteriole or venule to prevent propagation of ischemia between a pair of bands or between a band and an arteriole or venule. In certain embodiments, individual burns are spaced so that the edges of each individual burn are less than about 140 microns from the edges of another individual burn, an arteriole, or a venule (see, e.g., Example 4). Individual burns may be of any size. In some embodiments, burn size may be selected to minimize visual field defects while maintaining a spacing of about 140 microns between the edges of individual burns. In some embodiments, photocoagulation burns of the grid pattern may be approximately-band shaped, or rounded.

In certain embodiments, the photocoagulation burns can be approximately band-shaped, having a length (L) of about 50 microns to about 300 microns and a width (W) of about 20 microns to about 100 microns. Bands having any combination of a length and a width within these ranges are contemplated. Selection of band length and width can be made to balance the total burn area of the retina with the desired outcome, i.e., treatment or prevention of ischemia. In certain embodiments, band size can be selected to provide the minimal total burn area of the retina capable of preventing progression capillary occlusion and ischemia. In some embodiments, the bands can have a length of about 300 microns and a width of about 100 microns. In other embodiments, the bands can have a length of about 52 microns and a width of about 20 microns. In some embodiments, multiple bands of photocoagulation burns can be approximately regularly spaced in two dimensions, forming a grid pattern of bands. The grid pattern of bands can partition the retina into areas where if one becomes ischemic, adjacent areas are protected from ischemic propagation. The dimensions and spacing of the bands of a grid can be selected so that the edges of each band are less than about 140 microns from the edges of another band, or an arteriole or venule (see, e.g., Example 4). The dimensions and spacing of the bands of a grid can be further selected to minimize visual field defects. In some embodiments, a grid of bands can be created on retinal tissue without concern of the retinal vasculature (e.g., arterioles and venules). In other embodiments, bands may be positioned approximately centrally between an arteriole and a venule (see, e.g., Example 4).

In other embodiments, the photocoagulation burns can be approximately round (i.e., dots) having a diameter, or size (S), of about 20 microns to about 100 microns. Selection of dot size can be made to balance the total burn area of the retina with the desired outcome, i.e., treatment or prevention of ischemia/hypoxia. In certain embodiments, dot size can be selected to provide the minimal total burn area of the retina capable of preventing progression of capillary occlusion and ischemia. In some embodiments, the dots have a size of about 100 microns. In other embodiments, the dots have a size of about 80 microns. In yet other embodiments, the dots have a size of about 60 microns. In some embodiments, a plurality of dots are approximately regularly spaced in two dimensions, forming a grid pattern of dots (see, e.g., FIG. 7). The size and spacing of the dots of a grid can be selected so that the edges of each dot are less than about 140 microns from the edges of another dot, or an arteriole or venule (see, e.g., Example 4). The dimensions and spacing of the bands of a grid can be further selected to minimize visual field defects. In some embodiments, a grid of dots can be created on retinal tissue without concern of the retinal vasculature (e.g., arterioles and venules). In other embodiments, dots may be positioned approximately adjacent to arterioles and venules (see, e.g., Example 4). In yet other embodiments, dots may be positioned approximately centrally between an arteriole and a venule. Burns placed centrally between arterioles and venules or other oxygenation sources prevent propagation of ischemia as long as the distance from the ends of the bands to the oxygen sources is less than about 140 microns.

It will be recognized that irregularities in photocoagulation burn size and shape may occur with laser systems utilized to apply photocoagulation burns to the retina. Such irregularities may become more pronounced in the peripheral retina. In the peripheral retina, the angle of the incident laser beam may vary more as the lens used by the medical professional during the photocoagulation procedure approaches the limit of its tilt. As a larger portion of the beam is directed through the edge of the lens, spherical aberration may contribute to variation in burn size and shape. For example, round burns often become comet-shaped burns. However, as long as the bands or dots of the present disclosure remain sufficiently closely spaced (e.g., edges of individual burns within about 140 microns), such irregularities in shape and size should have negligible effect. Further, it will be recognized that the photocoagulation burns, pattern of burns, and methods described may be applied to laser systems capable of minimizing irregularities in burn size and shape.

In certain embodiments, photocoagulation burns can be one or more linear burns or series of burns that result in an approximately continuous linear burn having gaps between two burns small enough so that the intervening retina is oxygenated. In some embodiments, the linear burns or series of burns can be positioned to partition an area of ischemic retinal tissue from non-ischemic retinal tissue. The linear burns or series of burns can, for example, be positioned to encircle an area ischemic retinal tissue. In such a configuration, the linear burns or series of burns can prevent progression of ischemia across the burns from the ischemic retinal tissue to the non-ischemic tissue. The width of burn lines can be selected to minimize tissue damage while still preventing progression of ischemia. In certain embodiments, the width of linear burns or series of burns can be about 20 microns to about 100 microns. In other embodiments, the width of linear burns or series of burns can be selected to be wide enough to provide oxygenation sufficient to prevent the progression of ischemia across the linear burn or series of burns.

In other embodiments, photocoagulation burns can be one or more linear burns or series of burns that result in an approximately continuous linear burn having gaps between two burns small enough so that the intervening retina is oxygenated, where the linear burns or series of burns intersect and form a continuous web pattern. Such a web pattern is unlike the grid made up of burn bands or dots, in that the grid includes numerous bands or dots with fairly regularly spacing in two dimensions. With the continuous web pattern, the linear burns or series of burns intersect at approximately right angles to produce a continuous web pattern. A continuous web pattern can be positioned over non-ischemic retinal tissue to prevent progression of ischemia occurring from the retinal disease process within the area of non-ischemic retina. In certain embodiments, the continuous web extends beyond an area of ischemic retinal tissue into adjacent non-ischemic tissue. The distance the continuous web extends into the adjacent non-ischemic tissue can be selected to minimize or prevent progression of ischemia into the non-ischemic tissue. This distance can be balanced with the need to minimize or limit damage to the non-ischemic tissue caused by the burns of the continuous web. Spacing between laser burn lines and width of burn lines can be selected to minimize tissue damage while still preventing progression of ischemia. In certain embodiments, the width of linear burns or series of burns can be about 20 microns to about 100 microns. In other embodiments, the width of liner burns or series of burns can be selected to be wide enough to provide oxygenation sufficient to prevent the progression of ischemia across the linear burns or series of burns.

Targeted Photocoagulation for the Treatment and Prevention of Macular Edema

Certain aspects provide methods for applying photocoagulation burns to the macula to treat or prevent progressive retinal disease and/or macular edema. The methods include precisely placing small laser photocoagulation burns within the macula at specific sites to prevent progression of macular capillary occlusion. The progression of capillary loss in the diabetic macula can be modeled, and in some cases, models can be used to identify certain capillary occlusions that may cause progressive occlusion of other nearby capillaries. In some embodiments, computer modelling can be used to produce a risk map of those capillary segments likely to cause progression of ischemia by promoting occlusion of nearby capillaries. In other embodiments, a model can be used to determine the distance from a point on the macula, such as a capillary segment, to the next-nearest (but not to the nearest) capillary. This distance may be used to identify those areas of the macula that may benefit from additional modelling, functioning as an initial filter for which areas of the macula are most vulnerable to ischemic progression and may be definitively identified by modelling. With the occlusion of a capillary, the surrounding retinal tissue becomes hypoxic, and may result in increases in generation of VEGF and other factors, leading to excess local levels. This can result in progressive macular ischemia/hypoxia in addition to the local generation of VEGF, resulting in leakage from surrounding capillaries and the development of macular edema. By identifying those capillary segments likely to cause progression of ischemia, a small number of photocoagulation burns, including a single burn, may be placed at the site of the identified capillary segment. The photocoagulation burn may then act as an oxygen source, preventing the progression of ischemia from the identified capillary segment should it become occluded.

Macular edema is the leading cause of moderate visual loss in the working age population in the United States. Currently, about 40% of patients with diabetic macular edema receive laser treatment as an adjunct to treatment with intra-ocularly injected anti-VEGF agents. Current laser treatments are often in the form of a grid pattern of laser photocoagulation burns that are largely applied without the use of predictive modeling. As described herein, modelling can be used to identify those capillaries likely to cause propagation of ischemia/hypoxia. In some embodiments, predictive modeling can be used to identify those capillaries or capillary segments with the greatest distance to the next nearest capillary, as this distance can indicate the distance over which oxygen would need to diffuse to relieve hypoxia in the retinal tissue supplied by the occluded capillary. By predicting which capillaries around the fovea are most likely to promote propagation of ischemia if occluded, it is possible to predict which areas of the macula will benefit from macular laser treatment to treat or prevent progressive retinal capillary occlusion and macular edema.

Without wishing to be limited by any particular theory, treatment of macular edema or prevention of propagation of capillary occlusion may be a result of improved oxygenation of the laser treated macular areas, thereby preventing ischemic-driven elevation of VEGF, which itself may act to drive propagation of capillary occlusion.

Some embodiments of the present disclosure provide methods for applying photocoagulation burns to the macula to treat or prevent progressive retinal disease and/or macular edema. In certain embodiments, photocoagulation burns can be precisely applied to the macula at locations predicted to promote progression of ischemia should they become ischemic/hypoxic (e.g., due to capillary occlusion). The targeted photocoagulation burns can prevent the progression of macular ischemia/hypoxia. By preventing the progression of macular ischemia/hypoxia, progressive retinal disease and/or macular edema may be treated or prevented. In such embodiments, the capillary anatomy of the patient's macula can be determined using common imaging techniques, including but not limited to adaptive optics scanning laser ophthalmoscopy (AOSLO), angiography, and optical coherence tomography-angiography (OCT-A). Once the capillary anatomy is known, a model may be applied to determine the likelihood of an area of the macula, such as the area near a capillary segment, will cause the propagation of capillary occlusion following an initial occlusion event. When a capillary becomes occluded, the occlusion of the capillary may cause an increase in local VEGF levels, which can cause occlusion of nearby capillaries, resulting in the progression of ischemia and an increase in hypoxic tissue area. By identifying those areas or capillary segments that are likely to promote progression of ischemia, it may be possible to apply small photocoagulation burns to the identified areas. These small burns can act as oxygen sources capable of preventing ischemic progression.

In certain embodiments, the capillary anatomy of a subject's macula may be incorporated into a model capable of predicting progression of capillary occlusion. Burns may then be applied to areas of the macula near those capillaries predicted by the model to be at risk of occlusion. An exemplary model capable of predicting progression of capillary occlusion is the model presented in the Materials and Methods section, and in Fu et al., PLoS Comput Biol (2016) June 14; 12(6):e1004932, which is hereby incorporated by reference in its entirety for all purposes. The model, applied to distinct capillary networks in different retinal regions, including the macula, yields results comparable to clinical observations in those regions and can be used to identify those capillaries whose closure is likely to cause progression of ischemia and hypoxia.

Figure 8:
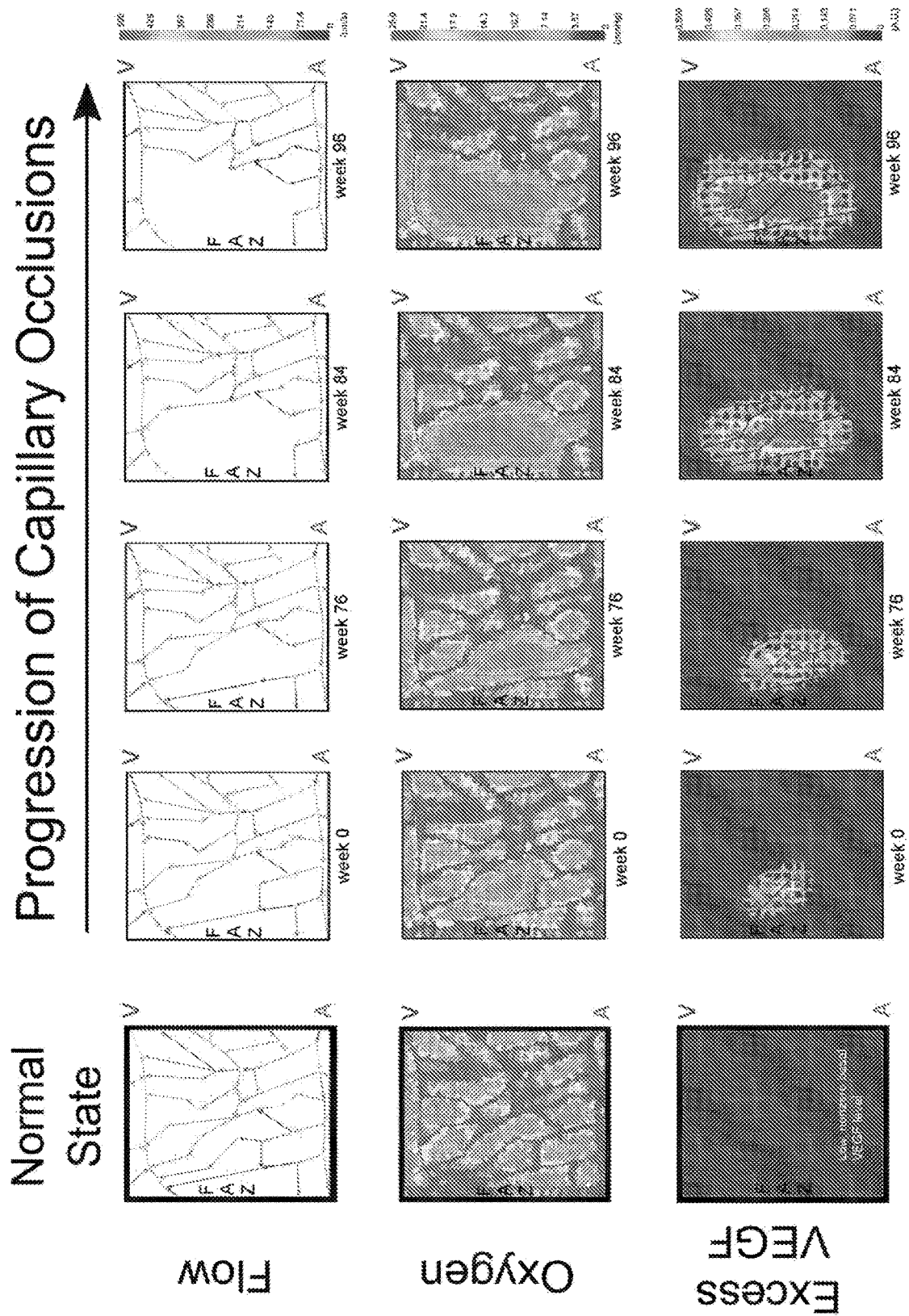
FIG. 8 depicts exemplary model simulations of macular capillary occlusion, ischemia, and excess VEGF expression. The model described in the Materials and Methods was used as a basis for all simulations.

Turning to FIG. 8, in untreated simulations run using the model described in the Materials and Methods section (see also Fu et al., 2016), a sporadic, isolated capillary occlusion is demonstrated to induce local hypoxia. Under normal conditions, cells are normoxic and no excess VEGF is produced. As demonstrated in FIG. 8, an initial capillary occlusion results in nearby cells becoming hypoxic. Dependent on the size of the resulting hypoxic area, which is largely determined by regional vascular density, capillary occlusion may trigger progression of occlusion in adjacent capillaries.

Figure 9:
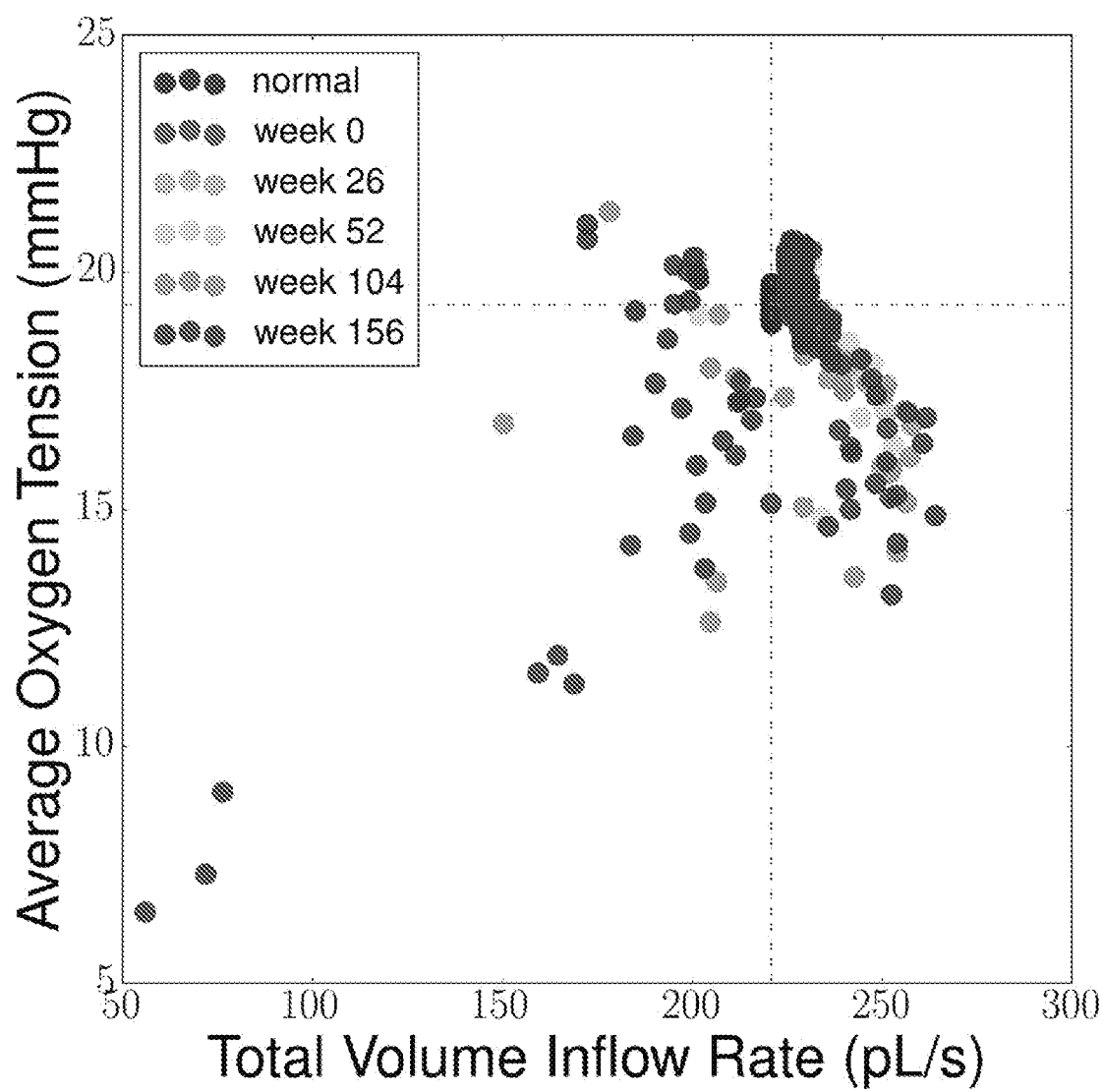
FIG. 9 depicts a perfusion-oxygenation phase diagram representing the presence of progression of capillary occlusion in computer simulations.

To determine whether all capillary segments have identical potential to cause or promote progression of capillary occlusion, replicate simulations of the model were run as described in the Materials and Methods section with randomly selected initial occlusion sites. The probabilistic aspect of the capillary occlusions means that repeated runs of the model will not produce identical patterns of capillary loss but similarity of replications will be strongly influenced by network structure. Once an initial occlusion site was selected, the order of further capillary occlusions, if any, was stochastic. Simulation results were arranged in a perfusion-oxygenation phase diagram, depicted in FIG. 9. Colors from dark blue to dark red (see legend of FIG. 9) indicate simulated time from initial state (i.e., week 0 at which time introduction of random capillary occlusion occurs) until week 156. Overlapped dark blue and dark red spots represent cases without progression. Dark red spots located in the bottom left quadrant indicate progression.

Figure 10A:
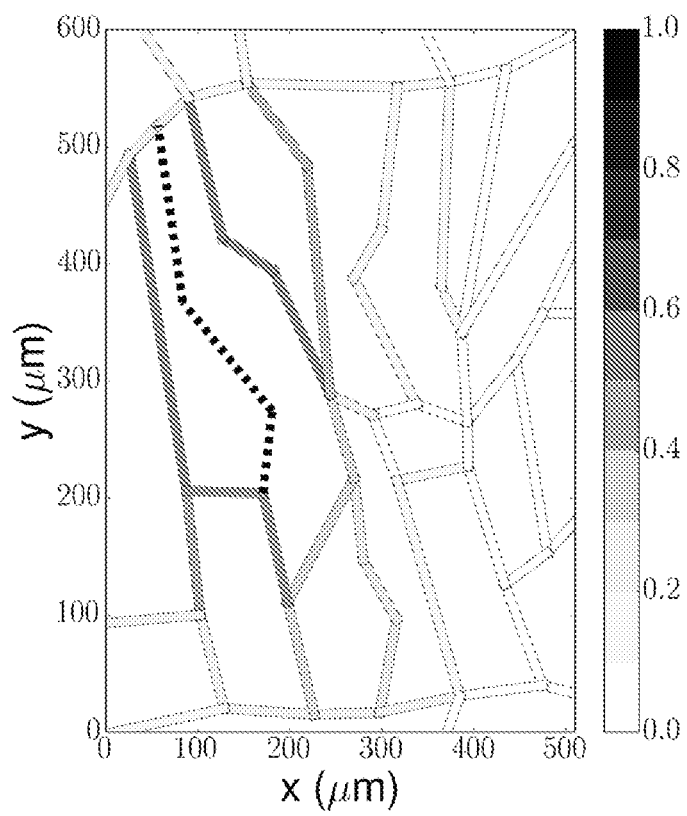
FIG. 10A depicts a modeled risk map indicating the frequency of surrounding capillary occlusion over 30 replicate computer simulations where the capillary segment indicated by the dashed line is occluded at time 0.
Figure 10B:
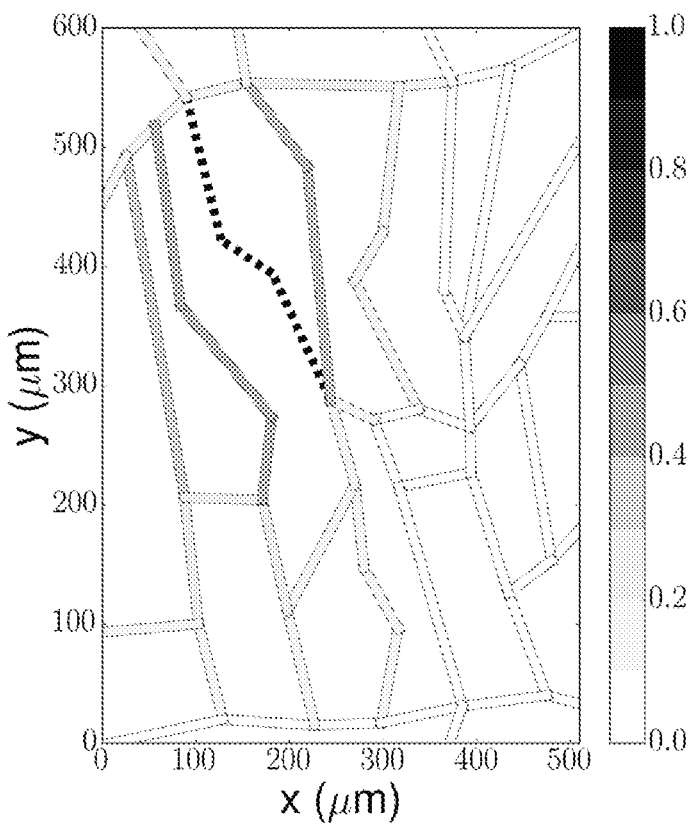
FIG. 10B depicts a modeled risk map indicating the frequency of surrounding capillary occlusion over 45 replicate computer simulations where the capillary segment indicated by the dashed line is occluded at time 0.

By replicating a simulation multiple times, a risk map may be generated. An exemplary risk map is depicted in FIG. 10A. The risk map of FIG. 10A was developed following 30 replicate simulations with the same initial occlusion site, which is indicated by the dashed line. The depicted heat map represents the frequency of individual capillary segments being occluded at the end of three simulated years out of all simulations with the same initial occlusion site. FIG. 10B depicts a similar risk map to FIG. 10A, although for a different initially occluded capillary segment. The risk map of FIG. 10B was derived from 45 replicate simulations with the same initial occlusion site (indicated by the dashed line). Simulations determined that closure of the capillary segments indicated in FIGS. 10A and 10B accounted for the majority of simulations indicating progression depicted in the perfusion-oxygenation phase diagram of FIG. 9.

Figures 11A, 11B:
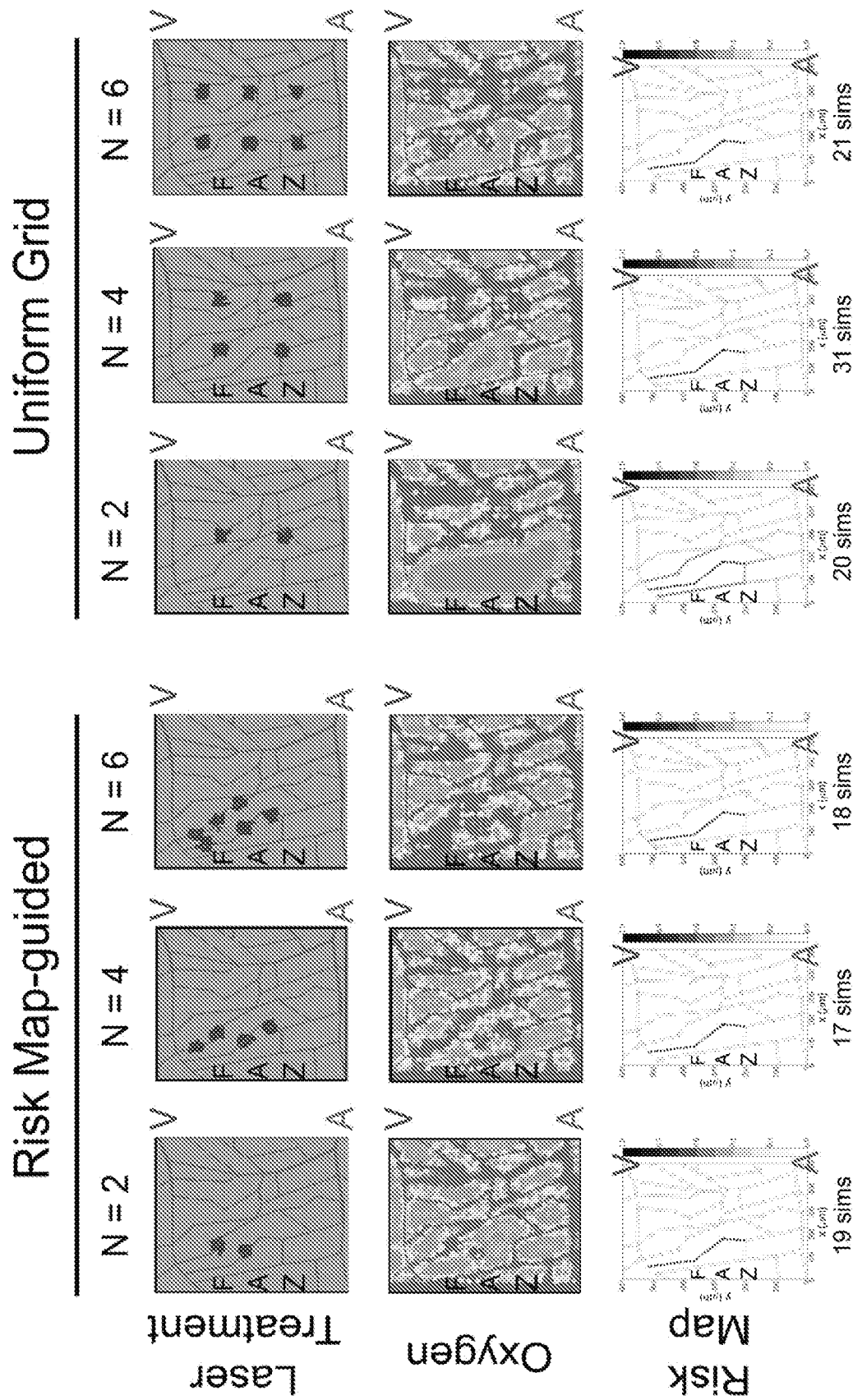
FIGS. 11A-11B depicts model treatment outcomes using risk map-guided (FIG. 11A) or uniform grid patterns (FIG. 11B) of photocoagulation burns. The burn pattern (top row), oxygen map (middle row), and risk map from replicate simulations following burn treatment (bottom row) are depicted.

In certain embodiments, one or more burns may be placed along or near one or more capillary segments identified by the model as being likely to cause the progression of ischemia should the identified capillary segment itself become occluded. For example, the capillary segments indicated as dashed lines in FIGS. 10A and 10B were identified as causing the majority of occlusion progression. Following modelling, burns can be applied to the macula along or near the two identified capillary segments (see, e.g., FIG. 11A). As depicted in 11A, modeled burns having a diameter of 50 µm were applied along the two identified capillary segments (dashed lines of FIGS. 10A-10B). According to the model, the small, targeted burns to those capillary segments predicted to be at risk of occlusion and to cause progression of capillary occlusion can effectively prevent progression of ischemia (see FIG. 11A). The ability of these burns to prevent progression of ischemia are evidenced by the risk maps presented in the bottom row of FIG. 11A. In contrast, burns placed as a grid in a non-targeted manner in the model demonstrated that such a pattern of burns is only effective in prevention of capillary occlusion if the grid is sufficiently dense (see, e.g., FIG. 11B). Generating unnecessary burns to the macula may increase vision loss. Targeting specific areas of the macula can not only prevent progression of ischemia and hypoxia within the macula, but may also reduce vision loss relative to current treatments due to the small number of burns required.

In certain embodiments, the spacing or density of macular capillaries may be used to determine which, if any, areas of the macula or particular capillaries or capillary segments may benefit from additional modelling. For example, if all capillaries or capillary segments with in the macula or an area of the macula have a spacing of about 140 microns or less not to the nearest capillary, but to the next nearest capillary, the macula or that area of the macula may be determined to be at low risk of progressive occlusion, and therefore modelling of the macula or that area of the macula may be skipped. If, however, spacing between next-nearest capillaries of the macula or an area of the macula is greater than about 140 microns, modelling of the macula or that area of the macula may be beneficial to identify those areas of the macula, such as along a capillary segment, that may benefit from one or more photocoagulation burns to prevent progression of ischemia should the area become hypoxic or the capillary segment become occluded. Therefore, in some embodiments described herein, methods may further comprise determining the distance between next-nearest capillaries or capillary segments within the macula. Where the distance between next-nearest capillaries or capillary segments in the macula or an area of the macula is determined to be greater than about 140 microns, capillary segments in the macula or the area of the macula having such a spacing may be further modeled as described herein to determine whether those capillaries or capillary segments are at risk of causing progression of ischemia if they become occluded.

In some embodiments, only a small number of burns may be required to prevent propagation of ischemia/hypoxia within the macula. The small number of burns may be targeted to those areas predicted to have a high likelihood of ischemic propagation. In other embodiments, a plurality of burns can be applied to the macula. Where a plurality of burns is applied to the macula, this may include a small number of burns focused over those areas of the macula predicted to have a high likelihood of ischemic propagation, or include a larger number of burns, again focused over those areas of the macula predicted to have a high likelihood of ischemic propagation, but also extending beyond such areas.

In certain embodiments, burns applied to the macula can be about 100 microns in diameter or less. In some embodiments, burns applied to the macula can be about 50 microns in diameter. In other embodiments, burns applied to the macula can be smaller than about 50 microns.

In certain embodiments, the burns can be applied to selected areas of the macula under manual control using a laser system. In other embodiments, the burns can be applied to selected areas of the macula using a laser system under automated control and/or registered to the retinal vasculature.

In certain embodiments, an area (e.g., capillary or capillary segment, or adjacent tissue) may be selected when a risk map for a given capillary or capillary segment indicates a frequency of occlusion of surrounding capillaries of about 0.2 or greater following model simulation.

Another aspect provides systems for carrying out a method described herein or assisting in the completion of such a method. In some embodiments, the system may be recognized as a macular capillary modelling computer system implementing the modelling and selection of capillaries or capillary segments of the above described methods. Further, in describing the macular capillary modelling system, one or more individual processes described above for modelling progression of capillary occlusion and identification of capillaries or capillary segments likely to cause such progression may be separated out and represented as a subsystem of the overall macular capillary modelling computer system. A subsystem of the macular capillary modelling computer system may be assigned, in whole or in part, to a particular hardware implemented system, such as a dedicated Application Specific Integrated Circuit (ASIC) or Field Programmable Gate Array (FPGA) or other hardware implemented system. One or more subsystems, in whole or in part, may alternatively be implemented as software or firmware instructions defining the operation of a computer system with specific regard to the one or more subsystems implemented as software or firmware instructions. The software or firmware instructions may cause the Central Processing Unit, memory, and/or other systems of a computer system to operate in particular accordance with the particular one or more subsystems designated features. Furthermore, various embodiments of the present invention may further provide alternate choices for laser treatment, proving advantageous for computing optimal choices for the wide variety of lesions encountered in practice.

In certain embodiments a system may include the macular capillary modelling computer system and one or more additional sub-systems, such as, for example, a photocoagulation laser system and an imaging system, such as an angiography system, AOSLO system, or a OCT-A system. In certain embodiments the various sub-systems may coordinate with one another to accomplish a treatment method described herein. For example, an imaging system may be configured to image a subject's macula and determine the capillary anatomy thereof, and transmit an image of the capillary anatomy to the macular capillary modelling computer system. The macular capillary modelling system may be configured to identify and select those capillaries or capillary segments likely to cause or promote progression of ischemia, and provide a map of the identified and selected capillaries or capillary segments to a photocoagulation laser system. The photocoagulation laser system may then apply photocoagulation burns to the identified and selected areas, either in a guided fashion with the input of a medical professional, or automatically.

In some embodiments, a system may include a processor and a memory comprising one or more computer-readable media having computer-executable instructions embodied thereof, wherein, when executed by the processor, the computer executable instructions cause the processor to identify one or more areas of the macula predicted to cause progression of ischemia following occlusion of a capillary or capillary segment at or near the one or more areas. The certain embodiments, the processor may be configured to receive an input of the subject's macular capillary network. Identification of one or more areas of the macula predicted to cause progression of ischemia following occlusion of a capillary or capillary segment at or near the one or more areas may include modelling the subject's macular capillary anatomy, as describe in the Materials and Methods section. A risk map for each capillary or capillary segment may then be generated, and one or more capillaries or capillary segments predicted by the risk map for each capillary or capillary segment to cause progression of ischemia if occluded may be selected. One or more capillaries or capillary segments may be selected when a risk map for a particular capillary or capillary segment indicates a frequency of occlusion of surrounding capillaries of about 0.2 or greater following a model simulation.

EXAMPLES

The materials, methods, and embodiments described herein are further defined in the following Examples. Certain embodiments are defined in the Examples herein. It should be understood that these Examples, while indicating certain embodiments, are given by way of illustration only. From the disclosure herein and these Examples, one skilled in the art can ascertain the essential characteristics of this invention, and without departing from the spirit and scope thereof, can make various changes and modifications of the invention to adapt it to various usages and conditions.

Example 1—Computational Model of Peripheral Photocoagulation for the Prevention of Progressive Diabetic Capillary Occlusion In an exemplary embodiment, a computational model of the propagation of retinal ischemia in diabetic retinopathy was developed. The model was used to analyze the consequences of various patterns of peripheral retinal photocoagulation. The model addresses retinal ischemia as a phenomenon of adverse local feedback in which once a capillary is occluded there is an elevated probability of occlusion of adjacent capillaries resulting in enlarging areas of retinal ischemia. In the model, areas of retinal ischemia tend to propagate, increasing in size over time, and are restrained by the oxygenated areas surrounding larger retinal vessels as retinal oxygenation interferes with the adverse local feedback process. Modelling retinal burns as local oxygen sources, different sizes and patterns of burns had different effects on the propagation of retinal ischemia. The model allowed for the testing of different patterns and sizes of burns quite different to that utilized in standard PRP and PASCAL. The patterns of retinal burns were optimized with regard to the area of retina photocoagulated summed with the area of ischemic retina. Certain patterns of retinal burns were effective, within the model, in preventing the spatial spread of ischemia by creating oxygenated boundaries across which the ischemia does not propagate.

The computational model was developed based on realistic assumptions for vascular flow delivery of oxygen (oxygen advection), oxygen diffusion from vessels and consumption by tissue, VEGF production by Mueller cells with production functionally determined by the degree of local hypoxia, VEGF diffusion and consumption by various cells, and probabilistic occlusion of capillaries logistically related to local VEGF levels and inversely related to vessel diameter and flow.

Figure 1B:
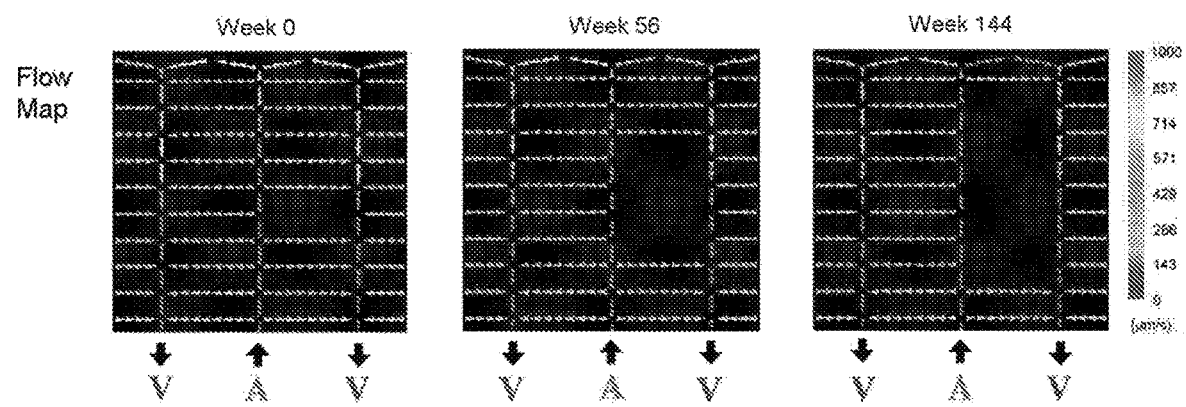
FIG. 1B depicts flow velocity maps at given time points following an initial capillary occlusion without photocoagulation.
Figure 1C:
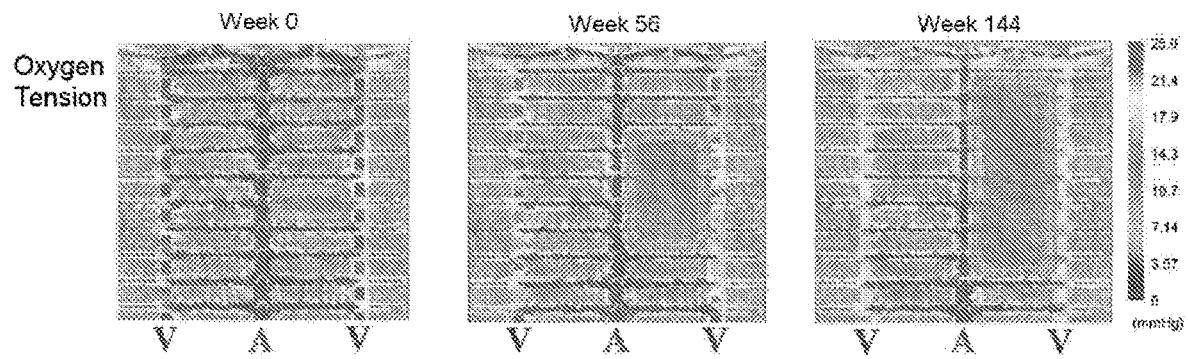
FIG. 1C depicts oxygen tension maps at given time points following an initial capillary occlusion without photocoagulation.

Referring to FIG. 1, the left panel of FIG. 1A depicts a 2D view of the configuration of the retinal capillary network, Mueller cells, and other retinal cells in the in silico peripheral retina. Vessel pattern and diameters are from the literature (Spitznas M., and Bornfeld N. *The Architecture of the Most Peripheral Retinal Vessels*. Albrecht Von Graefes Arch Klin Exp Opthalmol. 1977; 203(3-4):217-29, which is incorporated herein by reference in its entirety). The center panel of FIG. 1A depicts a flow velocity map of the model vascular network. Capillaries carry blood flow at lesser velocities than arterioles, venules, and the shunting vessels, the upper most angulated vessels. The right panel of FIG. 1A depicts an oxygen tension map of the modeled section. Cells in the proximity of vessels have relatively better oxygenation than those located at a greater distance, but no area is ischemic under normal conditions. FIG. 1B depicts flow velocity maps at given time points following an initial capillary occlusion without photocoagulation. The left panel of FIG. 1B (week 0) depicts closure of a capillary in an arterio-venous (AV) sector. The middle and right panels of FIG. 1B (week 56 and week 144, respectively) depict a cascade of capillary occlusions propagating anteriorly and posteriorly within the same sector, and therefore the flow map shows a larger gap, a larger area of ischemic retina. The color bar has units of μm/s. Warmer color represents greater flow velocity. FIG. 1C depicts oxygen tension maps at given time points following an initial capillary occlusion without photocoagulation. The left panel of FIG. 1C depicts a group of poorly oxygenated cells, area in blue, near the initially occluded vessel. The middle and right panels of FIG. 1C (week 56 and week 144, respectively) depict the expansion of the ischemic region in response to the increasing number of capillary occlusions. Oxygen tension in the venules also drops over time. Color bar has units of mmHg Warmer colors represent higher oxygen tension.

Simulations using the computational model demonstrated that an initial capillary occlusion, without laser treatment, often but not always, led to a cascade of derived occlusions and large contiguous ischemic areas anatomically confined by an arteriole and venule (FIGS. 1B and 1C). A stochastic occurrence of capillary occlusion broke a capillary flow pathway and led to an ischemic region near the initially occluded vessel (FIG. 1B left; week 0). Hypoxic Mueller cells significantly elevated local synthesis of VEGF which diffused to other nearby vessels, raising the probability of their occlusion Due to their comparably large flow velocity and large luminal diameters, the arteriole and venule are relatively protected from occlusion as they tend to be in the clinical situation until late in the progressive ischemic process. Derived capillary occlusions emerged at other nearby capillaries. Within the retina, this results in an anterior-posterior expansion of the no-flow region (FIG. 1B middle and right), and of the corresponding ischemia (FIG. 1B) and hypoxia (FIG. 1C).

Example 2—Effects of Dot and Band Laser Burn Density on Ischemia Progression

In another exemplary embodiment, the computational model described in Examples 1 and the Materials and Methods section was used to determine the effects of dot and band laser burn density on ischemia progression in the retina. While common PRP uses laser burns with a typical size of 250-500 microns, the computational model indicated that regularly patterned burns of much smaller sizes would effectively prevent progression of capillary occlusions in diabetic retinopathy while causing less damage to retinal tissue.

Two basic patterns of laser burns with the same total ablated area of retinal tissue were tested (FIG. 2). One pattern included square dotted laser burns alongside the arteriole and venule, each dot having a size of 100 microns by 100 microns. The other tested pattern was rectangular banded laser burns oriented relative to the arteriole and venule in a perpendicular orientation, each with a length of 300 microns and a width of 100 microns. All burns are depicted as dark patches in FIG. 2. Various densities of laser burns were tested and are tagged with label "N" followed by a number. Results are displayed in summary FIGS. 3 and 5. N indicates the number of laser burns placed in the modeled region during Band Pattern simulations, or indicates the pattern of dotted laser burns in Dot Pattern simulations that would give the same total burn area as the N banded burns. The sizes of burns given in the Dot Pattern or Band Pattern were mathematically intended values. In practice, sizes of burns were normally not precisely equivalent to but always close to these values in different simulations. In the model, burned tissue is areas of cells which have lost their physiological functions, such as consumption of oxygen and these areas also act as oxygen diffusion sources from the underlying choroid. A mathematically square burn has varying overlap with cells at its edges the degree of which determines the modelled life or death of a cell and thus gives a slight imprecision in burn size. This is depicted in FIG. 2 as the slight irregularities in otherwise linear burn edges. Treatment was limited to the middle two simulated AV sectors by placing laser burns in only these two sectors and by limiting candidate sites of random initial occlusions to capillaries within these two sectors Similar laser patterns and the simulated results can be applied for larger spatial scales composed of more sectors.

Figure 2A:
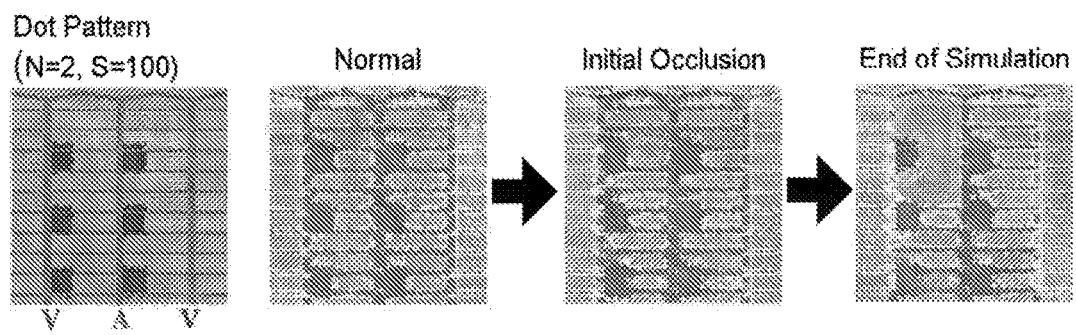
FIG. 2A depicts modeled photocoagulation Dot Patterns of N=2.
Figure 2B:
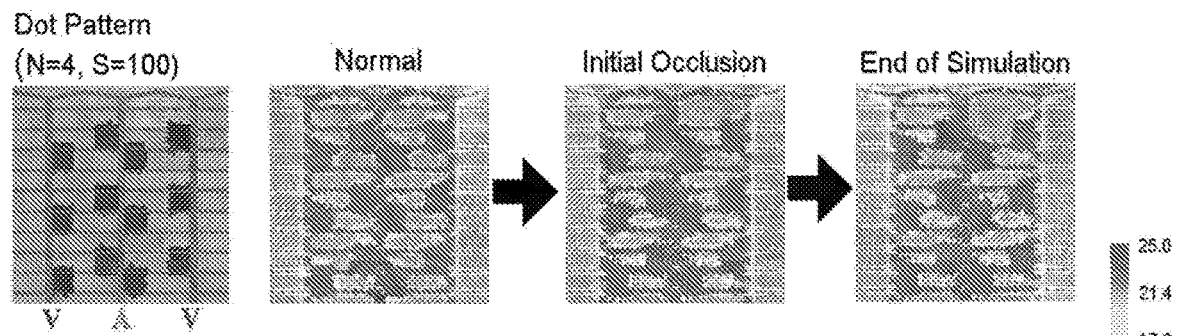
FIG. 2B depicts modeled photocoagulation Dot Patterns of N=4.
Figure 2C:
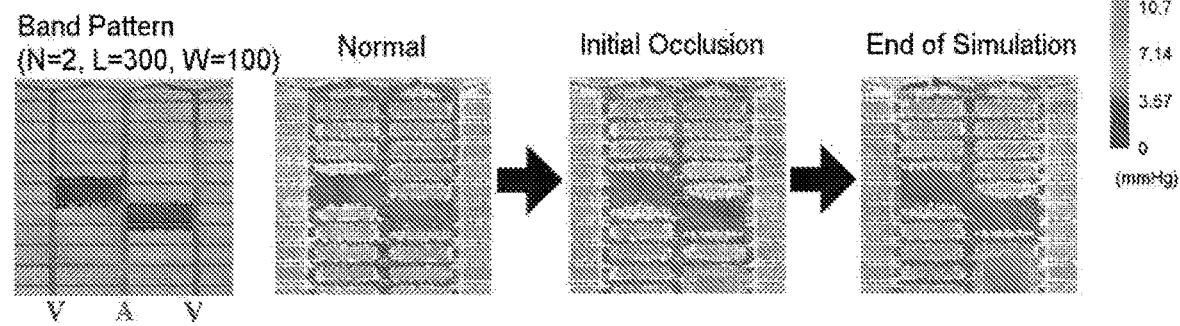
FIG. 2C depicts ischemic progression in modeling simulations with a Band Pattern of density N=2.
Figure 2D:
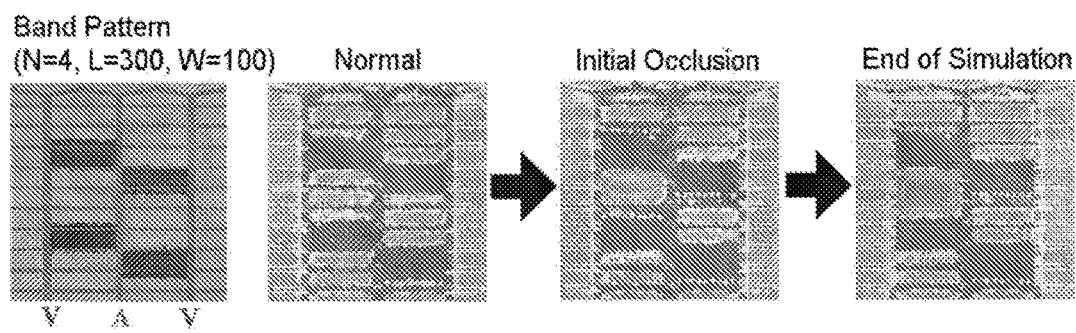
FIG. 2D depicts ischemic progression in modeling simulations with a Band Pattern of density N=4.
Figure 3A:
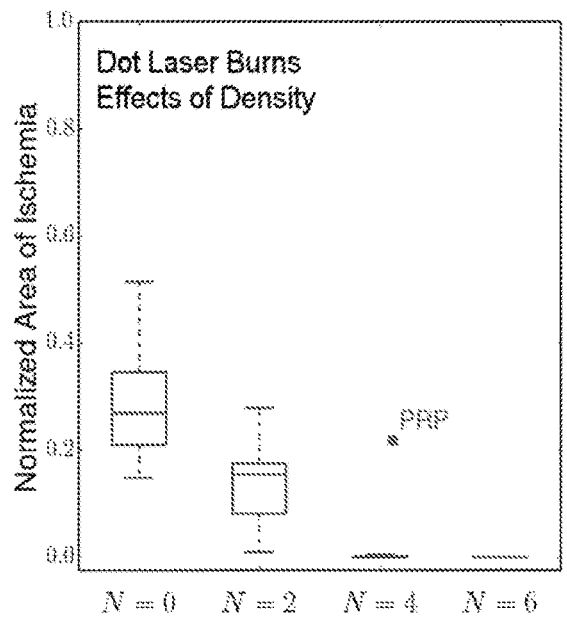
FIG. 3A is a box and whisker plot representing the relationship between the area of photocoagulated retina (burn area) and area of retinal ischemia. Area of ischemic progression was highly dependent on the Dot Pattern burn areas.

FIGS. 2A-2D depicts four photocoagulation therapy patterns using Dot Pattern (FIGS. 2A-2B) and Band Pattern (FIGS. 2C-2D) laser burns. The oxygen tension maps over time are also depicted. Ablated areas were enriched in oxygen under the normal condition and throughout the entire simulation secondary to oxygen delivery from the choroidal vasculature at the burn sites. In the Dot Pattern case with N=4 (FIG. 2B), an initial capillary occlusion stochastically occurred adjacent to the shunting vessel, and at the end of simulation progressed to cause just one derived capillary occlusion (FIG. 2B). The lasered regions appeared to supply adequate oxygen, preventing progression of the occlusion of the second capillary to a larger ischemic area. The location of the ischemic region was close to well-oxygenated regions with low VEGF, making it impossible for propagation to other intact retinal areas. In contrast, the Dot Pattern with N=2 (FIG. 2A) was incapable of preventing progression of ischemia, evidenced by the "by-passing" pattern of oxygen loss at the end of simulation. Data indicated that the smallest area of burns had the highest amount of progressive ischemic area (FIG. 3A).

In the Band Pattern simulation with N=4 (FIG. 2D), a random initial occlusion emerged in the middle zone of a sector and consequently stimulated additional capillary occlusions, but at the end of simulation, ischemia remained spatially confined (FIG. 2D, far right panel), with ischemic propagation unable to cross either a photocoagulation band or an arteriole or venule. Band Pattern with N=2 (FIG. 2C) showed a very similar preventive effect on ischemia progression but areas of possible ischemia were larger (FIG. 3C) Similar to the Dot Pattern case with N=4, the region of photocoagulation acted as an oxygen source, indicating low VEGF, and created a barrier to propagation of ischemia. Both simulated N=4 Band Pattern and Dot Pattern photocoagulations effectively inhibited diabetic capillary occlusions from progression. Similar preventive effects were also found in N=6 Band Pattern and Dot Pattern, but resulted in more retinal photocoagulation than necessary to prevent propagation as indicated by the elevation of the sum of burn area and ischemia in FIGS. 3B and 3D. In comparison, N=2 Dot Pattern therapies didn't prevent progression of capillary occlusions and produced large areas of ischemia, while the N=2 Band Pattern, despite creating effective barriers, allowed ischemic progression.

Example 3—Effects of Dot and Band Laser Burn Area on Ischemia Progression

In another exemplary embodiment, the computational model described in Examples 1 and the Materials and Methods section was used to determine the effects of dot and band laser burn area on ischemia progression in the retina. N=4 Band Pattern and Dot Pattern, were selected for additional modeling to evaluate their efficacy in prevention of ischemic propagation as a function of burn size (see FIG. 4).

In order to evaluate efficacy of simulated photocoagulations, end-of-simulation ischemic area was regarded as an important indicator of severity of diabetic progression, although visual function deficit in terms of burn area was also considered. The sum of the area of initial laser ablation and the area of ischemic propagation was thus evaluated. The optimal photocoagulation was defined as the lowest sum of ischemic area produced by capillary occlusion and tissue damage area from photocoagulation.

Figure 3B:
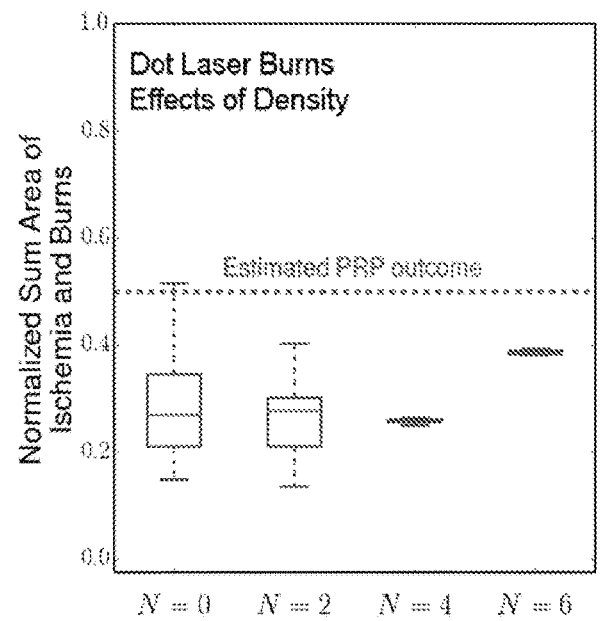
FIG. 3B is a box and whisker plot representing the relationship between the density of the Dot Pattern and the sum of laser treated and final ischemic areas of the retina as a measure of total compromised retina.
Figure 3C:
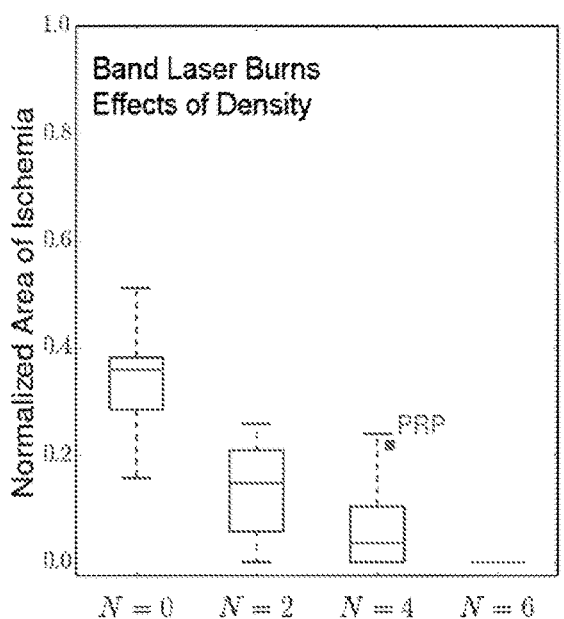
FIG. 3C is a box and whisker plot representing the relationship between the area of photocoagulated retina (burn area) and area of retinal ischemia. Area of ischemic progression was highly dependent on the Band Pattern burn areas.
Figure 3D:
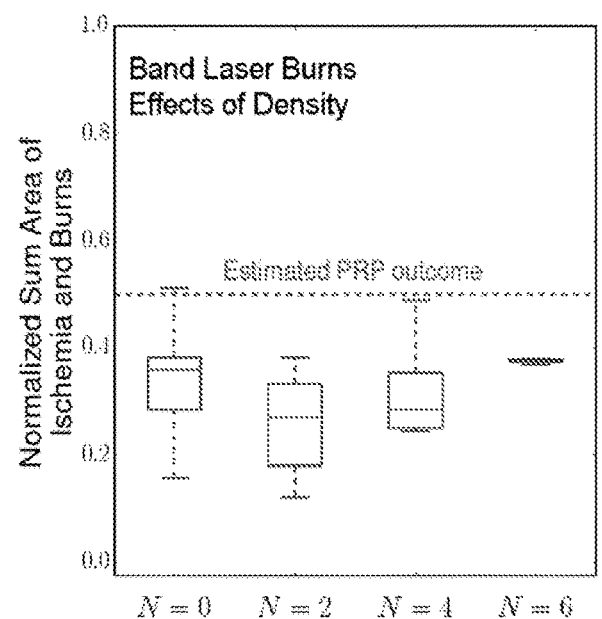
FIG. 3D is a box a whisker plot representing the relationship between the density of the Band Pattern and the sum of laser treated and final ischemic areas of the retina as a measure of total compromised retina.

For each of the Dot Pattern and Band Patterns described in Example 2, replicate simulations were run to average out any random effect existing from the stochastic nature of capillary occlusions in a single simulation. An evaluation diagram summarizing these simulation photocoagulation therapies was plotted (FIG. 3). The control group without any treatment was also plotted as 0 area of burn or N=0. For a given N, the normalized burn areas are essentially equal for the Dot and Band Patterns. Area of photocoagulation or N is plotted on the X axis, while the fraction of retina which is ischemic (the normalized area at the end of three simulated years) is plotted on the Y axis for the Dot (FIG. 3A) and Band (FIG. 3C) Patterns. Each of these panels also includes standard PRP as a green square. Outcomes from replicate simulations are given as box and whisker plots. FIGS. 3B and 3D plot N on the X axis and plots the normalized sum of treated and final ischemic areas on the Y axis. Estimated PRP outcome is given based on a 0.28 normalized burn area for the total peripheral retinal plus an estimated ischemic propagation for non-treated retina based on the control model.

In replicate simulations of the same therapy, individual outcomes showed slightly different initial burned areas, which reflected that intended square or rectangular burned regions would have anatomically fuzzy edges in practice. FIG. 3A depicts four box and whisker plots for the Dot Pattern of propagated ischemic area vs area of burns for N=0, and N=2, N=4 and N=6 patterns respectively. The larger the initial burned area, the smaller the ultimate ischemic area. If Dot Patterns had a total burn area as a fraction of total retina near to or larger than N=4 (0.26 normalized area), no apparent progression of ischemia occurred. FIG. 3B plots the normalized sum of burn area and ischemia against these different Dot Pattern conditions, and illustrates some dependence of the sum on area treated with the Dot Pattern, as decreased propagation occurs as normalized burn area is increased, and there is an inflection at N=4 indicating that laser treatments in excess of N=4 produced greater than necessary total retinal damage. The plots of FIGS. 3C and 3D for the Band Pattern illustrate similar results to the Dot Pattern, with decreased ischemic propagation as burn area increases (FIG. 3C), but the advantage being largely cancelled by the greater burn area essentially equaling the decreased ischemic area (FIG. 3D). A remarkable feature of both dot and band pattern plots is that ischemic propagation could be stopped at normalized burn areas comparable to standard PRP which does not stop ischemic progression. This is because the wide retinal areas between the large burns of standard PRP will behave similarly to the modelled untreated case with ischemic propagation. Total area of ischemic retina is important to the complications of diabetic retinopathy as VEGF released from this retina acts as the ultimate driver of diabetic neovascularization and some cases of macular edema.

Figure 4A:
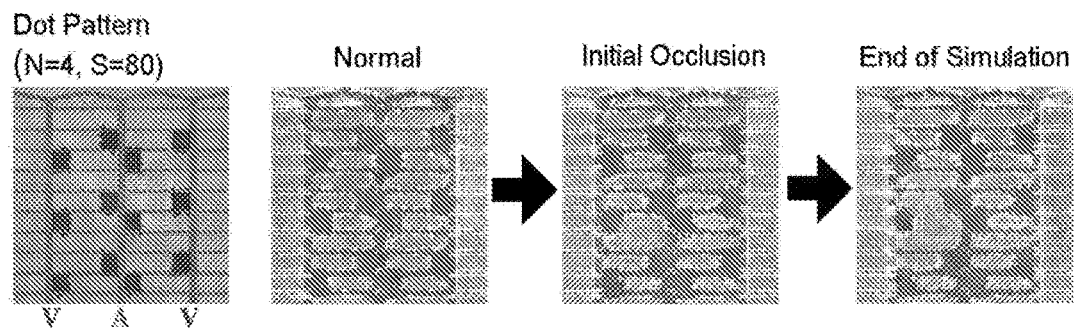
FIG. 4A depicts modeled photocoagulation Dot Patterns with Dots of 80 microns.
Figure 4B:
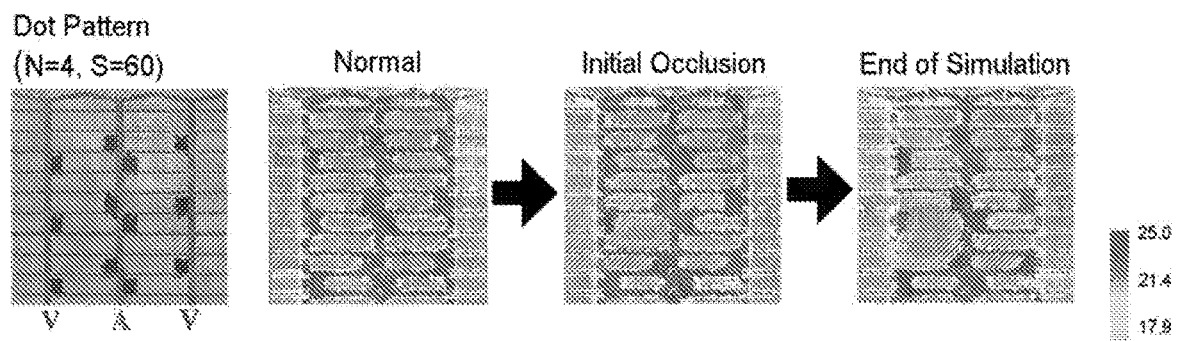
FIG. 4B depicts modeled photocoagulation Dot Patterns with Dots of 60 microns.
Figure 4C:
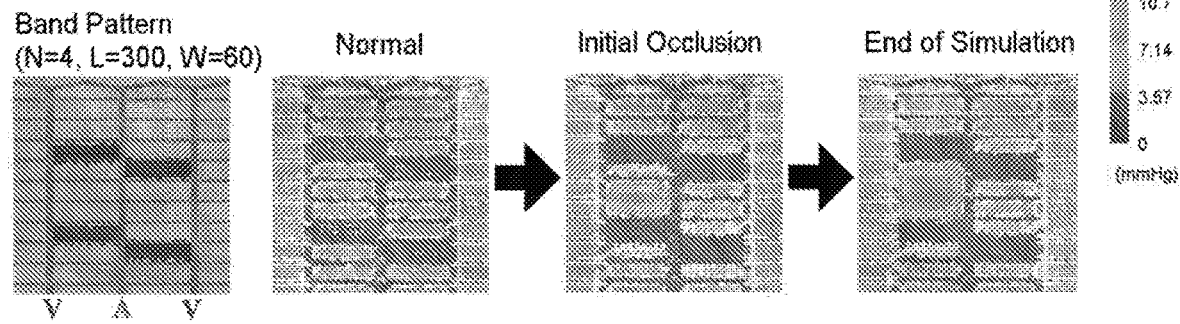
FIG. 4C depicts ischemic progression in modeling simulations with a Band Pattern having bands 300 microns long, 60 microns wide, and with a density of N=4.
Figure 4D:
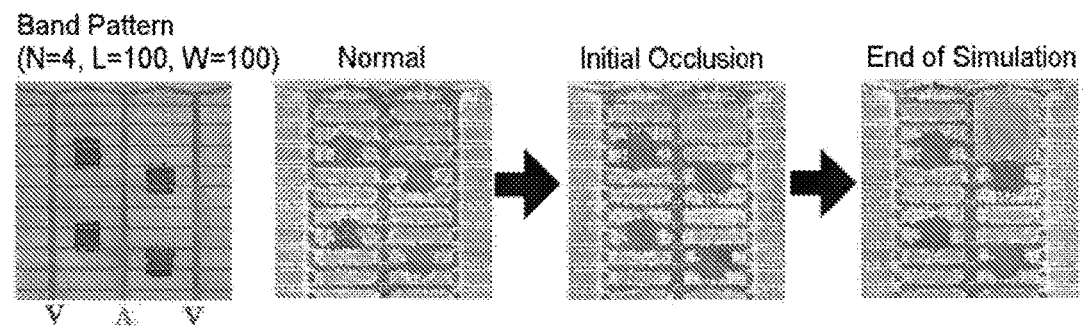
FIG. 4D depicts ischemic progression in modeling simulations with a Band Pattern having bands 100 microns long, 100 microns wide, and with a density of N=4.
Figure 5A:
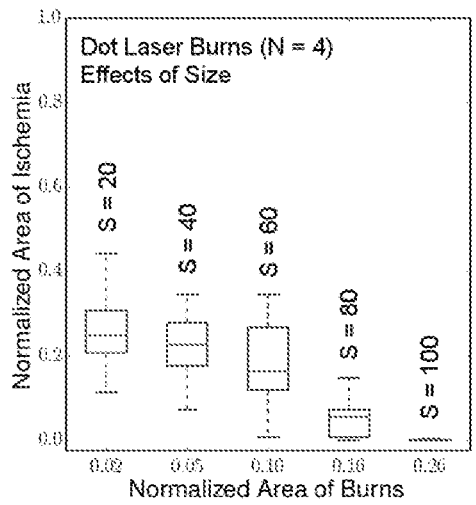
FIG. 5A is a box and whisker plot representing the relationship between the area of photocoagulated retina (burn area) and the area of ischemia. Area of ischemic progression was dependent on the size of the dots.
Figure 5B:
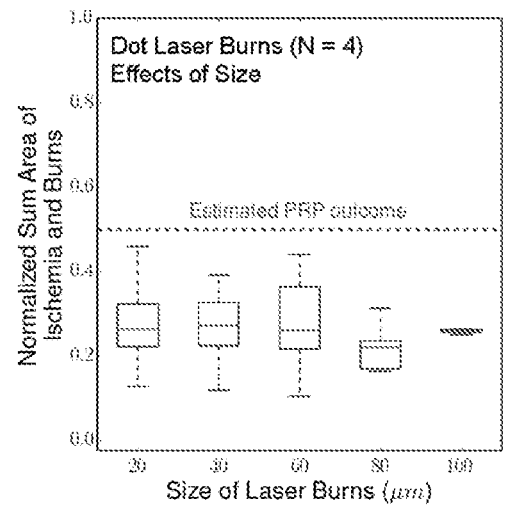
FIG. 5B is a box and whisker plot representing the relationship between the size of the individual dots (density N=4) and the sum of treated and final ischemic areas of the retina, indicating that for this density of spots, size has little effect on ischemic progression.

Example 4—Optimization of Dot and Band Laser Burn Area for Prevention of Ischemia Progression In another exemplary embodiment, the computational model described in Example 1 and the Materials and Methods section was used to optimize laser burn dimensions for the prevention of ischemic progression. Optimization determined the smallest burn area capable of effectively preventing propagation of ischemia, based on N=4 burn patterns The Dot and Band Patterns were adapted to achieve an optimal sum of burned area and ischemic area. With the Dot Pattern, the effect of decreasing edge size from 100 microns to 80, 60, 40, or 20 microns was examined. The Dot Pattern with edge sizes of S=80 microns and S=60 microns are depicted in FIGS. 4A and 4B, respectively. The S=80 Dot Pattern demonstrated better effectiveness in preventing progression of ischemia than S=60. The S=60 Dot Pattern appeared to be a transition point in efficacy, as Dot Patterns with smaller sizes resulted in even larger areas of ischemia (FIG. 5A). The S=20 dots reflected a theoretical minimum simulated burn size in the current model based on retinal cell size, and demonstrated little difference from the control simulation. While not all dot sizes are presented in FIG. 4, all cases are included in the evaluation diagram (FIG. 5).

Figure 5C:
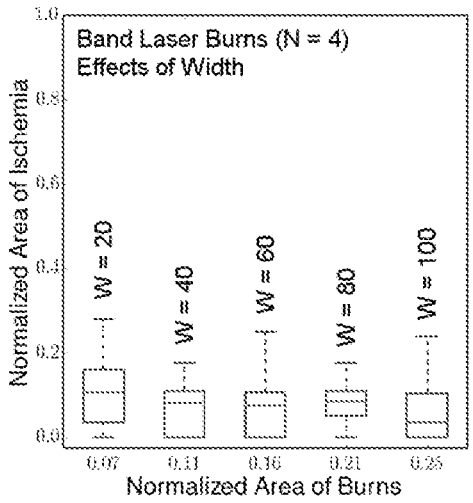
FIG. 5C is a box and whisker plot representing the relationship between the area of photocoagulated retina (burn area) and the area of ischemia. Burn area was dependent on the width of the bands (length kept constant). For these burns located centrally between the artery and vein, there was little ischemic progression regardless of width.
Figure 5D:
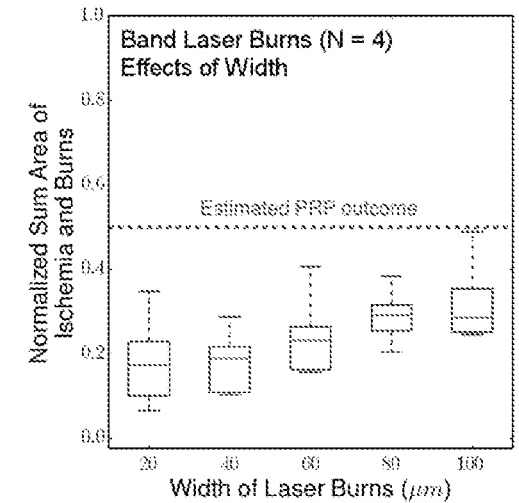
FIG. 5D is a box and whisker plot representing the relationship between the width of the individual bands (density N=4; length kept constant) and the sum of treated and final ischemic areas of the retina, indicating that the size of the burn is not pertinent if it is centrally placed.
Figure 5E:
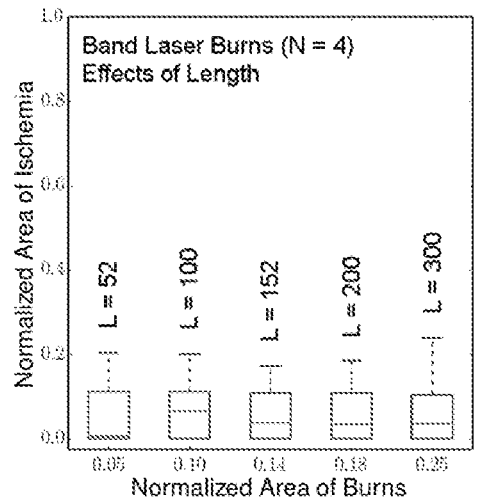
FIG. 5E is a box and whisker plot representing the relationship between the area of photocoagulated retina (burn area increasing with increased length at constant width) and the area of ischemia. Ischemic progression is almost nil at each length for these burns centrally placed between artery and vein.
Figure 5F:
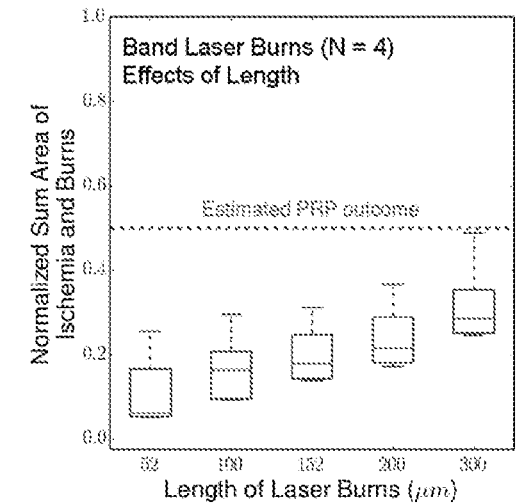
FIG. 5F is a box and whisker plot representing the relationship between the length of the individual bands (density N=4; width kept constant) and the sum of treated and final ischemic areas of the retina. Since each burn length prevented ischemic progression, the overall retinal compromise is increased at each longer band length.

With Band Patterns, changes in width ("W") or length ("L") were investigated. Band Pattern burns were thinned to investigate a theoretical minimal size that could substantially stop progression of diabetic capillary occlusions. The simulated widths were 100, 80, 60, 40, and 20 microns. In other simulations, Band Pattern burns were shortened equally from both ends to only cover the middle region of an AV sector, with the rationale that retinal areas near the venule and arteriole are relatively well oxygenated and protected against ischemia. Simulated lengths were 50, 74, 100, 124, and 300 microns. Examples of the simulated Band Pattern therapies are depicted in FIGS. 4C and 4D, illustrating changes in band pattern width and length. FIG. 4C depicts the ability of a Band Pattern of N=4 having bands of L=300 microns and W=60 microns to prevent progression of ischemia. FIG. 4D depicts the ability of a Band Pattern of N=4 having bands of L=100 microns and W=100 microns to prevent progression of ischemia. Both cases restricted progression of ischemia by creating barriers to propagation as illustrated in FIGS. 5C and 5E, which depict the results of replicate simulations.

The various Dot and Band Patterns were evaluated in replicative simulations, the results of which are illustrated in FIG. 5. FIG. 5A depicts box and whisker plots of the predicted ischemic areas for the different total burn areas of the different dot sizes. In general, more burn area resulted in less progression of ischemic area. In FIG. 5B, the summed areas of ischemia and burns is given on the Y axis as a function of burn size. The effect of increasing burn size and decreasing ischemic progression were largely complementary, and over the size range tested, were below the results with PRP. The variability of ischemic progression was observed to drop with the largest burn size, as illustrated by the diminished height of the box. The effects of the variation in band width are illustrated in FIGS. 5C and 5D, and the effects for variation in band length depicted in FIGS. 5E and 5F. No benefit was observed to increasing the burn dimensions of the Band Pattern. When the width of laser burns was decreased from 100 microns (default in basic band pattern) to as small as 20 microns (roughly the size of a single cell), the average area of ischemic progression remained more or less unchanged, indicating similar preventive effects for burns having different widths. Similar results were observed in simulations where the length of the bands was varied, with the bands approximately centered between arteriole and vein. This arrangement is therapeutically attractive, because during the optimization process, total burned area was decreased almost 80% over PRP.

Computational modelling indicated that the tested Dot Pattern and Band Patterns of photocoagulation effectively prevented progression of diabetic capillary occlusions as compared with traditional PRP treatment. Optimization of Dot Pattern therapy by shrinking the size of laser burns showed a critical size of gap between laser burns equal to about 140 microns, with gaps larger than about 140 microns demonstrating increased propagation of capillary occlusion (see, e.g., FIG. 5A). This corresponds to burn sizes between 60 and 80 microns at the N=4 spacing. Optimization of Band Pattern therapies via either thinning or shortening the laser burn, on the other hand, displayed surprisingly consistent performance in prevention of ischemic propagation with small areas of ablation (see FIGS. 5C and 5E). Of all optimized burn patterns, the Band Pattern having L=72 microns resulted in the smallest sum of retinal photocoagulation and ischemic area. This is consistent with the 140 micron gap for the Dot Pattern, as this band length results in gaps of about 125 microns between the central band of laser treatment and the adjacent arteriole and venule. Note that the difference between Dot and Band Patterns is superficial in terms of shape, but that in this model Dots were located adjacent to the arterioles and venules whereas Bands were centered between the two vessels. This distinction is important relative to the physiology of ischemic propagation.

Figure 6:
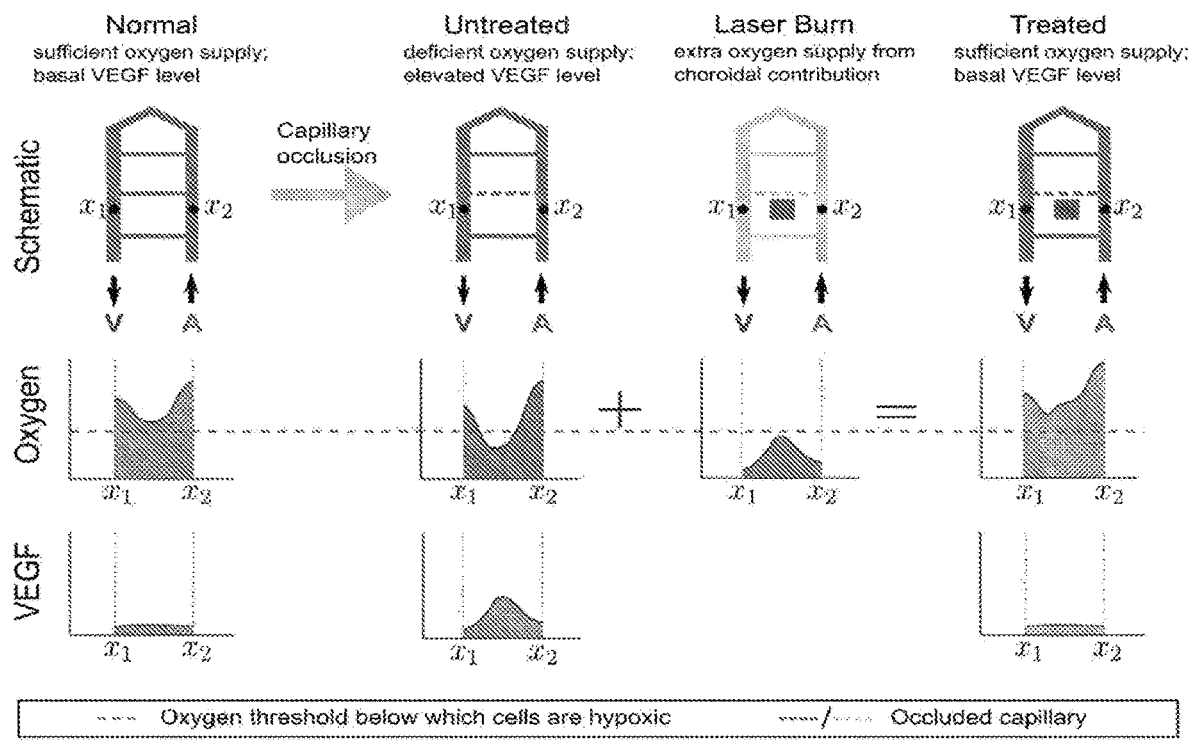
FIG. 6 is a representation of the predicted alteration in retinal oxygen profile produced by the band burn pattern and treating each individual burn as an oxygen source. The consequence of the burns is to eliminate retinal ischemia/hypoxia and therefor the local increase in factors such as VEGF.

A hypothesized mechanism of suppression of ischemic propagation is presented in a schematic of the oxygen landscape shift with laser treatment (FIG. 6). In the normal state oxygen tension is high near the arteriole and venule and lower at the central region between vessels, but no retina is hypoxic and therefor VEGF synthesis is at basal levels. This normal trough of oxygen tension is only slightly higher than the hypoxia threshold. Thus, a capillary occlusion causes cells in these regions to become hypoxic with resultant increase in VEGF synthesis and resulting elevation of probability of adjacent capillary occlusion. The oxygen landscape shifts upward when the laser burn introduces an oxygen source between the arteriole and venule raising the oxygen level in the oxygen trough above the hypoxic threshold, preventing elevated synthesis of VEGF, and therefore helps to prevent propagation of capillary occlusion.

Example 5—Computational Model Predicting Areas of Macula Likely to Become Hypdxic In an exemplary embodiment, a computational model for predicting areas of the macula likely to become hypoxic was developed. The model was used to identify those areas of the macula that are to become hypoxic so that the identified area or areas could be treated by a photocoagulation burn, thereby preventing that area from becoming hypoxic and preventing propagation of ischemia. The basis for model is described in further detail in the Materials and Methods section.

In untreated simulations, a sporadic, isolated capillary occlusion induced local hypoxia, and, dependent on the size of hypoxia, which is largely determined by regional vascular and density, may trigger progression of adjacent capillary occlusions and ischemia. An exemplary simulation with progression of capillary occlusions is depicted in FIG. 1. FIG. 1 depicts simulation of progression of capillary occlusions, ischemia, and excess VEGF production. Under normal conditions, cells were normoxic and no excess VDGF was produced. At week 0, an initial capillary occlusion occurred and cells nearby became hypoxic. Cells synthesized excess VEGF, which propagates spatially to reach adjacent capillaries and increased their probability of becoming occluded. At later time points, areas of capillary non-perfusion and ischemia progressively expanded.

To determine if all capillary segments in the patient-derived retinal arterio-venous sector had identical progressive potential, replicate simulations of the same model were run, with randomly selected initial occlusion sites. In an initial occlusion site was selected, the order of further capillary occlusions, if any, were stochastic. To determine if a simulation showed progression of capillary occlusions, simulation results were arranged in a perfusion-oxygenation phase diagram, such as that depicted in FIG. 2. In FIG. 2, the color-coded dots indicate simulated time from a normative initial state (week 0) until week 156. Overlapped dark blue and dark red dots represent cases without ischemic progression. Dark red dots located in the bottom left quadrant are indicative of ischemic progression. Only a small number of initial capillary closures had the propensity for progression, indicated by severe decrease in total blood flow rates and retinal oxygenation at the end of simulated 3 years (dark red dots in FIG. 2). This result led to further examination and identification of these initial capillary closures that have greatest progressive potential.

To identify which initial capillary closures had high propensity for progression of further capillary occlusions, the replicate simulations were grouped based on their initial occlusion site, and a risk map, or vulnerability map, was generated for each group. It was found that closures of two capillary segments in the patient-derived retinal arterio-venous sector were responsible for most instances of progression indicated in FIG. 2. The risk maps for these two capillary closures are depicted in FIGS. 3A-3B. Risk maps plat the frequency of every individual capillary segment being occluded at the end of a simulation of three years given a certain capillary segment becoming occluded at week 0. The risk maps were used to identify regions with high risk of becoming hypoxic and to select locations for treatment by small photocoagulation burns.

The risk map depicted in FIG. 3A is the result of 30 replicate simulations with the same initial occlusion site (black dashed line). The frequency of individual capillary segments being occluded at the end of the simulation is color coded. Frequency was determined relative to all simulations with the same initial occlusion site. The risk map depicted in FIG. 3B was generated similarly to that of FIG. 3A, but indicates the frequency of individual capillary segments being occluded at the end of the simulation when a different capillary section was initially occluded (dashed line), and is the result of 45 replicate simulations.

Results for treated simulations are depicted in FIG. 4. Burn size was set to 50 microns. Small burns targeted to risk map-guided capillary segments with high risk of triggering additional capillary occlusions were effective in preventing progression of ischemia regardless of burn density. In contrast, a uniform grid of small burns was effective in prevention of progression only if the density was great enough. The burn pattern is indicated in the top row of FIG. 4, while an oxygen map at the end of an exemplary simulation is provided in the middle row, and a risk map from replicate simulations is depicted in the bottom row. Risk map-guided laser burn patterns covered only those capillary segments with the greatest propensity for progression.

Materials and Methods—Computational Model

A Python script and Compucell3D model of the retinal vasculature has been developed and applied to a schematic peripheral retinal capillary network. The model is fully described below, and in Fu, X. et al., *Progression of Diabetic Capillary Occlusion: A Model*, PLoS Comput Biol, 2016 Jun. 14; 12(6):e1004932, which is hereby incorporated by reference in its entirety. The model is based on the histology of Spitznas M., and Bornfeld N. *The Architecture of the Most Peripheral Retinal Vessels*. Albrecht Von Graefes Arch Klin Exp Opthalmol. 1977; 203(3-4):217-29, which is incorporated herein by reference in its entirety.

A full vascular model from an arteriole to venules with the linking capillaries is included with oxygen advection, oxygen diffusion, and oxygen consumption, VEGF synthesis and destruction, probability of capillary occlusion, and retinal edema. Physiologically, a conceptually simple model of the diabetic retina treats Mueller cells as the sole retinal source of VEGF and assumes a slight elevation of VEGF production by Mueller cells in a diabetic retina higher than that in the normal retina as the permissive step distinguishing diabetics from normals. In the model, VEGF is produced by Mueller cells locally in variable amounts based on local cellular level oxygen saturation. VEGF diffuses from the Mueller cells and is consumed by the various cells including capillary endothelial cells but is not transported away by advection. The model vessels have endothelial cells which respond to local VEGF levels by an elevation of ICAMs and increased probability of capillary occlusion through leukocyte adhesion accomplished by the leukocyte CD11a, CD11b, and CD18 receptors induced by elevated glucose. The model is cycled many times and if a capillary occlusion occurs, all vascular flow rates, local oxygen tensions and VEGF levels are recalculated. The model's treatment of occlusion is irreversible, as it essentially assumes the capillary is at the stage of endothelial replicative exhaustion so that loss of an endothelial cell leaves uncovered basement membrane and results in capillary occlusion.

The model assumes that the vascular supply to each area of retina is 'critical' in that occlusion of a capillary will always result in ischemia of some area of physiologically dependent retina with a resultant considerable further local elevation of VEGF synthesis above the already somewhat elevated permissive level of VEGF by the now ischemic Mueller cells. This model describes a physiology in which occlusion of a capillary in the diabetic increases the probability of occlusion of adjacent capillaries in an adverse feedback cycle as hypoxia elevates VEGF which elevates endothelial ICAM levels which elevates capillary occlusion probability. Model capillary occlusions are always probabilistic functionally based on local VEGF levels and the calculated flows in the capillary segments. VEGF is a surrogate for the collective effects of various diffusible cytokines including VEGF which affect the probability of capillary occlusion.

In the present model, maps at various model times are made of capillary network structure, flow, and oxygen tensions. Shown in FIG. 1A is the configuration of retinal periphery cells and vessels under normal conditions, visualized at a two dimensional plane involving vasculature. With boundary blood pressures and oxygen tensions assigned, flow velocities were calculated and the oxygen steady state simulated (FIG. 1A). Larger vessels including the arteriole, venules and the peripheral shunt vessels showed greater blood flow velocities than do the capillaries. All cells were well oxygenated under normal conditions, and cells adjacent to vessels had higher oxygen tension than those distant from vessels.

FIGS. 1B and 1C show the progression of a capillary occlusion in terms of the flow map and the oxygen tension map with the occlusion occurring at week 0 and results shown in model weeks 56 and 144. Photocoagulation burns in the model become diffusive sources of oxygen equal in size and shape to that of a coagulation burn (see, e.g., FIG. 2). These burns, as oxygen sources, are able to prevent progressive capillary occlusion because oxygen blocks the initiation of the causal chain from hypoxia to elevated induced VEGF synthesis to increased probability of nearby capillary occlusion. Into the peripheral retinal capillary networks distinct patterns of laser burns were applied and the area of retina treated as well as the predicted area of retinal ischemia over the time were modelled. The sum of these two areas acts as a measure of the optimization of retinal photocoagulation with regard to visual function (see, e.g., Example 4).

Capillary Occlusion Model—Physiological Assumption

VEGF is a factor with a long history. First identified as a vascular permeability factor, it has become clear over time that it has other important roles as a factor in angiogenesis, endothelial cell proliferation, and also as a neuro-retinal protective factor. While retinal edema is modeled, the important property of VEGF for the present model is its role a mediator of elevated ICAM-1 on retinal endothelial cells. In the present model of progressive capillary occlusion, VEGF is the locally secreted molecule which diffuses and increases the likelihood of nearby capillary occlusion. As this pro-occlusive property is not as well-known and even possibly denied by some, the background supporting the choice of VEGF as a substance responsible for the adverse cycle of capillary occlusion is provided. This does not mean VEGF is by any means the only cytokine involved or that there is not an intervening cascade of events that generate the chronic inflammatory state that is diabetic retinopathy. Leukostasis is mediated by the diabetic activation of circulating leukocytes co-existing with marked upregulation of adhesion molecules such as ICAM-1 on the retinal vascular endothelium. These changes increase the likelihood of leukocyte adhesion to the retinal capillary endothelium and therefore the probability of capillary closure. The model does not detail the local, undoubtedly complex, phenomena such as the cumulative leukocyte mediated endothelial capillary damage resulting in endothelial replicative exhaustion culminating in capillary occlusion; they are treated as black boxes at this time.

The model treats elevation of one substance for simplicity, though likely the relative amounts of two substances, such as the balance of VEGF and pigment epithelium derived factor (PEDF), is what is often physiologically important. PEDF itself has complex neurotrophic, neuroprotective, and anti-angiogenic, anti-exudative and anti-inflammatory properties. High glucose decreases expression of PEDF in retinal Mueller cells as it simultaneously elevates VEGF expression. Additionally, vitreous levels of PEDF are significantly lower in patients with diabetic macular edema or proliferative diabetic retinopathy than in non-diabetic patients or diabetic patients without retinopathy, whereas in each situation VEGF is elevated. The model simplifies this duality by treating the physiological import of an imbalance as simply the concentration of VEGF. Certain steps in the progressive ischemic process must be met by a diffusible substance and ideally, anatomical and physiological support for each of the steps in the model is needed if VEGF is to be modeled as the diffusible substance. The local adverse positive feedback model could stand on its own, dealing only with the problem of diabetic ischemia as a geographic phenomenon, but it is more constructive to have model elements that correspond as closely as possibly to biological elements. A simple biological model is developed based on the observation that this substance is required to have a number of physiological properties which first create the permissive diabetic state of recurrent capillary endothelial cell loss by activated leukocytes, leads to permanent capillary occlusions from local endothelial depletion, and which in turn produces geographic propagation of capillary occlusions. This progression requires a substance, modelled as VEGF, and the retinal tissue to have the following characteristics:

Step 1: With the onset of hyperglycemia or the continued presence of hyperglycemia this substance must change its production in some way from that of the non-diabetic state.

Step 2: The change in concentration of this substance must cause some change in the retinal capillaries resulting in an increased probability of permanent capillary occlusion above essentially zero in the non-diabetic state.

Step 3: Capillary occlusion must in turn create local retinal ischemia and by some mechanism further elevate the level of the substance, meaning that ischemia cannot act to kill the cells producing the substance.

Step 4: Higher concentrations of this substance in a local retinal area must cause a higher likelihood of occlusion in nearby capillaries with the probability of occlusion functionally related to the concentration of the substance.

Step 1: Initial Slight Elevation of VEGF in Diabetes, Above the Basal Level of a Non-Diabetic, to Initiate a Non-Zero Probability of Activated Leukocyte Adhesion to the Capillary Endothelium.

Step 1 requires an initial slight elevation of VEGF in the retina in response to an elevation of glucose to create a non-zero probability of capillary occlusion as a way to create an initial state allowing capillary endothelial cell destruction and ultimately capillary occlusion. Ideally the cellular source of the VEGF should also be specified. Different retinal cell types respond to elevated glucose in a variety of ways. Retinal pigment epithelial (RPE) cells respond to acute elevation of glucose with an increased production of VEGF (as well as a decreased production of PEDF). Though these changes are in the directions required by the model, the secreted factors likely leave the basal portion of the RPE cells, below the posterior blood brain barrier, and move into the choriocapillaris, and not the neural retina. In addition, the choriocapillaris rather than the retinal vasculature provides most of the oxygen to the RPE, so loss of retinal capillaries is unlikely to reduce oxygenation of the RPE significantly, a key step in the hypothesized feedback loop (steps 3 and 4 above). The present retinal model therefore neglects RPE cells as a source of VEGF.

There is evidence that both endothelial cells and pericytes respond to an elevation of glucose with at least some VEGF production and elevation of ICAM-1 as well as NF-Kβ. Pericytes are likely the earliest cells to die in diabetic retinopathy, and as they and endothelial cells die with the process of capillary occlusion, they are therefore essentially absent from the areas of peripheral ischemia. Therefore these two cell types are not likely the source of factors for the propagation of occlusion, though they certainly have a role to play in the process, especially a possible role in initiation of elevated probability of occlusion through ICAM-1 induction and also through hyperglycemia-induced angiopoietin 2-mediated apoptosis of pericytes. Angiopoietin 2 is important in the loss of pericytes and therefore in microvascular diabetic complications. It is present in elevated concentrations in the vitreous in proliferative diabetic retinopathy and is produced in the retina. VEGF was the focus of the present model because the physiology supports its relationship to ICAMs and capillary occlusion, the central point of the model, much more clearly than it does for angiopoietin 2 and more is known about it Human retinal endothelial cells, unlike endothelial cells in some animal models, do not stimulate endogenous ROS production, activation of NF-Kβ, or other pro-inflammatory changes when exposed to elevated glucose. Other cells in the retina may produce VEGF but the only cell with significant evidence of increased VEGF secretion caused by elevated glucose, and with survival in ischemic retina, is the major glial cell of the retina, the Mueller cell. Mueller cells exposed to elevated levels of glucose also produce iNOS, ICAM, cytokines, and PGE2. There is further support for these results and evidence for mediation by CaMKII-CREB. The degradation of HIF-1α is controlled by von Hippel-Lindal suppressor protein and degradation is lessened at elevated glucose levels raising VEGF through HIF-1α. Increasing levels of the transcription factor HIF-1α increases synthesis of VEGF above the base line of a non-diabetic.

Diabetes is a chronic disease and clinically observable retinal pathology is generally not present until at least several years of the condition. This means that Advanced Glycation End products (AGEs) are present and could additionally serve a role in elevating synthesis of VEGF. VEGF induction of ICAMs has been shown through AGEs in Mueller cells. Diabetes also elevates RAGE expression in Mueller cells. Although hypoxia stimulates the release of hypoxia regulated vasoproliferative factors, such as VEGF, VEGF has been found to be increased in the retinas of diabetic animals before capillary degeneration, therefore indicating that factors other than hypoxia must regulate its induction in diabetes. Additionally, VEGF is present in the retina at basal levels prior to the initiation of diabetes and is increased significantly within days of the onset of diabetes. Mueller cells survive in ischemic areas and as these areas increase in size, the total amount of VEGF synthesized would therefore increase. In conclusion, physiological support exists for a small increase in VEGF from Mueller cells in the diabetic retina prior to any ischemia. This is the permissive step in the model that discriminates the diabetic state from the non-diabetic one. This is supportive of the model only if this elevation of the substance (VEGF) above the basal state (step 1) is able to increase the probability of leukocyte adhesion to the retinal capillary endothelium.

Step 2: VEGF Raises Capillary Endothelial ICAM Increasing Leukostasis and the Probability of Capillary Occlusion.

As early as 1991, there was evidence of capillary occlusion secondary to activated granulocytes and monocytes in experimental diabetic retinopathy. VEGF was shown to increase expression of ICAM-1 in endothelial capillaries in vivo. In human diabetic retina, ICAM increases adhesion of leukocytes and monocytes to the vascular endothelium. VEGF induces retinal ICAM-1 and eNOS expression and initiates early diabetic retinal leukocyte adhesion in vivo. VEGF is produced in Mueller cells of the retina, and inhibition of Mueller cell-derived VEGF significantly decreased retinal expression of TNFα, ICAM-1 and NF-Kβ in diabetic mice. This supports VEGF being upstream to ICAM-1 and other pro-inflammatory substances, including NF-Kβ. Nitric oxide as well as inflammatory proteins, including iNOS and ICAM, cytokines, and PGE2 are produced by Mueller cells exposed to elevated levels of glucose. Diabetes has been shown to activate NF-Kβ in rodent retinas and to cause migration of the p65 subunit into nuclei of retinal endothelial cells, pericytes, ganglion cells, and cells of the inner nuclear layer (likely Mueller cells). Activation of NF-Kβ results most commonly in the translocation of p50-p65 heterodimers into the nucleus, where subsequently transcription of a variety of pro-inflammatory proteins including iNOS, ICAM, and cytokines is induced. The elevation of ICAM in the complex inflammatory state that is diabetic retinopathy is supported by several studies, and for tractability, only VEGF and its contributory role in ICAM induction is dealt with in the present model.

The process of capillary occlusion initiates when leukocytes adhere to the wall of a capillary. There are many factors related to leukocytes' mechanical properties such as increased rigidity that also likely increase leukostasis but the dominant interpretation of capillary occlusion in diabetic retinopathy is that diabetic leukocytes are much more commonly activated than those in non-diabetics. In this state they possess cell surface receptors CD18, CD11a, and CD11b that bind to ICAM-1 on the surface of retinal endothelial cells. The activation of leukocytes can be induced by elevated glucose alone. ICAM-1 is not normally present on endothelial cells but can be induced by VEGF or by other mechanisms such as an increased production of reactive oxygen species by oxidized LDL. This leukostasis in the retinal capillaries occurs quite early, within 2 weeks of diabetes onset. Thus there is strong support for VEGF promotion of ICAM expression on endothelial cells, and this results in increased probability of leukocyte adhesion to the endothelium supporting part of the model's step 2.

Leukocytes adhere to retinal vascular endothelium in diabetes and likely are instrumental in the permanent occlusion of capillaries in diabetic retinopathy. From correlative studies of retinal trypsin digests and fluorescein angiograms, it is known that as long as endothelial cells are present, capillaries are perfused and non-perfused capillaries are associated with damaged endothelial cells and empty basement membrane tubes. It is unclear how leukocytes damage retinal endothelium, as multiple overlapping mechanisms are involved. There are mechanical factors both involving the thickened basement membrane of the capillary wall, and the increased rigidity of leukocytes in diabetes. Substances released by leukocytes, including toxic oxygen metabolites and various enzymes, can cause significant 'bystander' damage. Attachment to endothelial cells strongly increases the ability of neutrophil's to produce reactive oxygen metabolites. Also, activated neutrophils from diabetic animals produce more superoxide radicals than those from non-diabetics, suggesting that leukocytes in the diabetic are both more adherent and more damaging to endothelium. Degranulated PMNs have also been observed in association with apparently dying endothelial cells. As the neutrophil contains a number of types of granules including cationic lysosomal proteins which increase vascular permeability, acid and neutral proteases which digest basement membranes, and neutrophil elastase, it is reasonable that endothelial toxicity would result. Fas levels are increased in retinas of rats that were diabetic for 2 weeks, and blocking FasL in vivo inhibited endothelial cell damage, vascular leakage, and platelet accumulation. This dependence on Fas/FasL shows the importance of apoptotic mechanisms on endothelial cell loss even in the physiological context of their exposure to leukocyte-released oxygen radicals and proteases.

Neutrophils can occlude diabetic retinal capillaries, as observed in alloxan-treated diabetic rats, which showed that local leukocyte accumulation was geographically associated with other vascular pathology such as endothelial cell damage, capillary non-perfusion, and extravascular leukocytes. White blood cells have been observed to obstruct capillaries in retinas from diabetic cats. Several studies observed acridine orange-labelled leukocytes by scanning laser ophthalmoscopy in diabetic rat retina. There was significant elevation of leukocytes trapped in the retinal microcirculation in the early stages of diabetes compared to nondiabetic rats. I has been hypothesized that accumulation of leukocytes in diabetic retinas during the pre-retinopathy stage could cause microvascular occlusions and dysfunction, causing subsequent retinopathy and these occlusions occurred early. The leukocyte occlusions observed by these experimenters seemed random without any clustering, another study observed clustered endothelial cell damage even at an early stage.

Leukocytes frequently get temporarily 'held up' at the entrance to a capillary in both normals and in diabetics because leukocytes are simply larger in diameter than most retinal capillaries (10 microns vs 6 microns). To enter the capillary requires an active cytoskeletal remodeling process to occur within the leukocyte. Also this means that flow in a capillary is temporarily blocked, but there is flow in a capillary with an intact endothelium and the capillary remains patent once the leukocyte passes through. This occurs over a generally short period of time, and in the non-diabetic, the leukocyte moves on without adhering to and damaging the endothelium by releasing ROS and enzymes or activating apoptosis. In the diabetic there can be adherence through complementary cell receptors on the activated leukocyte and the endothelium resulting in ongoing endothelial loss ultimately exceeding local endothelial replicative capacity causing an occluded, acellular capillary.

All this supports leukocyte-mediated capillary occlusion through leukocyte adhesion and endothelial cell damage with the initial step in the process of capillary occlusion being endothelial cell ICAM expression, dependent on VEGF. So step 2, the change in concentration of this substance causes some change in the retinal capillaries resulting in an increased probability of capillary occlusion above essentially zero in the non-diabetic basal state has occurred.

Step 3: Capillary Occlusion and Resultant Ischemia Further Increases VEGF Production.

Clearly capillary occlusion must produce ischemia. Oxygen is carried by patent capillaries to tissues. When the capillary becomes blocked and is no longer patent, the tissue receives no blood flow and this is the definition or at least the literal meaning of ischemia. However, there are a range of possibilities to consider. If there is dense packing of the capillaries in the network, occlusion of one could have minimal effect and all tissue could remain oxygenated. If the capillary network is extremely sparse, some cells are teetering on the edge of ischemia even before the occlusion and a large amount of tissue can become ischemic with the closure of a single capillary. The present model posits that blockage of a capillary produces tissue ischemia which upregulates a factor able to diffuse to adjacent capillaries and increase their likelihood of occlusion.

The central nervous tissue is well known for having high metabolic requirements, e.g. 25% of the oxygen utilized at rest by a human is consumed by the CNS. However, the CNS, while it upregulates oxygen consumption with activity, as shown by fMRI, has functional changes that are quite small relative to tissue like muscle. In the CNS there is no requirement for a capillary network that has density adequate to cope with temporary, extremely elevated oxygen demands. The retina, because blood absorbs or scatters light impeding optimal ocular function, is a specialized part of the CNS which has reason to minimize capillary density. Therefore it is more likely in the retina that occlusion of a capillary produces tissue ischemia. The capillary networks used in the present modelling are from actual subject imaging or from peripheral retinal capillary networks in the literature and were therefore not created for these modelling purposes. Also the oxygen diffusion coefficient was taken from the literature. Ischemia of the Mueller cell results in stabilization of HIF-1α, which is then transported to the nucleus where it is able to act as a transcription factor for VEGF, which in turn further upregulates production of VEGF. Ischemia, or hypoxia, is known to induce endothelial cell production of ICAM-1. Under hypoxic conditions, HIF-1α, VEGF, and erythropoietin levels all increase rapidly in the inner retina, especially in the central region of the inner nuclear layer, the location of Mueller cell nuclei. If HIF-1α is disrupted in Mueller cells there is attenuation of the increased leakage and adhesion of leukocytes as well as decreased VEGF and ICAM. Also, Mueller cells survive in the ischemic retina of diabetics. Step 3, that capillary occlusion results in local retinal ischemia and by some mechanism further elevates the level of the substance (VEGF) and also that ischemia does not act to kill the cells producing the substance, is well supported.

Step 4: Elevated Concentration of the Substance in a Local Area Increases the Probability of Occlusion of Nearby Capillaries Resulting in the Spatial Propagation of Capillary Occlusion.

The model posits that once a capillary is permanently occluded, the probability of a nearby capillary occluding increases. Once this irreversible capillary occlusion is initiated by an activated leukocyte adhesion, a local area of retina composed of Mueller cells and other retinal tissue has a drop in its oxygen tension. Within the Mueller cell HIF-1α is stabilized, migrates to the nucleus as a transcription factor, and further increases the production of VEGF. This elevated level of VEGF diffuses to surrounding tissues, including capillary endothelium, and in those adjacent capillaries further increases local VEGF and ICAM-1 (step 2), with a resulting increase in the likelihood of occlusion. There is evidence supportive of this process. In spontaneously diabetic monkey retinas, neutrophils are detected adjacent to areas with capillary closure. This spatially-selective concentration of adherent neutrophils means local endothelial adhesion must be elevated and though there is no specific immunohistological evidence of locally elevated ICAMs secondary to locally elevated VEGF, this is reasonable. Earlier work in human diabetics found relatively large areas containing only cell-free capillaries and the margins of such fields were generally studded with microaneurysms, proliferated endothelial cells, and irregularities in the contours of venous walls Also in humans, increased numbers of adherent PMNs within retinal capillaries are observed adjacent to sites of capillary non-perfusion or degeneration. All this is consistent with locally elevated VEGF generated in the ischemic retinal areas, diffusing to affect surrounding retinal capillaries in both an ischemic way, by increasing leukocyte adhesion, and in an angiogenic way, by causing local vasoproliferative-type changes.

The most relevant animal model is that of spontaneous diabetes in a primate. The earliest histologically documented changes observed were dot/blot hemorrhages, cotton-wool spots (cotton-wool spots are non-perfused nerve fiber layer areas), and small non-perfused retinal areas. Microaneurysms, often associated with small intraretinal microvascular abnormalities (IRMAs), were located adjacent to areas of nonperfusion, shown by lack of ADPase positive blood vessels. Large areas of capillary loss always involved arteriolar pruning. These observations are consistent with the hypothesis that the driver of ischemic retinopathy is the development of small ischemic areas which then propagate locally. The arteriolar pruning would occur as vascular branches both decrease their flow due to loss of capillaries, and are then subjected to higher VEGF levels. The microaneurysms and IRMA represent canonical angiogenic consequences of VEGF, elevated at the edge of the ischemic areas. Over the disease course, large ischemic areas occur, meaning that generally the microaneurysms and IRMA occur later in the disease process. Within this framework a large retinal vessel, by creating a surrounding oxygenated zone, may act as a barrier to propagation of capillary loss. This can be seen both in clinical angiograms and in histology. Similarly, in induced or spontaneous diabetes in monkeys, early background retinopathy was characterized by capillary dropout and IRMAs. As is commonly experienced in humans, no clinical sign of diabetic retinopathy was detected in monkeys with spontaneous or STZ-induce diabetes for 4 to 13 years provided the monkeys were not also hypertensive. Though there is no existing data on local VEGF and ICAM levels as a function of distance from an area of retinal ischemia, fairly strong observational support is present in the literature that is consistent with step 4, the spatial propagation of capillary occlusion.

There are a several types of in vivo experiments which either examine the results of injection of VEGF into animal eyes or the results of variation in the level of VEGF in animal models. VEGF is considered to be a pro-inflammatory molecule whose vitreal levels are highly correlated with retinal neovascularization and edema. In mice, even a temporary increase in VEGF expression in photoreceptors, without elevated glucose, demonstrated retinal vascular changes similar to diabetic retinopathy, including retinal leukostasis, capillary endothelial cell and pericyte loss, and acellular capillaries. There are also animal diabetic models in which an intervention, ranging from oral or intravitreal pharmaceuticals or genetic manipulation are able to prevent the development of diabetic retinal vascular changes. To the best of the inventor's knowledge, though acting by quite different pathways, and some without altering VEGF, all prevent the adhesion of leukocytes to the retinal endothelium thereby preventing development of retinal capillary occlusion and attenuating signs of diabetic retinopathy. Thus, the occlusion process seems essential to diabetic retinopathy and this model will behave in the same way since the elevation of capillary occlusion probability is essential to development and propagation of ischemia. A number of interesting results were obtained using a conditional Mueller cell VEGF knock out model (CVKO). The levels of pro-inflammatory markers in CVKO mice were examined by IB analysis for intercellular adhesion molecule-1 (ICAM1) and tumor necrosis factor-α (TNFα), 2 months after STZ injection. Compared with controls, the CVKO mice showed 62.3% and 52.9% reduction of ICAM1 and TNFα respectively, and showed a 75.0% reduction of adherent leukocytes, a cardinal feature of retinal inflammation in DR.

Direct exposure of the retina to VEGF at levels comparable to those found in patients with diabetic neovascularization also supports this hypothesis. Just 9 days post uni-ocular VEGF injection in monkeys, the intraluminal volume of capillaries in the deep retinal plexus was decreased by 5+ fold due to capillary endothelial cell hypertrophy as measured by both EM and light microscopy. This suggests a preferential occlusion of these capillaries of the inner nuclear layer which are adjacent to Mueller cell bodies. An acute exposure to VEGF results in endothelial cell hypertrophy sufficient to prevent flow in these capillaries which were only about 6 microns in lumen diameter prior to the 5 fold swelling. It was not shown in the study but capillary occlusion and retinal ischemia would be expected. A classic study examined VEGF injections over a longer period of time. In the study, animals received from 1 to 26 injections of VEGF. Even a single injection yielded large vessel dilation, tortuosity, and vascular leakage, all canonical changes seen with elevated VEGF. After 6 injections (one every 3 days) in one animal, venous beading is visible and areas of non-perfusion were present in the midperiphery. In another animal after 4 injections, large areas of capillary closure appeared. Neovascularization of the disk appears much later (80 days) and associated with "extensive areas of avascular retina temporally". The inventors anticipate the adverse positive feedback hypothesis of the present (without any geographic dependence or modelling) in this quote "These data show that VEGF alone can trigger retinal ischemia through capillary closure in normotensive eyes. This activity could initiate a positive feedback loop, further increasing VEGF levels" (Tolentino et al., Opthamology. 1996; 103(11):1820-8). In summary, the molecule VEGF is a reasonable candidate for a one-molecule model of the progression of the diabetic capillary occlusive process, even if its actions are often through other molecules, e.g. ICAMs, or complex processes, e.g. leukostasis and capillary occlusion.

Model Considerations

Figure 12:
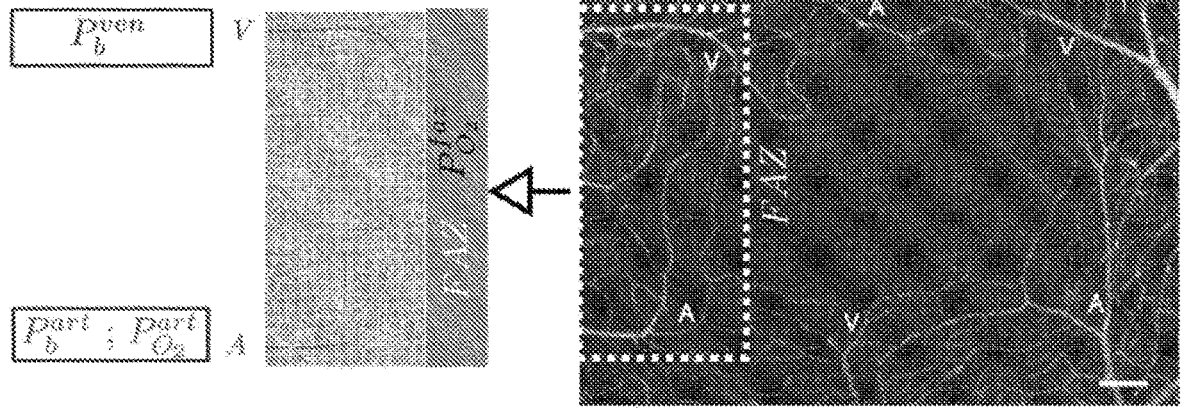
FIG. 12 depicts exemplary model abstraction and construction of human perifoveal capillary network from an Adaptive Optics Scanning Laser Ophthalmology (AOSLO) image. Diameter of the FAZ in this ASOLO image is approximately 500 microns. The scale bar is 100 microns.

To capture the events of progressive capillary occlusion, a quantitative model of the anatomical features mentioned above were implemented in CompuCell3D. As depicted in FIG. 12, beginning with an AOSLO scan of the perivascular fovea, a full vascular model from an arteriole to a venule with the linking capillaries is included with oxygen advection, oxygen diffusion, and oxygen consumption. Referring to FIG. 12, on the right, an AOSLO image shows juxtafoveal capillaries adjacent to the foveal avascular zone (FAZ). This is a normal capillary map in a patient without diabetes. On the left, a model schematic shows the reconstruction of the capillary network framed in the AOSLO image with cells filling in empty space between vessels uniformly. Capillary network has arteriole (A) and venule (V) termini marked. Boundary blood pressures are assigned for A and V termini Boundary oxygen tensions are assigned for A terminus and for FAZ whereas venous oxygen tension is model dependent. Model objects in red, green, brown are capillary blocks (CAP), Mueller cells (MC) and other retinal cells (OT) respectively. Yellow pixels surrounding objects are object borders, which are muted in other figures of the manuscript. Note that this example shows a macular capillary network from a different subject than that shown in CASE 1. Diameter of the FAZ in this ASOLO image is approximately 500 microns. The scale bar is 100 microns.

The present example develops a conceptually simple model of the diabetic retina treating Mueller cells as the sole retinal source of VEGF and assumes a slight elevation of VEGF production by Mueller cells in a diabetic retina higher than that in the normal retina. Physiologically, VEGF is a necessary neurotrophic factor in the retina and is normally present at low levels. In the present model, VEGF is produced by Mueller cells locally in variable amounts based on oxygen saturation. VEGF diffuses from the Mueller cells and is consumed by cells including endothelial cells, but is not transported away by advection. The model vessels have endothelial cells which respond to local VEGF levels by an increased probability of occlusion with elevation of local VEGF and also by leaking if local VEGF exceeds a threshold level. The model is cycled many times, and if a capillary occlusion occurs, all flow rates, steady state oxygen tension and VEGF levels are recalculated.

The model's treatment of occlusion is an irreversible decrease of capillary diameter to zero. An important assumption is that the vascular supply to each area of retina is critical in that occlusion of a capillary will result in ischemia of an area of physiologically-dependent retina with a resultant elevation of VEGF synthesis by the locally ischemic Mueller cells. It is not known whether this has been proven, but the constraints imposed by evolution on the visual apparatus make this assumption reasonable. "It is likely that retinal capillary networks are morphometrically adapted in order that the balance between cellular nutrition and optical clarity can be achieved" (Chan et al., Investigative Opthalmology & Visual Science. 2012; 53(9):5502-14). Note, however, that with the variations of capillary spacing seen anatomically, all areas of retina would not have equal dependence on a single supplying capillary. In a network based on actual capillary anatomy, different areas of retina could be more or less critical as a result of variation in local capillary density. There would thus be greater or lesser propagation of capillary closure by the adverse feedback mechanism Small capillary diameter adjustments can also occur, e.g. slightly increasing diameter with increased flow after each capillary occlusion. Maps at various model times are made of capillary network structure, flow, oxygen tensions, VEGF, and retinal edema. These are the output measures as well as summary graphs of the system such as total flow and average distance from an intact capillary.

Model capillary occlusions are always probabilistic based on local VEGF levels and the calculated flows of the capillary segments. Capillary networks of several types were utilized including physiologically-unlikely hexagonal capillary network with introduced deletions, physiologically realistic peripheral retinal 'ladder' capillaries, and an actual perifoveal arteriovenous sector capillary map obtained from adaptive optics scanning laser ophthalmoscopy (AOSLO) imaging of a subject. The hexagonal map was used to explore the dependence of capillary occlusion progression on amount of tissue dependent on capillaries by varying the scale of the hexagons. Both the macula and the peripheral retina are clinically important, with the macular area being the location of ischemia as well as macular edema affecting visual acuity, and the periphery being the major source of the ischemia and resultant VEGF production which results in retinal neovascularization.

The present example primarily addresses a sector of the perifoveal capillary network from AOSLO imaging (CASE 1) and filled the open space between vessel segments with cells of anatomically reasonable sizes (Tables 1-3). Capillary diameters were estimated based on the AOSLO image. Model inputs such as terminal hydrostatic pressure and arteriolar blood oxygen tension were estimated from published results (Tables 1-3). Vascular flows, oxygen and VEGF fluxes were calculated and resulting tissue oxygen tension and VEGF levels were determined in the model. A large number (362) of replicate runs were made of the subject's capillary network in order to assess the vulnerability of distinct capillaries given the probabilistic nature of the model of individual capillary occlusion. The Detailed Description of the Model section below details mathematical descriptions, parameter selection and influence and boundary and initial conditions of the present model.

TABLE 1

Model Parameters—Module Parameters

Figure 27:
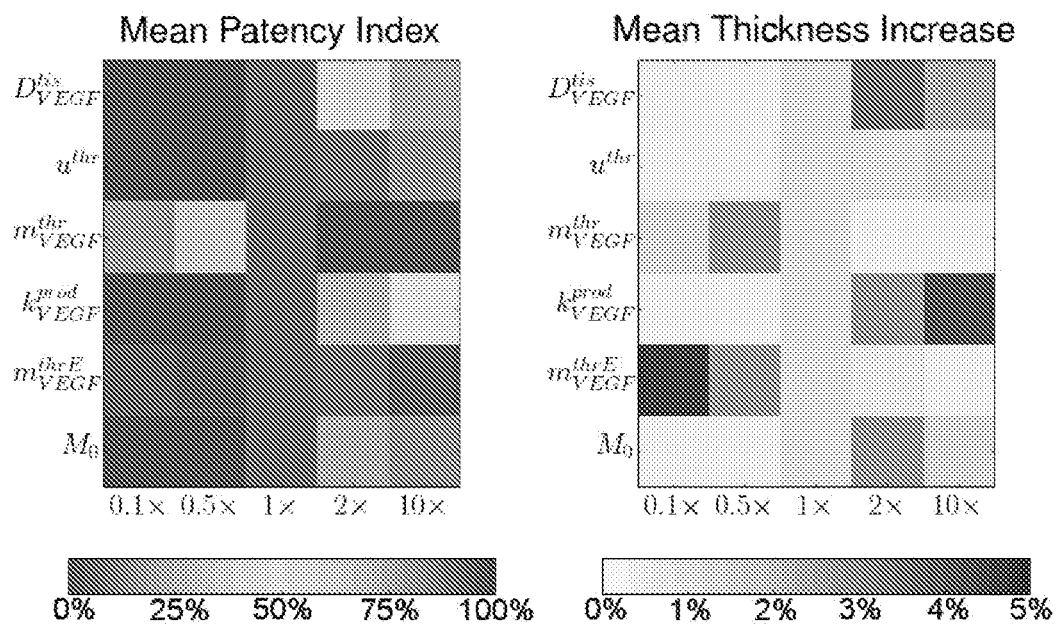
FIG. 27 depicts parameter influence on capillary network patency index and retinal thickness change in CASE 1 simulation. Variations of six parameters one-at-a-time (listed vertically beside figure) at four widely varying values (listed horizontally below figure) are run on replicate simulations. Each colored block represents the average result of 28 simulations with a certain-value variation of a certain parameter from reference parameter set as in CASE 1. The CASE 1 parameter set used in the modelling in this paper is denoted as "×1" in the figure.

| Module | Parameter | Value | Meaning | Source |
|---|---|---|---|---|
| Oxygen Flux | $D_{O_2}^{pl}$ | $2.77 \times 10^{-5}$ cm$^2$/s | Diffusion coefficient of oxygen in blood plasma | [1] |
| | $D_{O_2}^{tis}$ | $1.04 \times 10^{-5}$ cm$^2$/s | Diffusion coefficient of oxygen in tissue | [1] |
| | $\alpha$ | $3 \times 10^{-5}$ ml O$_2$/(cm$^3$ · m) | Solubility of oxygen in blood and tissue | [1] |
| | $M_0$ | $2 \times 10^{-4}$ ml O$_2$/(cm$^3$ · s) | Maximum metabolic rate of oxygen in Müller cells and other retinal cells | [1] |
| | $P_{O_2 o}$ | 1 mmHg | Oxygen tension when metabolic rate of Müller cells reach half of maximum value | [1] |
| | $P_{O_2}^{hyp}$ | 4 mmHg | Critical oxygen tension when Mueller cells switch between normal and hypoxic state | Selected so no cells are hypoxic under normal conditions |
| | $P_{O_2}^{art}$ | 45 mmHg* | Oxygen tension in the inflow blood | Estimate based on [2] |
| | $P_{O_2}^{faz}$ | 45 mmHg | Oxygen tension at foveal avascular zone | Estimate based on [2] |
| VEGF Flux | $D_{VEGF}^{tis}$ | $5 \times 10^{-6}$ cm$^2$/s | Diffusion coefficient of VEGF in tissue | [3] |
| | $k_{VEGF}^{dec}$ | $2.8 \times 10^{-4}$ 1/s | Decay rate of VEGF | [4] |
| | $k_{VEGF}^{prod}$ | 10 1/s | Maximum synthesis rate of VEGF in Muller cells | Assumed, see FIG. 27 heat map |
| | $m_{VEGF}^{max}$ | 1 (arbitrary unit) | Capacity of VEGF synthesis in Muller cells | Assumed, feedback loop |
| Network Flow | $P_b^{art}$ | 25 mmHg** | Arteriolar pressure | Chosen to be within experimental physiological ranges reported by [5] (15-32 mmHg) and [6] (11.3-26.3 mmHg) |
| | $P_b^{ven}$ | 20 mmHg*** | Venular pressure | Chosen to be slightly above mean intraocular pressure of 15 mmHg [6] |
| | $\eta_{pl}$ | 1.05 cP | Viscosity of blood plasma | [1] |
| Occlusion | $m_{VEGF}^{thr}$ | 0.5 (arbitrary unit) | Critical VEGF level to induce occlusion | Assumed, see FIG. 27 heat map |
| | $u^{thr}$ | 100 µm/s | Critical blood flow velocity to induce occlusion | Assumed, see FIG. 27, heat map |

TABLE 1-continued

Model Parameters—Module Parameters

| Module | Parameter | Value | Meaning | Source |
|---|---|---|---|---|
| Edema formation | $m_{VEGF}^{thrE}$ | 0.01 (arbitrary unit) | VEGF threshold to trigger formation of edema | Assumed, see FIG. 27 heat map |

*Lower oxygen tension (40 mmHg) was assumed for peripheral simulation.
**Lower arterial pressure (23 mmHg) was assumed for peripheral simulation.
***Higher venular pressure (22 mmHg) was assumed for peripheral simulation.
[1] Reglin et al., Am J Physiol Heart Circ Physiol. 2009; 297(6):H2206-19\
[2] Lau & Linsenmeir, Experimental eye research. 2012; 102:50-8.
[3] Aubert et al., Bull Math Biol. 2011; 73(10):2430-51.
[4] Shirinifard et al., PLoS Comput Biol. 2012; 8(5):e1002440.
[5] Landis & Pappenheimer, American Physiological Society; 1963. p. 961-1034.
[6] Gooding et al., Diabetologia. 2010; 53(9):2029-35.

TABLE 2

Model Parameters—Geometrical Parameters

| Topology | Parameter | Value | Meaning | Source |
|---|---|---|---|---|
| All | µm per px | 2 µm/pixel | Unit conversion from pixel to micron | Selected to balance spatial resolution with computational cost |
| All | $a^{MC}$ | 24 µm | Typical size of Mueller cells | Anatomically reasonable [7] |
| All | $a^{OT}$ | 20 µm | Typical size of other retinal cells | Anatomically reasonable [7] |
| All | $vol^{FP}$ | 3200 µm³ | Volume of fluid portion extracted in total from leaky capillary during $\Delta t_e$ | Assumed, because of lack of clinical data on rate of edema formation |
| Peri-foveal | $x^{dim}$ | 510 µm | Dimension in $\vec{x}$ direction | Measured from ASOLO image |
| | $y^{dim}$ | 600 µm | Dimension in $\vec{y}$ direction | Measured from ASOLO image |
| | $z^{dim}$ | 50 µm | Dimension in $\vec{z}$ direction | Selected to contain tissue layer of interest while excluding additional tissue layers |
| | $d^{art}$ | 9 µm | Diameter of arterole | Measured from ASOLO image |
| | $d^{ven}$ | 10 µm | Diameter of venule | Measured from ASOLO image |
| | $d^{cap}$ | 5 µm | Average diameter of capillary | Measured from ASOLO image |
| Peripheral | $x^{dim}$ | 900 µm | Dimension in $\vec{x}$ direction | From [8] |
| | $y^{dim}$ | 460 µm | Dimension in $\vec{y}$ direction | From [8] |
| | $z^{dim}$ | 50 µm | Dimension in $\vec{z}$ direction | Selected to contain tissue layer of interest while excluding additional tissue layers |
| | $d^{art}$ | 25 µm | Diameter of arteriole | From [8] |
| | $d^{ven}$ | 30 µm | Diameter of venule | From [8] |
| | $d^{shunt}$ | 18 µm | Diameter of shunt | From [8] |
| | $d^{cap}$ | 10 µm | Average diameter of capillary | From [8] |
| Hexagonal | $x^{dim}$ | 510 µm | Dimension in $\vec{x}$ direction | Measured from ASOLO image |
| | $y^{dim}$ | 600 µm | Dimension in $\vec{y}$ direction | Measured from ASOLO image |
| | $z^{dim}$ | 50 µm | Dimension in $\vec{z}$ direction | Selected to contain tissue layer of interest while excluding additional tissue layers |
| | $d^{art}$ | 9 µm | Diameter of arteriole | Measured from ASOLO image |
| | $d^{ven}$ | 10 µm | Diameter of venule | Measured from ASOLO image |
| | $d^{cap}$ | 5 µm | Average diameter of capillary | Measured from ASOLO image |

[7] Reichenbach & Bringmann, Mueller cells in the healthy and diseased retina. New York: Springer 2010. 415 p.
[8] Spitznas & Bornfeld, Albrecht Von Graefes Arch Klin Exp Ophthalmol 1977; 203(3-4):217-29.

TABLE 3

Model Parameters—Temporal Parameters

| Parameter | Value | Meaning | Source |
|---|---|---|---|
| sec per MCS | 86400 s/MCS | Unit conversion from Monte Carlo step to second | Selected, see Parameter selection section |
| $\Delta t_o$ | 4 weeks | Minimal time difference between two continuous capillary occlusion steps | Selected, see Parameter selection section |
| $\Delta t_e$ | 1 week | Minimal time difference between two continuous edema formation steps | Selected, see Parameter selection section |
| $\Delta t_f$ | 0.002 s | Time step for simulating modules of field fluxes | Selected for proper numerical integration |

Many models have been constructed to study problems at the interface of vasculature in various tissues: skeletal muscle, brain, vascular tumor, and retina. Shirinifard et al. (PLoS Comput. Biol. 2012; 8(5):e1002440) employed a 3D multi-cell model to successfully recapitulate the three patterns of progression of age-related macular degeneration and suggested that defects in adhesion were the dominant contributor to initiation and development of choroidal neovascularization. Cringle et al. (Comp. Biochem. Physiol. A Mol. Integr. Physiol. 2002; 132(1):61-6; and Investigative Ophthalmology & Visual Science. 2002; 43(6):1922-7.) divide retina into multiple layers and used a mathematical model to calculate the oxygen tension in each layer in terms of oxygen consumption rate in that layer and the oxygen level in choroidal capillaries. McDougall et al. (Bull Math Biol. 2012; 74(10):2272-314) studied angiogenesis during normal retinal development using a hybrid discrete-continuum mathematical model and computationally simulated the structure of a retinal vascular plexus that agreed with the whole-mount retinal vasculatures at different stages of development. The present model deals with a different pathophysiological issue: progression of ischemia and edema in diabetic retinopathy based on a local VEGF-dependent mechanism of propagation of capillary occlusions. Unlike the present study, Gandica et al. (PLoS One. 2014; 9(11):e113165) developed a computational model of retinal ischemia studying the effect of critical sizes and densities of localized blockages of retinal vasculature on the emergence of diabetic retinopathy. In the Gandica et al. model, various sizes of local blockages of vessels, assumedly caused by destabilizing proteins such as Angiopoietin-2, were randomly distributed in the region of interest and areas of derived hypoxia were examined regarded as an indicator of potential phenotypes of diabetic retinopathy. An important conclusion in their study is that local blockages with smaller size than characteristic irrigation length, if their densities exceed a critical threshold, likely result in large hypoxic areas because of a cooperating effect. A limitation of the model, as the authors also noted, is the simplified consideration of oxygen transport.

To ensure that the specific geometry of the retinal capillary network was respected, vascular networks from actual subject imaging or from peripheral retinal capillary networks in the literature were used, and were not created for these modelling purposes. Also, the oxygen diffusion coefficient was taken from the literature.

Model Description

This study explored the effect of focal capillary occlusion on decreasing local oxygenation of retinal cells, resultant elevation in VEGF, and the consequences in terms of propagation of capillary occlusions and formation of edema using a computational model. The anatomy of this capillary network was determined from a normal patient using AOSLO (FIG. 12). This network is an arteriovenous sector with the capillaries connecting the arteriole and venule, the foveal avascular zone on one edge and retinal tissue on the other borders. The network was computationally reconstructed, and simulation was initialized with boundary blood pressures and arterial and FAZ oxygen tension (FIG. 12). The major entering arterial node and the exiting venous node are assigned with blood pressures $P_b^{art}$ and $P_b^{ven}$ respectively. These pressures would not be expected to depend on the diabetic state and remain fixed. Other boundary nodes are assigned with blood pressures of intermediate values (see boundary conditions and initial state of simulation described in the Detailed Description of the Model section below). The FAZ region is treated as an oxygen source, supplied by choroidal capillaries. The entering arterial node and the FAZ region are assigned with oxygen tension $P_{O_2}^{art}$ and $P_{O_2}^{faz}$ though the exiting venous oxygen tension is model dependent. Other boundary nodes with incoming blood flow are assigned with oxygen tensions of smaller values. Hypoxia-induced elevated secretion of VEGF in Mueller cells is known as an occurrence in diabetic retinopathy. FAZ region is treated as a sink for VEGF. The oxygenation and local VEGF levels were modeled within this retinal sector following a focal capillary obstruction. Within the sector of capillary network modeled, the arterial side receives oxygen-rich blood, while from the venous terminus carries away blood with lower oxygen tension. Oxygen diffuses into tissue space from capillaries, where it is consumed and metabolized by retinal cells. Hypoxia of local retinal tissue is induced by a local capillary segment occlusion, and production of local VEGF, dependent on the level of hypoxia is upregulated in ischemic Mueller cells. VEGF released by Mueller cells diffuses to other nearby patent capillary segments, which probabilistically derive more occlusions based on an underlying and not visibly modelled upregulation of ICAM and increased probability of leukostasis. The schematic of oxygen and VEGF fluxes is depicted in FIG. 13.

Figure 13:
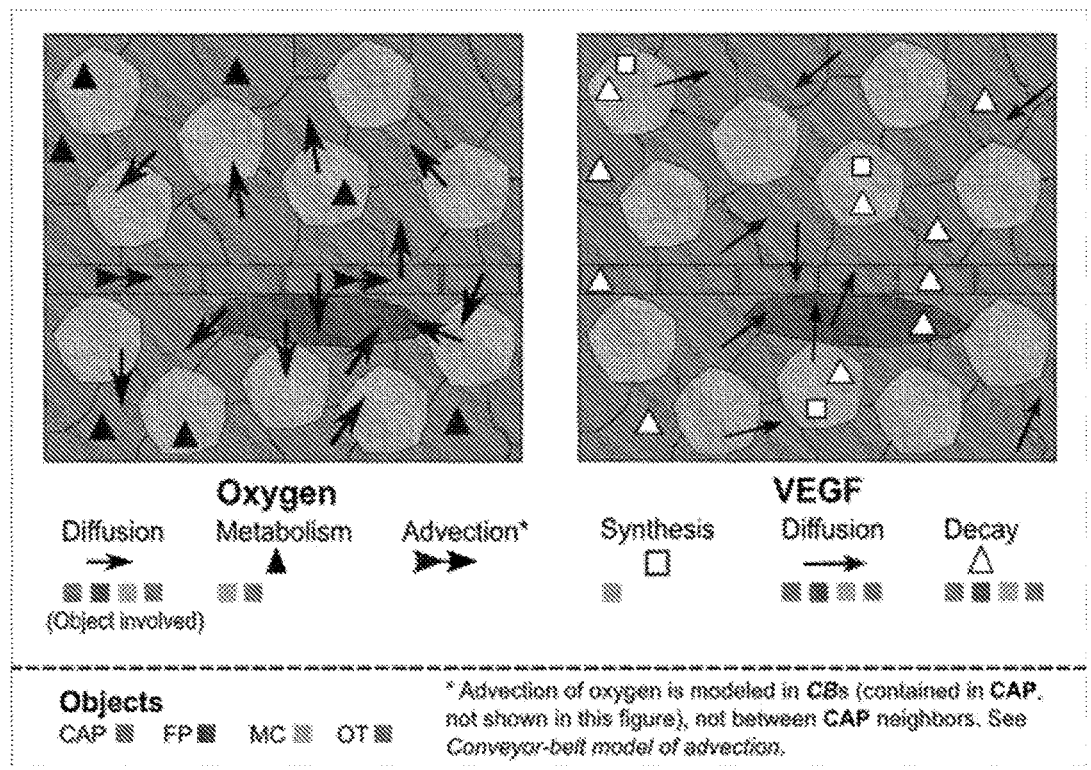
FIG. 13 depicts a schematic of oxygen and VEGF fluxes. Colored blocks represent model objects: Capillary block (CAP in red), Fluid portion (FP in cyan), Mueller cell (MC in green) and Other retinal cells (OT in brown). Markers in the form arrows, triangles and squares are used to represent modeled fluxes.

Referring to FIG. 13, colored blocks represent model objects: Capillary block (CAP in red), Fluid portion (FP in cyan), Mueller cell (MC in green) and Other retinal cells (OT in brown). Markers in the form arrows, triangles and squares are used to represent modeled fluxes. On the left are the oxygen fluxes including advection, diffusion and metabolism. Oxygen advection is modeled for object CB. Oxygen diffusion is modeled for object pairs among CAP, MC, OT and FP. Oxygen metabolism is modeled only for objects MC and OT. On the right are the VEGF fluxes including synthesis, diffusion and decay. VEGF synthesis is modeled for object MC again as the model's only VEGF source. VEGF diffusion is modeled for object pairs among CAP, MC, OT and FP. VEGF decay is modeled for objects CAP, MC, OT and FP. The arrangement of model objects do not necessarily reflect detailed configurations constructed in the simulations.

Model Objects and Processes

The described computational model consists of four generalized model cell types: capillary block (CAP), fluid portion (FP), Mueller cell (MC) and other retinal cell (OT). Along with these four generalized cell types in the model is another model object called the conveyor-belt block, CB, which is an object associated with the capillary block and introduced for modeling of oxygen advection. In addition to five model objects, two chemical fields exist in the model: oxygen and VEGF. Modeled processes include advection of blood carrying oxygen, diffusion and metabolism of oxygen, and synthesis, diffusion and decay of VEGF. As detailed in the Detailed Description of the Model section below and summarized in Table 4, model objects have the following properties and are representative of various retinal cells:

CAP is the structural element of the capillary segment. CAP functionally represents a capillary segment with endothelium and blood within the capillary lumen. CAP is involved in modules of oxygen diffusion and VEGF diffusion and decay. CAP has three states: "normal", "leaky" and "occluded". "Normal" CAP can transition to "leaky" state if local VEGF level is greater than a threshold value. Both "normal" and "leaky" CAPs can transition to an "occluded" state if the occlusion condition, whose probability is raised by an elevated VEGF level and lowered by elevated blood flow velocity, is met (Table 5). Once one CAP becomes "occluded", the flow of that capillary segment from node to node is set to zero. Also, "Occluded" is a permanent or irreversible state for the CAP. (More details on capillary occlusion in the Detailed Description of the Model section below);

FP is the structural element of and represents incremental volume of retinal edema, cystic areas of fluid within the retina. FP represents fluid leaked from a CAP while it is in the leaky state. FP is modeled as a "cell"-like object that is well-trapped by surrounding objects. FP is involved in modules of oxygen diffusion and VEGF diffusion and decay. (More details on edema formation in the Detailed Description of the Model section below);

MC is involved in modules of oxygen diffusion and metabolism and VEGF synthesis, diffusion and decay. The MC has two states: "normal" and "hypoxic". The "Normal" MC can reversibly transition to a "hypoxic" state synthesizing VEGF only when cellular oxygen tension is below a threshold value. In the model only the "hypoxic" MC has the capability of synthesizing VEGF though in the diabetic retina a number of other cells have at least some ability to synthesize VEGF;

OT broadly includes all other retinal cells other than Mueller cells, i.e. the neural retina including astrocytes and microglia but excluding photoreceptors supplied with oxygen from the choriocapillaris. OT is involved in modules of oxygen diffusion and metabolism and VEGF diffusion and decay; and CB is a functional element created in the model to "convey" oxygen along a linear pipe, thus CB or conveyor belt is not an anatomical element corresponding to a retinal structure but is a model device allowing mathematically convenient modelling of oxygen advection. CB is involved in the module of oxygen advection. Each CB is associated with a "host" CAP, which usually contains more than one CB. In contrast to the fixed pre-defined size of CAP on every capillary segment, size of CB is proportional to the blood flow velocity on its host capillary segment.

TABLE 4

Properties and Behaviors of Model Objects

| Objects | | | |
| --- | --- | --- | --- |
| Generalized Cell | Other | Properties | Behaviors |
| Capillary Block (CAP) | | (1) CAP is a structural unit of each capillary segment between two junctions. Each CAP represents a composite of endothelium and blood. CAP has a cylindrical shape, with diameter given by $d^{cap}$, (2) Each CAP has more than one affiliated CBs. | (1) CAP transfers $O_2$ into MC, OT and FP in contact with it. (2) CAP uptakes VEGF from OT and FP in contact. A CAP can become leaky or occluded in the presence of high level of VEGF, if the conditions are met respectively. (3) CAP destructs VEGF. |
| Mueller cell (MC) | | (1) MC doesn't have a defined shape initially; each MC has a 1-voxel-size CC3D seed to grow from, (2) MC has typical size of $a^{MC}$. | (1) MC transfers and metabolizes $O_2$. When cellular store of $O_2$ drops below a critical value, MC becomes hypoxic. (2) MC produces and releases VEGF in an $O_2$ tension-dependent manner. (3) MC transfers and destructs VEGF. |
| Other retinal cell (OT) | | (1) OT doesn't have a defined shape initially; each OT has a 1-voxel-size CC3D seed to grow from. (2) OT has typical size of $a^{OT}$. | (1) OT transfers and metabolizes $O_2$. (2) OT transfers and destructs VEGF. |
| Fluid portion (FP) | | (1 FP doesn't have defined shape initially; however, each FP has a 1-voxel-size CC3D seed to grow from beside a leaky CAP. (2) FP has typical volume of $vol^{FP}$. | (1) FP transfers $O_2$. (2) FP transfers and destructs VEGF. (3) FP is created close to a leaky CAP (4) FP in contact with bottom surface of the system shrinks with time, representing RPE's capability of pumping away leaked fluid. |

TABLE 4-continued

Properties and Behaviors of Model Objects

| Objects | | | |
|---|---|---|---|
| Generalized Cell | Other | Properties | Behaviors |
| | Conveyor-belt Block (CB) | (1) CB is a functional unit for oxygen advection, which conceptually represented block of blood containing $O_2$ within a host CAP.<br>(2) CB has a cylindrical shape, with diameter identical to its host CAP and length proportional to local blood flow velocity. A certain capillary segment contains CBs of equal length. Different vessels have CB of different lengths proportional to flow velocity. | (1) A CB conveys $O_2$ to its downstream counterpart, representing advection, |

TABLE 5

State Transition of Model Objects

| Objects | State transition | Condition |
|---|---|---|
| Mueller cell (MC) | normal $\xrightarrow{P_{O_2}^{(i)}}$ hypoxic | $P_{O_2}^{(i)} < P_{O_2}^{hyp}$ |
| | hypoxic $\xrightarrow{P_{O_2}^{(i)}}$ normal | $P_{O_2}^{(i)} > P_{O_2}^{hyp}$ |
| Capillary Block (CAP) | $\begin{cases} normal \\ leaky \end{cases} \xrightarrow{vol^{(i)} \cdot c_{VEGF}^{(i)}, u_{kl}}$ occluded | $p_{occ}^{(i)} > \varepsilon$<br>where $p_{occ}^{(i)} = \dfrac{vol^{(i)} \cdot v_{VEGF}^{(i)}}{m_{VEGF}^{thr} + vol^{(i)} \cdot c_{VEGF}^{(i)}} \cdot \dfrac{(u^{thr})^2}{(u^{thr})^2 + (u^{kl})^2}$,<br>$\varepsilon$ is a random number in (0, 1)<br>and kl is a certain capillary segment. |
| | normal $\xrightarrow{vol^{(i)} \cdot c_{VEGF}^{(i)}, u_{kl}}$ leaky | $vol^{(i)} \cdot c_{VEGF}^{(i)} > m_{VEGF}^{thrE}$ |

1. The superscript or subscript without ( ) or [ ] such as kl represents a capillary segment or topological edge between junction k and junction l. It's primarily used in the calculation of network flow.
2. The superscript or subscript with ( ) such as (i) represents ids of objects MC, OT, CAP and FP. Each of these objects has unique id. When (i) and (j) pair up, it stands for a quantity between two object neighbors such as common surface area or distance between centers. It's used in the simulation of oxygen and VEGF fluxes, except oxygen advection.

Figure 14:
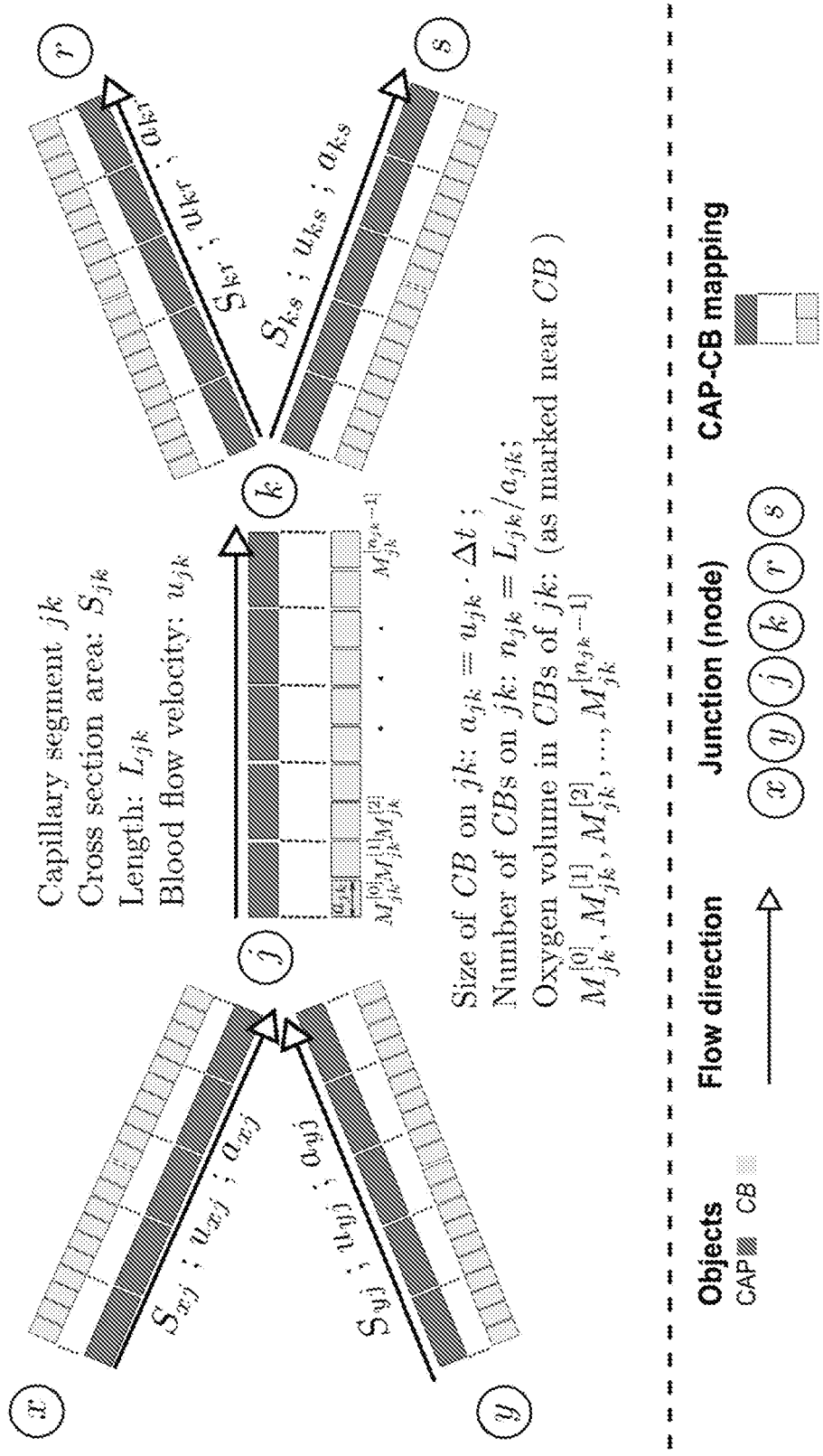
FIG. 14 depicts a schematic of the conveyor-belt model of oxygen advection. The schematic shows a small capillary network with five segments and two junctions. Along the blood flow direction, marked as arrow with empty triangular head, the first junction has merging blood flow and the second branching blood flow. Blocks in red are CAPs, building blocks, or structural elements (visually present in model configuration), of capillary segments. Blocks in yellow are CBs, functional elements for advection.

To model oxygen advection, each capillary segment was discretized into a one-dimensional sequence of equally-sized CBs and simulate oxygen advection using a "conveying" action, which moves a volume of oxygen in a given CB to its next downstream connected CB (FIG. 14). Referring to FIG. 14, of a CAP is fixed throughout a simulation, so each capillary segment has fixed number of CAPs. In contrast, the size of a CB is always proportional to flow velocity on the capillary segment, so flow velocity and accordingly the number of CBs on a patent capillary segment can vary following an occlusion elsewhere as flows in the network are adjusted to the changed network resistance structure. During each time step of advection, a CB passes its oxygen volume to the next CB. Importantly, the size of a CB is equal to flow velocity of host capillary segment multiplied by time step of advection, which means the "conveying" speed of oxygen from one CB to next is exactly equivalent to the flow velocity in that capillary segment. At a merging junction, the upstream capillary segments add the oxygen volumes in their last CBs and pass the total to the first CB of the downstream capillary segment. At a branching junction, the parent capillary segment distributes the oxygen volume in its last CB into the first CBs of the daughter segments according to conservation of blood flow volume. Mathematical descriptions were detailed as equations (9)-(11) in the Detailed Description of the Model section. Each CB is associated with, or mapped to, a host CAP. The modules of advection (involving CBs) and diffusion (involving CAPs) are connected with processes that convert oxygen volumes between the host CAP and its associated CBs. (see FIG. 15).

Figure 15:
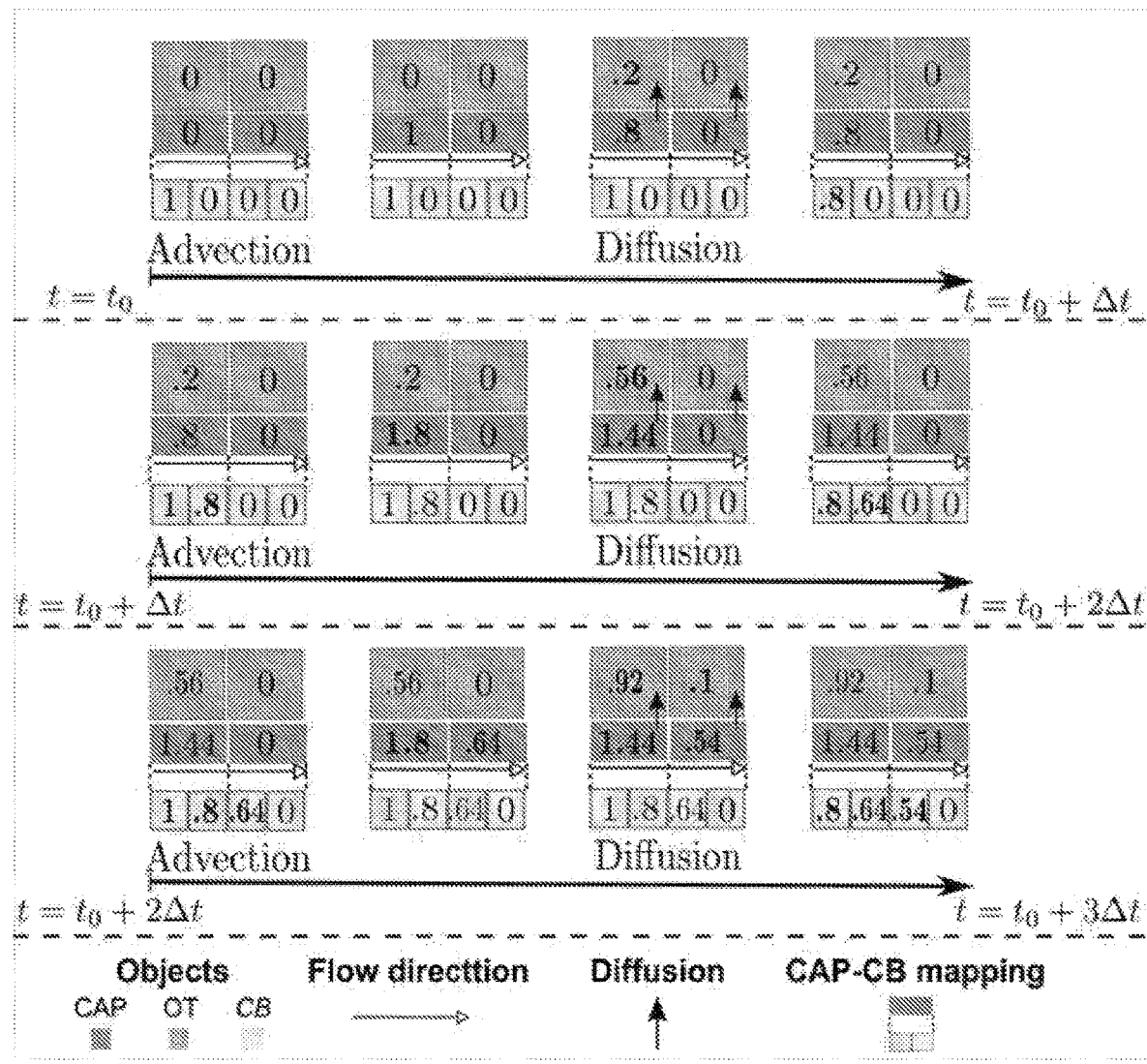
FIG. 15 depicts a schematic of an example of the procedure of sequential simulation of advection and diffusion.

The size of a CB is proportional to both flow velocity and the time step for advection. In the case of merging at a junction, total oxygen volumes in last CBs of the predecessor capillary segment are conveyed to the first CB of the successor capillary segment (FIG. 14). In the case of branching at a junction, conservation of blood flow is enforced to appropriately distribute the oxygen volume in the last CB of the parent capillary segment to the first CB of the daughter capillary segments (FIG. 14). Mathematical descriptions were detailed as equations (9)-(11) in the Detailed Description of the Model section below. The benefit of the conveyor-belt model of oxygen advection is the flexibility of adjusting the number of CBs in a CAP without interference with oxygen diffusion. When occlusion occurs, flow velocities change on the capillary network and accordingly the size and number of CB on a CAP also change. This alters the discretization for oxygen advection, but the module of oxygen diffusion remains unaffected. A simple rule is followed to associate a CB with CAP: a CB is associated with a CAP if the CB's center is enclosed by the CAP's volume. Then, the following sequence of processes is used to link modules of advection and diffusion: (1) oxygen advection in CBs on each capillary segment at time step $t_0$; (2) conversion of oxygen volume from CB-level to CAP-level just before diffusion at time step $t_0$; (3) oxygen diffusion involving CAPs and their surrounding objects at time step $t_0$; (4) conversion of oxygen volume from CAP-level to CB-level just before advection at time step $(t_0+\Delta t)$ (FIG. 15). More details on the CB model of oxygen advection are in the Detailed Description of the Model section below.

Referring to FIG. 15, during each time step, simulation of advection precedes simulation of other processes including diffusion. After advection (involving the CBs delivering the blood containing oxygen) and before diffusion (involving CAPs), a CAP always sums up oxygen volumes in all its associated CBs and update its pre-diffusion oxygen volume. Simulation of diffusion updates the CAP to have its post-diffusion oxygen volume. After diffusion and before advection at the next time step, the associated CBs must have the same relative change of oxygen volumes as the CAP gains or loses during diffusion, namely, percent change from pre-diffusion to post-diffusion values. This mathematically recognizes the conservation of oxygen. Three consecutive time steps are shown in the example A naïve assumption here for this illustration is that the first CB always receives 1 unit oxygen volume from upstream (not drawn). Another simplification made for this illustration is that only diffusion between the CAP (shown in red) and nearby OT (shown in light brown) are considered. In the actual model OT to OT diffusion is also treated. Note that in a certain step, boldface numbers represent values being changed or updated. During the first time step from $t_0$ to $t_0+\Delta t$, while the second CAP and its associated CBs still have a zero oxygen volume, the first CAP and associated CBs undergo (1) the process of advection that passes 1 unit volume to first CB, while CAPs are not involved; (2) an intermediate step that updates CAP's pre-diffusion oxygen volume by adding 1 (its first associated CB) and 0 (its second associated CB); (3) the process of diffusion delivers 0.2 to OT in contact (amount assumed for convenience in this example, and again OT-OT diffusion is ignored in this example) and CAP's post-diffusion oxygen volume becomes 0.8, while CBs are not involved; (4) a last step in the time period that updates CAP's associated CBs' oxygen volumes by subtracting 0.2/1=20% (diffused/pre-diffusion), the first CB thus having 0.8 oxygen volume now. During the second time step from $t_0+\Delta t$ to $t_0+2\Delta t$, similar verbal "simulation" goes. (1) process of advection goes as another 1 oxygen volume is passed to first CB and 0.8, previously held by the first CB, is passed to the second CB; (2) an intermediate step adds 1 and 0.8 to first CAP, still none added to the second CAP; (3) the process of diffusion updates first CAP's oxygen volume to 1.44, with 0.36 diffused out; (4) last step updates oxygen volumes in both of the host CAP's two CBs, again by subtracting diffused fraction 0.36/1.8=20%. During the third time step from $t_0+2\Delta t$ to $t_0+3\Delta t$, advection now passes oxygen volume 0.64, previously held by the second CB, into the third CB, which is associated with the second CAP. An intermediate step updates both CAPs by summing up oxygen volumes in their associated CBs. Process of diffusion now changes the oxygen volumes of both CAPs, with the first and second diffusing out 0.36/1.8=20% and 0.1/0.64=15.625% respectively. The last step subtracts the oxygen volumes of their asscociated CBs' with the percent change.

To model diffusion of a chemical field, it was assumed that each generalized cell has a uniform intra-cellular chemical concentration and that diffusion occurs at the interface between neighboring cell pairs. Metabolism of oxygen and synthesis and decay of VEGF are modeled as an intra-cellular process (FIG. 13). As for diffusion, the rate of exchange of oxygen or VEGF between generalized cells is proportional to inter-cellular gradient of concentration and inter-cellular contact surface area. Metabolism of oxygen obeys Michaelis-Menton kinetics, which assumes variability of oxygen consumption given different intracellular oxygen tension. Synthesis of VEGF in hypoxic MC is dependent on intra-cellular oxygen tension and VEGF level. Decay of VEGF is modeled using first-order kinetics. FAZ region is treated as both an oxygen source and a VEGF sink. Details on oxygen and VEGF fluxes are found in the Detailed Description of the Model section below.

Model Workflow

Figure 16:
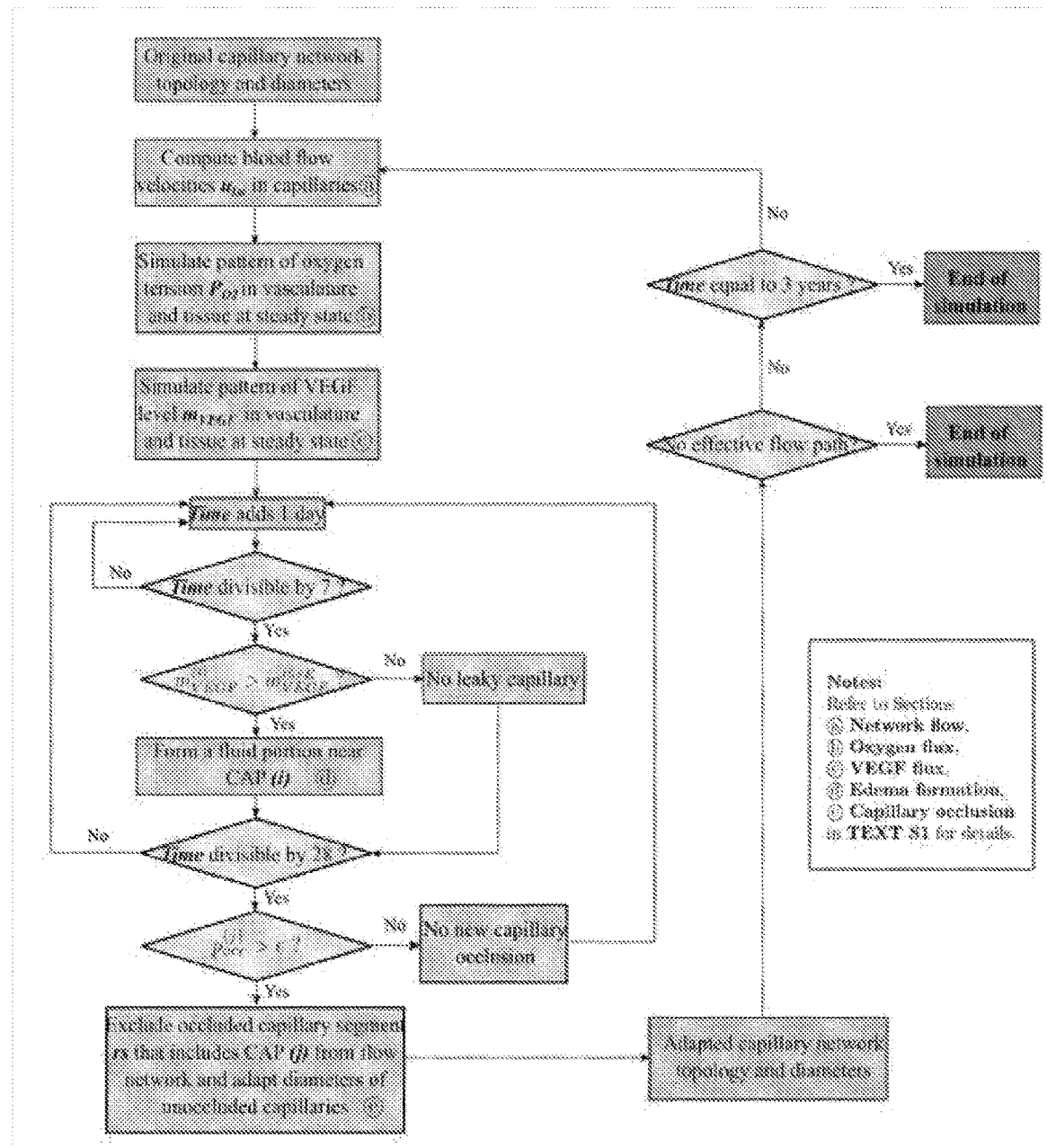
FIG. 16 depicts the workflow of the model described in the Material and Methods section.

The present simulation involves three distinct intervals of time: the time step of integration for oxygen and VEGF flux, $\Delta t_f$; the time interval to check edema formation, $\Delta t_e$; and the time interval to check for occlusion, $\Delta t_o$. The $\Delta t_f$ is chosen so that the differential equations of fluxes are properly integrated. In contrast, $\Delta t_e$ and $\Delta t_o$ are selected so that possible edema formation and capillary occlusion take place at a significantly slower pace (months to years), as compared with fast establishment (seconds) of the oxygen and VEGF steady state following a newly derived occlusion. With $\Delta t_f=0.002$ s, $\Delta t_e=7$ days, $\Delta t_o=28$ days, a model workflow is shown in FIG. 16. The time for oxygen and VEGF steady state is basically mandated by physics whereas the other longer times for edema and capillary occlusion are chosen to allow the model to progress in rough accordance to the progression of clinical disease.

Referring to FIG. 16, simulation is initialized with input of the original capillary network topology and structure as well as the component cells. Computation of flow velocities and simulation of oxygen and VEGF fluxes occurs next. Each model week the model addresses capillary leakiness and each model month capillary occlusion is evaluated. (1) If no new occlusion occurs, the model simply repeats checking for edema formation and capillary occlusion until occlusion occurs or until a pre-assigned simulated time (3 years at our temporal conversion rate) is arrived at. (2) Once a new occlusion occurs, the network topology is changed and its structure is adapted to eliminate flow in the irreversibly occluded capillary, followed by a new iteration of previous steps. The process stops if either no more effective flow paths exist, invalidating flow velocity calculations, or the pre-assigned simulated time is arrived at.

1. Input of Network Anatomy.

The simulation starts with input of a capillary network and cells. Both structural and topological information of the capillary network is required. In the present model, initial structural and topological information is determined by digitization of an experimental image obtained by AOSLO imaging. Diameters of capillaries ($d^{cap}$ were estimated to follow a Gaussian distribution with mean value of 5 μm and standard deviation of 0.5 μm based on measurement of the AOSLO image, and the terminal venule and arteriole were measured to have larger diameters up to 10 µm. This structural information, with topological information of nodes and edges, is read into CompuCell3D to reconstruct the capillary network. Next, the Mueller cells, MCs, were organized uniformly into the open space surrounding the capillary network. These are of roughly anatomical size. The space not occupied by MCs becomes the other tissue (OT). More details in boundary conditions and initial state of simulation of the Detailed Description of the Model section below.

2. Computation of Flow Velocities.

Blood flow directions and rates were determined using the Poiseuille equation, with hydrostatic pressures at boundary nodes given and fixed through the simulation. Boundary nodes refer to all those extending to the capillary network outside the region of interest, including the arterial inlet and venous outlet. More details in Network flow of the Detailed Description of the Model section below.

3. Simulation of Oxygen Fluxes.

Simulation of oxygen advection, diffusion and consumption are divided into three separate sub-modules sharing the same time-step of integration $\Delta t_f$. An important feature of the model is that advection is simulated at CB level, while diffusion and consumption are simulated at inter-cellular and cellular levels respectively. Therefore, before actual simulations of advection, a process is needed which reads current CAP-level oxygen volume to update CB-level oxygen volume. After simulation of advection by the CBs and before simulation of diffusion and consumption of oxygen, a process is needed to convert CB-level oxygen volume to CAP-level oxygen volume. The simulation of oxygen fluxes is executed until all model objects arrive at a steady state of oxygen tension. More details in Oxygen flux of the Detailed Description of the Model section below.

4. Simulations of VEGF Fluxes.

Simulations of VEGF synthesis, diffusion and decay are divided into separate sub-modules which share the same time of integration as the oxygen flux, $\Delta t_f$. This module follows immediately after the simulation of oxygen fluxes. The simulation of VEGF fluxes is executed until all model objects arrive at the steady state of VEGF level. More details in VEGF flux of the Detailed Description of the Model section below.

5. Formation of Edema.

Every period of $\Delta t_o$, the condition for edema formation is checked for all CAP objects. Once local VEGF level at a CAP exceeds a pre-defined threshold, edema is formed near the CAP. The edema is modeled as a pseudo cell FP, which is created every $\Delta t_o$ as long as the requirement of supra-threshold VEGF is met, namely, the $\Delta t_o$ remains in a "leaky" state. Fluid portions of the pseudo cell get eliminated at the bottom of the system, which represents the function of the retinal pigment epithelium removing excess fluid. More details in Edema formation of the Detailed Description of the Model section below.

6. Probabilistic Dependence of Capillary Occlusion.

Every period of $\Delta t_e$, the probability function for determining capillary occlusion is checked for all CAP objects. If the requirement, which is dependent on the intracellular VEGF level of a CAP and blood flow velocity of the capillary segment, is met, the CAP turns to the "occluded" state, and so do all CAPs that belong to the same capillary segment. Consequently, the capillary segment acquires an infinite flow resistance (in the model, an infinitesimal number is now assigned to the diameter of the segment) and is effectively occluded. More details in Capillary occlusion of the Detailed Description of the Model section below. This is the model's representation of the process of capillary occlusion by a leukocyte. A high flow is assumed to make adhesion of a leukocyte less likely as mechanically the leukocyte is experiencing more pressure pushing it down the capillary. The dependence on levels of VEGF subsumes the dependence of local ICAM levels on local VEGF, with higher VEGF levels giving higher ICAM levels and increased leukocyte adhesion.

7. On Occurrence or Absence of a New Capillary Occlusion.

If occlusion occurs, network topology changes and capillary diameters are slightly adapted in response to hemodynamic and metabolic stimuli. Steps (2)-(6) are repeated until the end of the simulation or until all patent capillary flow paths no longer exists. If no occlusion occurs, steps (5)-(6) are repeated until a new occlusion occurs or until the end of the simulation.

Model Outputs

Capillary Occlusion

Figure 17A:
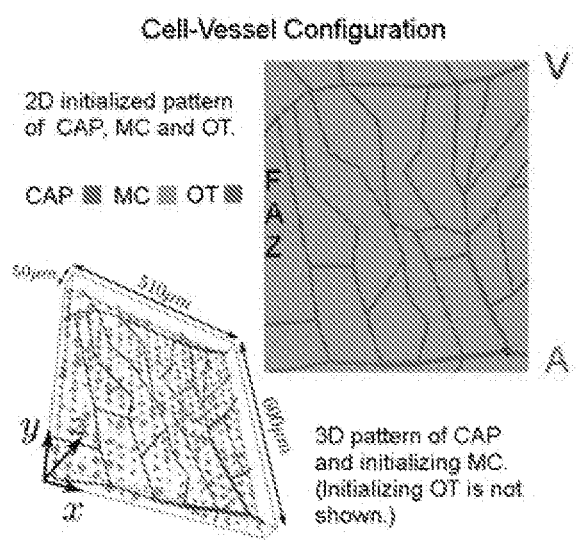
FIG. 17A depicts the capillary network for modeled CASE 1.
Figure 17B:
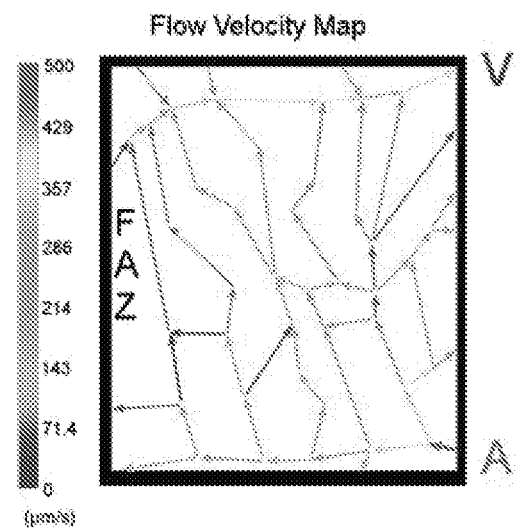
FIG. 17B depicts the flow velocity map for modeled CASE 1.

The model starts with the cell-vessel configuration show in FIG. 17A. FIG. 17A depicts the 2D XY cross section involving capillary network, Mueller cells (green) and other retina cells (brown) are uniformly initialized between capillary segments composed of capillary blocks (red). The 3D image of FIG. 17A depicts the simulated section during initialization (in the 3D completely initialized configuration, the capillary network is covered by MC and OT cells and visually inaccessible). The dimension of the simulated retinal section is 510 µm×600 µm×50 µm. In order to visually track occlusions of the capillary network, blood flow pathways are shown using a color map at each time point (FIG. 17B). The flow velocity map includes a primary arteriolar entrance (bottom right in FIG. 17B), a main venular exit (top right), side traffic extending outside region of interest, and interconnected pathways. Capillaries closer to the FAZ (left in the figure) carry blood flow with relatively smaller velocity. The unit for velocity is µm/s. Additionally the model calculates the average minimal cell-to-vessel distance $d^{min}$, which measures the distance from a Mueller cell to its closest patent, or non-occluded, capillary segment as a system output.

Ischemia

Figure 17C:
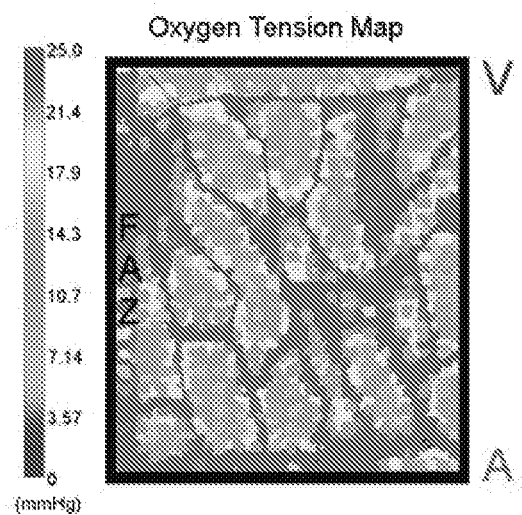
FIG. 17C depicts the oxygen tension map for modeled CASE 1.
Figure 17D:
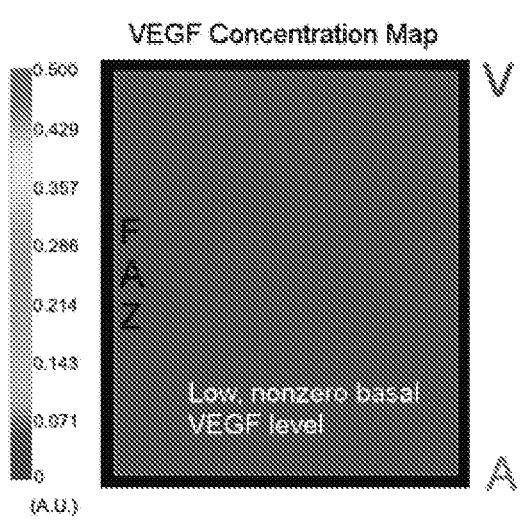
FIG. 17D depicts the VEGF concentration map for modeled CASE 1.

Oxygenation of the retina is visualized using a color map in which the spatial distribution of oxygen is presented and ischemia is highlighted in blue (FIG. 17C). Oxygen tension is highest near capillary segments and the FAZ. The more distant a cell is from irrigating capillaries, the lower is its oxygen level. The unit for oxygen tension is mmHg. In addition, the model takes advantage of the average oxygen tension of all Mueller cells as a global metric of the oxygen supply condition. At the same time, distribution of cellular oxygen indicates the fraction of cells that are insufficiently oxygenated, i.e. ischemic. The consequence of ischemia is local production of VEGF and produces a resulting equilibrium VEGF concentration map (FIG. 17D). VEGF levels are initially assumed to be at a low but nonzero basal concentration across in the whole area. VEGF level has arbitrary units. "FAZ refers to foveal avascular zone, "A" refers to arteriole, and "V" refers to venule.

Flow

Total inflow rate is monitored in the model as system output indicating of how well the modeled section of tissue is receiving oxygenated blood. In addition, a vector map embedded on the capillary network shows the spatial distribution of flow velocities which are color coded.

Retinal Thickness

A color coded profile of retinal thickness, acting as a retinal edema surrogate, is monitored with the progression of the occlusive process. Retinal thickness simply refers to magnitude in Z axis of simulated section (FIG. 17A).

Detailed Description of the Model

Network Flow

To calculate the blood flow velocities within a capillary segment lm (segment refers to capillary vessel between two branch junctions l and m), the Poiseuille equation was applied, which relates the flow resistance to capillary diameter, length and the apparent viscosity:

$$\dot{Q}_{lm} = \frac{\pi (P_l - P_m) D_{lm}^4}{128 \eta_{lm} L_{lm}} \quad (1)$$

where $\dot{Q}_{lm}$ is the volume flow rate from branching node l to m; $P_l$ is hydrostatic pressure at junction l, $P_m$ is the hydrostatic pressure at m; $D_{lm}$ is intraluminal diameter of the segment; $\eta_{lm}$ is the effective viscosity of blood within this segment; $L_{lm}$ is the length of the segment.

Pries et al. summarized a relation of in vivo effective viscosity with vessel segment diameter and hematocrit by studying in vivo rheology of blood (Pries et al. Circ. Res. 1990; 67(4):826-34; Pries et al. Circ Res. 1994; 75(5):904-15; and Pries et al. Am. J. Physiol. Heart. Circ. Physiol. 2005; 289(6):H2657-64). The proposed relation is in agreement with Fåhraeus-Lindqvist effect, which describes decreasing effective viscosity with decreasing diameter down to approximately 10 µm and inverse Fåhraeus-Lindqvist effect which describes increasing effective viscosity with decreasing diameter for smaller diameters than 10 µm. The relation of in vitro apparent viscosity with tube diameter of segment lm and hematocrit is given as:

$$\eta_{vitro} = 1 + (\eta_{0.45} - 1) \cdot \frac{(1 - H_D)^C - 1}{(1 - 0.45)^C - 1} \quad (2)$$

where the C and $\eta_{0.45}$ are calculated respectively as:

$$C = (0.8 + e^{-0.075 D_{lm}}) \cdot \left(-1 + \frac{1}{1 + 10^{-11} \cdot D_{lm}^{12}}\right) + \frac{1}{1 + 10^{-11} \cdot D_{lm}^{12}} \quad (3)$$

and $$\eta_{0.45} = 220 e^{-1.3 D_{lm}} + 3.2 - 2.44 e^{-0.06 D_{lm}^{0.645}} \quad (4)$$

Equation (2) would give in vitro effective viscosity. According to Pries et al., flow resistance in vivo can be explained by in vitro viscosity and the effect of an endothelial surface layer that impedes blood flow (Pries et al., Am. J. Physiol. Heart Circ. Physiol. 2005; 289(6):H2657-64 and Pries et al., Pflugers Arch. 2000; 440(5):653-66). Then in vivo viscosity is calculated as $\eta_{vivo} = \eta_{vitro} \cdot (D_{lm}/D_{lm}^{eff})^4$, where $D_{lm}^{eff}$ is effective diameter of this segment, as calculated from equations (8)-(11). It was assumed that hematocrit in each capillary segment maintained the value of 0.45 in all calculations, though plasma skimming is a known phenomenon which would progressively elevate hematocrit along an arteriole.

The present model also includes the structural adaptation module which adjusts effective diameters of all capillaries slightly after each occlusion. Reglin et al. (Am. J. Physiol. Heart Circ. Physiol. 2009; 297(6):H2206-19) proposed the convergence-aimed method to adapt diameters in response to hemodynamic and metabolic stimuli with the form of $\Delta D = \Delta t \cdot S_{tot} \cdot D$, where $\Delta t = 0.5 \cdot \Delta t_f$ in the model and $S_{tot} = k_h(S_t + k_p S_p) + k_m(S_m + k_c S_c) - k_s$ is a combination of four stimuli: transmural pressure $S_p = -\log(100 - 86 e^{-5000 \ (log \ (P))^{5.4}})$ shear stress $S_\tau = \log(\tau + 0.103)$, oxygen tension $S_m = \log(1 + 1.38 L(1 - P_{O_2}/P_{O_2}^{ref})/(\dot{Q} + \dot{Q}_{ref}))$, and conducted signal $S_c$. $k_h$, $k_p$, $k_m$, $k_c$ and $k_s$ are five coefficients, with values 1, 0.2, 1, 1.6 and 2 respectively. Stimulus caused by transmural pressure $S_p$, which is assumed to decrease sigmoidally with increase of transmural pressure, decreases diameter of the capillary. Increased stimulus caused by shear stress $S_\tau$ is assumed to result in an increase of diameter. The average oxygen tension of all CAP objects in each capillary segment was considered as the metabolic signal, with $P_{O_2}^{ref} = 100$ mmHg and $\dot{Q}_{ref} = 0.2$ pL/s in the present model, i.e. the lower the oxygen tension, the larger the metabolic stimulus. Increased stimulus caused by the metabolic signal $S_m$, the average oxygen tension in a capillary segment in the present model, is assumed to increase diameter. The fourth component of the total stimulus is conducted signal of metabolic information $S_c$ generated in a segment that affects an upstream segment (Reglin et al., Am. J. Physiol. Heart Circ. Physiol. 2009; 297(6):H2206-19). This module is not the focus of the present model, and the inclusion of the module is for qualitative description of the structural adaptation that can exist following capillary occlusions. The present model included all components of stimuli that contributed to adaptation of segment diameters but restricted the effect of adaption in the model by setting a relatively small $\Delta t$. Following each occlusion, the adaptation module for only one cycle of $\Delta t$ was executed. As observed, maximum diameter change due to such one-step adaptation is about 2%. Again, the purpose of this module is to make qualitative sense of diameter adaptation in response to hemodynamic and metabolic stimuli following updated distribution of flow velocities and oxygen tension. The extent to which such adaptation affects the progression of diabetic capillary occlusions remains clinically unclear, though given that IRMA are found surrounding local ischemic areas, there is likely at least some role.

Oxygen Flux

In the blood, oxygen exists in three compartments: hemoglobin-bound in red blood cells (RBCs), unbound in RBCs and unbound in plasma. Oxygen tension within blood, $P_{O_2}$, has the following relationship with oxygen concentration $c_{O_2}$:

$$c_{O_2} = H_D \cdot c_{Hb} \cdot s_{O_2} + H_D \cdot \alpha_{RBC} \cdot P_{O_2} + (1 - H_D) \cdot \alpha \cdot P_{O_2} \quad (5)$$

where each term in the summation corresponds to one of the three compartments. In the first term, $c_{Hb}$ is the concentration of hemoglobin within the RBC, and $s_{O_2}$ is the saturation of oxygen binding to hemoglobin, which acquires a form of Hill's function $$s_{O_2} = P_{O_2}^n / \left(P_{O_2}^n + P_{O_{2_{50}}}^n\right),$$

where n=3 and oxygen tension at half-maximal hemoglobin saturation is $$P_{O_{2_{50}}} = 38 \text{ mmHg}.$$

$\alpha_{RBC}$ is the solubility of unbound oxygen in RBCs. In the third term, $\alpha$ is the solubility of free oxygen in plasma.

In tissue, it was assumed that oxygen solubility was equal to $\alpha$. Then the relationship between oxygen tension and oxygen concentration follows Henry's law $c_{O_2}=\alpha \cdot P_{O_2}$. Diffusion of oxygen is modeled between all four cell types (CAP, FP, MC, OT), using a coarse-grained cell-to-cell transfer with the assumption that within each cell the oxygen tension is uniform. Within a short period of time $\alpha t_f$, the change of volume of oxygen within cell (i) due to cell-to-cell transfer is calculated as:

$$\Delta v_{O_2}^{(i)} = -\Delta t_f \cdot \sum_{(j)}^{N_{nb}^{(i)}} \frac{A_{(i)(j)} \cdot D_{O_2} \cdot \alpha \cdot (P_{O_2}^{(i)} - P_{O_2}^{(j)})}{d_{(i)(j)}} \qquad (6)$$

where $\Delta v_{O_2}^{(i)}$ is the change of oxygen volume in cell(i). Bracketed notation (i) used in superscripts and subscripts represents cell ids, distinguished from unbracketed i representing node ids of the capillary network, which applies to all following equations. On the right hand of the equation, $\Delta t_f$ is the time step of integration for simulation of oxygen and VEGF fluxes; $A_{(i)(j)}$ is the contact surface area between the pair of cell neighbors (i) and (j); $d_{(i)(j)}$ is the distance between centers of mass of cell (i) and cell (j); and the summation iterates over all of cell (i)'s neighbors in contact. $D_{O_2}$ is equal to $D_{O_2}^{pl}$ only if (i) is CAP and $D_{O_2}^{tis}$ otherwise.

For cells near the foveal avascular zone, there exists additional oxygen flux coming from the FAZ, assumed to be supplied by choroidal capillaries. In the model, the FAZ is treated as the whole side of a three dimensional system. If a cell touches this side, it receives oxygen from the FAZ. It was assumed that the FAZ has a constant oxygen tension $P_{O_2}^{faz}$, and additional change in oxygen volume within cell (i) due to FAZ-to-cell transfer is calculated as:

$$\Delta v'^{(i)}_{O_2} = -\Delta t_f \cdot \frac{A_{(i)}^{faz} \cdot D_{O_2}^{tis} \cdot \alpha \cdot (P_{O_2}^{(i)} - P_{O_2}^{faz})}{d_{(i)}^{faz}} \qquad (7)$$

where $\Delta v'^{(i)}_{O_2}$ is the additional change of oxygen volume in cell (i) due to its contact with FAZ and $(\Delta v_{O_2}^{(i)}+\Delta v'^{(i)}_{O_2})$ gives total change of oxygen volume for such cells; $A_{(i)}^{faz}$ is the contact surface area between FAZ and cell(i), which, for simplicity, is approximated to be one sixth of the cell surface area of cell(i); $d_{(i)}^{faz}$ is the distance from the center of cell (i) to the FAZ.

Consumption of oxygen is modeled for two cell types (MC, OT). In order to a capture cell's capability to adapt its demand for oxygen according to available oxygen supply, Michaelis-Menten type kinetics were applied to model oxygen consumption. Within a short period of time $\Delta t_f$, the change of volume of oxygen within cell (i) resulting from consumption is calculated as:

$$\Delta v_{O_2}^{(i)} = -\Delta t_f \cdot \frac{M_0 \cdot P_{O_2}^{(i)}}{P_{O_2}^{(i)} + P_{O_{20}}} \qquad (8)$$

where $M_0$ is the maximum oxygen consumption rate of cells; $P_{O_{20}}$ is the oxygen tension at which cells acquire the half maximum oxygen consumption rate.

A conveyor-belt like method is proposed to model the oxygen advection (FIGS. 14-15). One advantage is that each capillary segment can be flexibly re-discretized without interfering with diffusion module. This is useful when capillary occlusion occurs and flow velocities on other patent capillary segments change.

The module of oxygen advection is modeled for object CB, and oxygen volumes are converted between the CB and the CAP during each iteration of the simulation of fluxes. While CAP is the structural element (visually seen in the model configuration) of a capillary segment, CB is the functional element (visually hidden) for oxygen advection. On a certain capillary segment jk, the model discretizes the segment into a sequence of CBs, each with size $a_{jk}=u_{jk}\cdot \Delta t_f$, where $u_{jk}=\dot{Q}_{ij}(0.257\pi \cdot D_{ij}^2)$ is flow velocity on the segment. Thus, once oxygen in a CB is transferred to the closest downstream CB, oxygen moves with the speed of blood flow in that capillary segment. The slower the flow velocity on a capillary segment, the smaller each CB and the slower the advection of oxygen. All CBs on the same capillary segment have the same size, and the quantity of CBs on a capillary segment is simply the length of capillary segment divided by size of a single CB. The mapping of CBs to a CAP is decided by the center position of a CB after discretization. As long as the center of a CB is within the extent of a CAP, this CB belongs to this CAP. As an example, the first CAP contains first and second CB on segment jk, and the second CAP the third and fourth CB, and the last CAP the $(n-1)^{th}$ and $n^{th}$ CB (FIG. 14). During a small period of time $\Delta t_f$ that involves advection and diffusion, two intermediate steps are needed to convert oxygen volumes between a CAP and its associated CBs (FIG. 15): (1) modeling advection of oxygen volumes in CBs on each capillary segment at time step $t_0$; (2) summation of oxygen volumes at CB-level to update CAP-level immediately after advection at time step $t_0$; (3) modeling diffusion between objects as described above; (4) subtraction of CAP-level diffused oxygen volumes from associated CBs immediately after diffusion at time step $t_0$.

On a certain capillary segment jk which has $n_{jk}$ CBs, CBs $\{0, 1, 2, \ldots, n_{jk}-1\}$ carry oxygen volumes $\{M_{jk}^{[0]}, M_{jk}^{[1]}, M_{jk}^{[2]}, \ldots, M_{jk}^{[n_{jk}-1]}\}$, where superscript [i] refers to ranking of the CB on the segment. Following three equations are used for the simulation of advection (FIG. 14):

$$M_{jk}^{[i+1]}(t+\Delta t_f) = M_{jk}^{[i]}(t); 0 \le i < n_{jk} - 1 \qquad (9)$$

$$\begin{cases} M_{kr}^{[0]}(t+\Delta t_f) = M_{jk}^{[n_{jk}-1]}(t) \cdot \dfrac{S_{kr} \cdot u_{k,r}}{S_{jk} \cdot u_{jk}} \\ M_{ks}^{[0]}(t+\Delta t_f) = M_{jk}^{[n_{jk}-1]}(t) \cdot \dfrac{S_{ks} \cdot u_{ks}}{S_{jk} \cdot u_{jk}} \end{cases} \qquad (10)$$

$$M_{jk}^{[0]}(t+\Delta t_f) = M_{xj}^{[n_{xj}-1]}(t) + M_{yj}^{[n_{yj}-1]}(t) \qquad (11)$$

Equation (9) describes advection on a capillary segment, using jk as an example. Equation (10) describes the distribution of oxygen volumes at a junction that bifurcates a parent capillary segment into two daughter capillary segments, using junction k as an example. Equation (11) describes the summation of oxygen volumes at a junction that merges two predecessor capillary segments into one successor segment (FIG. 14). In equation (9), $n_{jk}-1$ is the ranking of last CB on segment jk. This equation (9) describes the process needed to "convey" oxygen volume from a CB to the closest downstream neighbor CB. In equation (10), $M_{jk}^{[n_{jk}-1]}$ is the oxygen volume in the last CB on parent capillary segment jk and $M_{ks}^{[0]}$ is oxygen volume in the first CB on one daughter capillary segment, ks in this case. $S_{jk} \cdot u_{jk}$ and $S_{ks} \cdot U_{ks}$ are the volumes of blood flow exiting segment jk and entering segment ks per unit time respectively. Based on conservation of volume of blood flow at the junction k and assumption that oxygen tension remain constant at the instant of blood flow leaving parent segment and entering two daughter segments, the first CB on segment ks receives a fraction of oxygen volume from last CB on segment jk, with the fraction equal to $(S_{ks} \cdot u_{ks})/(S_{jk} \cdot u_{jk})$. The same rule of distribution of oxygen volume into segment jk is applied. In equation (11), $M_{jk}^{[0]}$ is the oxygen volume in the first CB on successor capillary segment jk and $M_{xj}^{[n_{xj}-1]}$ is oxygen volume in the last CB on one predecessor capillary segment, xj in this case. According to conservation of volume of blood flow at the instant of merging flow, $M_{jk}^{[0]}$ is equal total amount of $M_{xj}^{[n_{xj}-1]}$ and $M_{xj}^{[n_{xj}-1]}$. General extensions can be made for junctions with N daughter segments and M parent segments with N and M greater than 1, using the combination of rules for branching and merging situation.

An example of the conveyor-belt model of oxygen advection is shown in FIG. 15. Three consecutive time steps are looked at. For purpose of clarity, within each time step only modules of oxygen advection and diffusion are included in the example and a simple route of diffusing flux (shown in black arrow) from the CAP (shown in light red) to OT (shown in light brown) is assumed. In addition, to emphasize the change of oxygen volumes in a given step, numbers are highlighted in bold. During the first time step from $t_0$ to $t_0+\Delta t$, while the second CAP and its associated CBs still have zero oxygen volume, the first CAP and associated CBs undergo (1) a process of advection that passes 1 unit oxygen volume (an example of an amount conveyed from upstream CB not shown) to the first CB, while CAPs are not involved in advection; (2) an intermediate step that updates CAP's pre-diffusion oxygen volume by adding 1 (its first associated CB) and 0 (its second associated CB); (3) the process of diffusion that delivers 0.2 to OT in contact (amount assumed for convenience in this example, and again only a simple CAP→OT diffusion is considered in this example) and CAP's post-diffusion oxygen volume becomes 0.8, while CBs are not involved in diffusion; (4) an ultimate step that updates CAP's associated CBs' oxygen volumes by subtracting diffused amount 0.2/1=20% (diffused/pre-diffusion), the first CB thus having 0.8 oxygen volume now. During the second time step from $t_0+\Delta t$ to $t_0+2\Delta t$, a similar verbal "simulation" proceeds. (1) process of advection takes place as another 1 oxygen volume is passed to first CB and 0.8, previously held by the first CB, passed to the second CB; (2) an intermediate step adds 1 and 0.8 to first CAP, but still none for the second CAP; (3) process of diffusion updates the first CAP's oxygen volume to 1.44, with 0.36 (chosen for convience in this example) diffused out; (4) an ultimate step updates oxygen volumes in both of CAP's two CBs, again by subtracting diffused fraction 0.36/1.8=20%. During the third time step from $t_0+2\Delta t$ to $t_0+3\Delta t$, advection now passes an oxygen volume of 0.64, previously held by the second CB, into the third CB, which is associated with the second CAP. An intermediate step updates both CAPs by summing up oxygen volumes in their associated CBs. The diffusion process now changes oxygen volumes of both CAPs, with the first and second diffusing out 0.36/1.8=20% and 0.1/0.64=15.625% respectively. An ultimate step subtracts oxygen volumes from their associated CBs' with the percent change.

VEGF Flux

In the present model, VEGF plays an important role in leading to occlusion of the capillary network. Specifically, VEGF synthesized and released by Mueller cells under hypoxic conditions is assumed to make a contribution in this model to both capillary occlusion and leakage. Physiologically, VEGF causes capillary occlusion indirectly by inducing ICAM expression on endothelial cells resulting in increased leukocyte leukostasis and capillary occlusion whereas in the model these intermediate steps are not treated. Edema, in the model, is considered a direct effect of elevated VEGF. In the current model, the synthesis of VEGF by model cell types other than MC was ignored. Also, advection of VEGF via blood flow was not treated.

Production of VEGF is modeled for one cell type (MC), with its synthesizing rate dependent on both current cellular VEGF level and oxygen tension. As the produced VEGF amount increases within a Mueller cell, the production rate drops corresponding to limited producing capacity of the cell partly owing to feedback signaling. In addition, the production rate is also directly dependent on a factor determined by a cellular oxygen tension threshold. When cellular oxygen tension is below a given hypoxic threshold, this factor rapidly approaches 1. During the period of time $\Delta t_f$, the change in concentration of VEGF in cell (i) is given by the following equation:

$$\Delta c_{VEGF}^{(i)} = \Delta t_f \cdot k_{VEGF}^{prod} \cdot \frac{1}{vol^{(i)}} \cdot \frac{m_{VEGF}^{max} - vol^{(i)} \cdot c_{VEGF}^{(i)}}{m_{VEGF}^{max}} \cdot \frac{e^{100 \cdot (P_{O_2}^{hyp} - P_{O_2}^{(i)})}}{e^{100 \cdot (P_{O_2}^{hyp} - P_{O_2}^{(i)})} + 1} \quad (12)$$

where $k_{VEGF}^{prod}$ is production rate constant of VEGF; $m_{VEGF}^{max}$ is the capacity of VEGF production; $P_{O_2}^{hyp}$ is the threshold of oxygen tension separating normoxia and hypoxia; $vol^{(i)}$ is the volume of cell(i); $c_{VEGF}^{(i)}$ is the cellular VEGF concentration and $P_{O_2}^{(i)}$ is the cellular oxygen tension.

Decay of VEGF is modeled for four cell types (CAP, FP, MC, and OT). During a short period of time $\Delta t_f$, the change in concentration of cellular VEGF due to decay is described by the following equation:

$$\Delta c_{VEGF}^{(i)} = -\Delta t_f k_{VEGF}^{dec} \cdot c_{VEGF}^{(i)} \quad (13)$$

where $k_{VEGF}^{dec}$ is the decay rate constant of VEGF.

Diffusion of VEGF is modeled between certain pairs of the four cell types (CAP, FP, MC, and OT), which includes following fluxes: MC→OT, OT→OT, FP→FP, OT→FP, FP→CAP and OT→CAP. The model assumes that VEGF is not absorbed by MC and doesn't exit CAP by advection. The governing equation for transfer of VEGF from cell (i) is similar to that describing oxygen diffusion:

$$\Delta c_{VEGF}^{(i)} = -\Delta t_f \sum_{(j)} \frac{A_{(i)(j)} \cdot D_{VEGF}^{tis} \cdot (c_{VEGF}^{(i)} - c_{VEGF}^{(j)})}{d_{(i)(j)}} \quad (14)$$

where $D_{VEGF}^{tis}$ is the approximated diffusion rate coefficient of VEGF within tissue space. And possible directions of (i)→(j) obey the above regulations for transfer fluxes.

Similar to the situation for the diffusion of oxygen, there exists an additional flux for cells in contact with the FAZ, where FAZ serves as a sink for VEGF and it rapidly removes VEGF. The additional change in VEGF concentration within cell (i) when touching FAZ is calculated as:

$$\Delta c_{VEGF}^{\prime(i)} = -\Delta t_f \cdot \frac{A_{(i)}^{faz} \cdot D_{VEGF}^{tis} \cdot c_{VEGF}^{(i)}}{d_{(i)}^{faz}} \quad (15)$$

where $A_{(i)}^{faz}$ and $d_{(i)}^{faz}$ follow the same approximation rule as for oxygen diffusion.

Capillary Occlusion

A probabilistic function was used to determine the occurrence of a capillary occlusion. Occlusion is an irreversible process in the model, since occluded capillaries would ultimately become acellular, likely resulting from biochemical interactions with the occluding leukocyte. Physiologically, there are recurrent temporary occlusions due to leukostasis which ultimately, through loss of endothelial cells and limits on their regeneration, result in irreversible capillary occlusion. The model only addresses this final capillary occluding event. The time interval between two events which calculate the probability of capillary occlusion is much greater than the time step of integration of the ODEs descriptive of oxygen and VEGF flux. In the present model, judgement of capillary occlusion is made at the CAP level. Every period of time $\Delta t_O$, the calculated probability of occlusion of each CAP cell (i), $p_{occ}^{(i)}$, is compared with a random number between 0 and 1. Occlusion occurs if the former is greater than the latter (Table 5). If the occlusion decision is made, the diameter of the whole capillary segment kl that the CAP cell (i) belongs to will be set to an infinitesimal number (not zero because of division by zero issues). Mathematically this gives a huge resistance to blood flow as the equivalent of vascular obstruction. This probability function is related to both local VEGF level and the blood flow velocity, and has the following form:

$$p_{occ}^{(i)} = \frac{vol^{(i)} \cdot c_{VEGF}^{(i)}}{m_{VEGF}^{thr} + vol^{(i)} \cdot c_{VEGF}^{(i)}} \cdot \frac{(u^{thr})^2}{(u^{thr})^2 + (u^{kl})^2} \quad (16)$$

where $u^{thr}$ is a critical blood flow velocity, $m_{VEGF}^{thr}$ is a critical VEGF level, and $vol^{(i)}$ is the volume of CAP (i).

The form of the occlusion probability function is chosen so that it has a sigmoid shape in response to each VEGF level and flow velocity. Higher VEGF level and lower flow velocity give greater occlusion probability. Exponents in the probability function control the steepness of sigmoid curve, while VEGF level equal to $m_{VEGF}^{thr}$ and flow velocity equal to $u^{thr}$ correspond to the steepest part of the sigmoid curve. As discussed in the Parameter selection and analysis of parameter influence section below, a wide range of values are tested for $m_{VEGF}^{thr}$ and $u^{thr}$. Variation in each parameter greatly influences capillary network patency and retinal thickness.

Edema Formation

Edema formation is triggered by elevation of VEGF above a threshold. In the present model, a pseudo cell type fluid portion (FP) was used as the edema component. It was assumed that the FP is an object that barely spreads and is trapped by surrounding objects. It was also assumed that a patent (unoccluded) capillary segment becomes leaky if any of its member CAPs' local VEGF level is greater than a threshold, i.e., $vol^{(i)} \cdot c_{VEGF}^{(i)} > m_{VEGF}^{thrE}$ (Table 5). Edema is formed only near the leaky site (i). A FP is created nearby a leaky CAP at every $\Delta t_e$ as a visual representation of leaked fluid and is the cause of retinal thickening. In addition, a pumping mechanism, representing retinal pigment epithelial cell function, is added to eliminate the FPs only if they are large enough to physically touch the bottom boundary surface at Z=0. This reflects the role of the retinal pigment epithelial pumps to remove excess accumulated fluid.

The creation of FP is similar to initialization of cells at the start of the simulation. A voxel in contact with a randomly chosen surface voxel of the leaky CAP is selected as a seed for a FP. Then the Cellular Potts Model is implemented for expansion of the one-voxel seed to pre-defined size $vol^{FP}$. During the expansion, FP displaces surrounding cells to result in thickening of retinal tissue. According to the Cellular Potts model (see Graner and Glazier, Phys. Rev. Lett. 19992; 69(13):2013-6 and Glazier and Graner, Phys Rev E Stat Phys Plasmas Fluids Relat Interdiscip Topics. 1993; 47(3):2128-54), the growth of the FP seed and the pushing effect are effectively governed by minimization of the following Hamiltonian:

$$H = \sum_{i,j \; neighbors} J(\tau(\sigma(i)), \tau(\sigma(j))) \cdot (1 - \delta(\sigma(i), \sigma(j))) + \sum_i \lambda_{vol} \cdot (vol(\sigma(i)) - vol^{tgt}(\sigma(i)))^2 \quad (17)$$

where the first summation describes adhesion energy between cells and the second summation describes the volume constraint of cells. $\tau(\sigma(i))$ stands for cell type of cell $\sigma(i)$. $J(\tau(\sigma(i)), \tau(\sigma(j)))$ is the adhesion energy for the two cells types between lattice sites i, j. The term $(1-\delta(\sigma(i), \sigma(j)))$ limits calculation of adhesion energy only between lattice sites representing different cells. $\lambda_{vol}$ specifies the strength of volume constraint. $vol(\sigma(i))$ and $vol^{tgt}(\sigma(i))$ are present cell volumes and target cell volumes respectively.

In terms of edema formation, $\lambda_{vol}$ acquires a large value and $vol^{tgt}$ is equal to $vol^{FP}$ so that a slight deviation from the target volume increases H significantly and thus the pseudo cells rapidly grow to the target size. In terms of fluid elimination at the bottom, $vol^{tgt}$ is instead set to 0, which shrinks the FP. It should be noted that Cellular Potts Model is not essential for modeling the expansion of the FP seed to pre-defined size. However, the Cellular Potts model brings convenience to the process of surrounding cell rearrangement once FP is formed.

Boundary Conditions and Initial State of Stimulation

Figure 26:
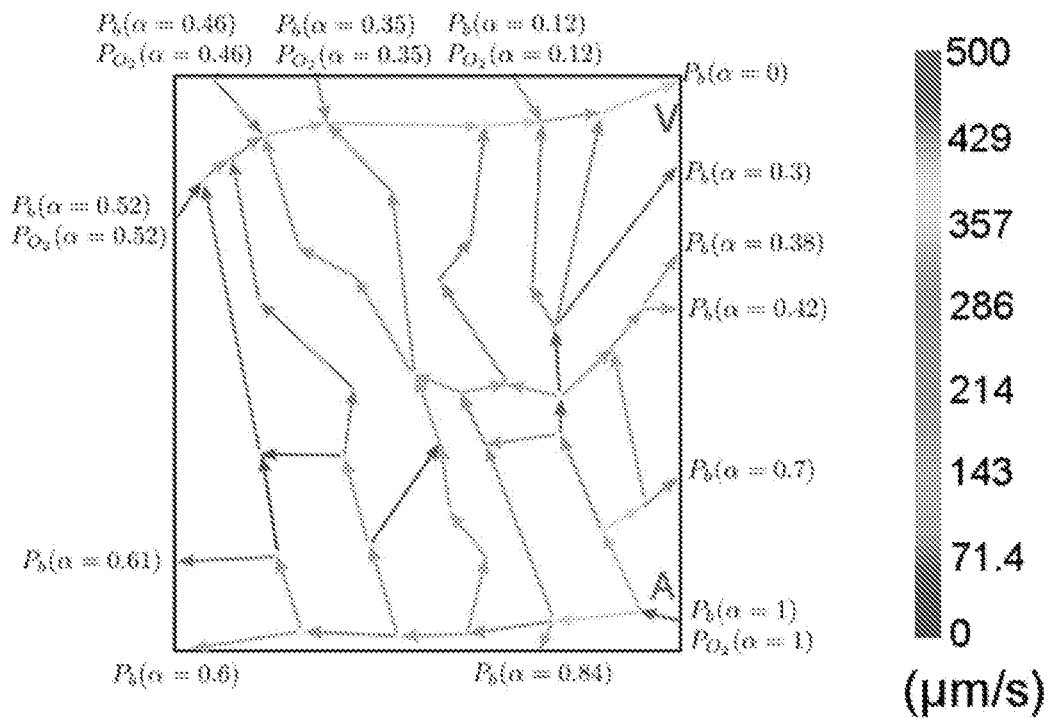
FIG. 26 depicts boundary conditions for CASE 1 and CASE 2 simulations. The image indicates values of blood pressures and oxygen tensions at all boundary nodes.

A few boundary conditions are imposed in the model. The first boundary condition assigns values for hydrostatic pressures and incoming oxygen tension of boundary nodes used by the network flow module. In terms of hydrostatic pressures, arteriolar node (A) has pressure $P_b^{art}$, venous node (V) has pressure $P_b^{ven}$, and all others have intermediate pressure values $\Delta \cdot p_b^{art} + (1-\alpha) \cdot p_b^{art}$. Three criteria (i), (ii), (iii) were considered when selecting pressure values for boundary nodes which are neither A or V. (i) an estimate of pressure values for boundary nodes was made depending on ratio of their topological distance from A and that from V:β. Topological distance is defined as the shortest path length between two nodes. Pressure values were calculated based on topological distance, the smaller β is, the higher the nodal pressure assigned, namely a greater α is used. (ii) It was assumed that a capillary segment involving a boundary node is always a "daughter" edge of the relevant junction. For each junction in the network, there may exist "daughter" edges with a "parent" edge (in some places, a "predecessor"-"successor" relationship was alternatively used if it's a merging junction instead of branching junction). (iii) It was assumed that if β is small, a node connected with a boundary node is likely a branching junction where the flow velocity vector points to the boundary node representing outflow. In contrast, for nodes topologically closer to venous outlet node, it's likely a merging junction where the flow velocity vector points from the boundary node representing inflow. During progression of capillary occlusions, all these pressure values were fixed. Refer to FIG. 26 for a flow velocity map under normal condition with marked pressure values for all boundary nodes in CASE 1 Similar rules are used for the boundary values of incoming oxygen tension within blood. Outgoing oxygen tension is not assigned but calculated from the steady state simulation. Arteriolar node (A) has pressure $P_{O_2}^{art}$ and all other inlet boundary nodes have intermediate pressure values $\alpha \cdot P_{O_2}^{art}+(1-\alpha) \cdot 20$. It was assumed that cells don't move outside any of the six boundary surfaces. Therefore, the second boundary condition is that there are no periodic boundary conditions. It was assumed that FAZ is a perfect stable oxygen source and VEGF sink. Therefore, the third boundary condition assigns a fixed oxygen tension of $P_{O_2}^{faz}$ and also assigns a zero VEGF level to the FAZ region.

The initial state of the model configuration is reconstructed as a vessel network with uniformly seeded cell centers, each occupying one voxel. The Cellular Potts model is implemented to grow one-voxel cells to proper size, i.e., $\alpha^{MC}$ or $\alpha^{OT}$, in a similar fashion as discussed in the Edema formation section. In addition, it was assumed initially a low baseline level of VEGF (1% of $m_{VEGF}^{thr}$) in all cell types merely serving the purpose of representing initial diabetic physiological conditions and creating a very small but non-zero probability of capillary occlusion. Note that the diabetic likely has a significant elevation of leukocyte adhesion probability even in the first weeks of the diabetic state according to animal models, prior to any permanent capillary occlusion. However these leukocyte adhesion events do not result in permanent occlusions because the endothelial cell population has not yet been depleted by these recurrent events. The model deals only with the permanent occlusion events. In the model the initial oxygen tension ("initial" here means after construction of cells and vessels but before any simulation of fluxes) is zero everywhere, which will be updated after simulation of oxygen advection/diffusion/metabolism under normal condition.

Parameter Selection and Analysis of Parameter Influence

Parameters in the model were divided into three general categories: geometrical parameters, temporal parameters and module parameters.

Geometrical parameters are selected based on either imaging pictures (e.g., CASE 1) or a published structural drawing (Peripheral network; Spitznas and Bornfeld, Albrecht Von Graefes Arch Klin Exp Ophthalmol. 1977; 203(3-4):217-29). Modeled cell sizes are selected to be anatomically reasonable (Table 2) especially for the MCs and the CAPs. Conversion rate from pixels to microns is 2 micron per pixel, chosen with consideration of both computational cost and visualization resolution.

Temporal parameters are selected based on simulation requirements. The parameter $\Delta t_f$ is the time step of integration for simulation of oxygen and VEGF fluxes. The criterion is that it should be small enough to ensure proper and stable integration of differential equations, and large enough to allow practical computation. All other temporal parameters were selected so that the model produces time scales comparable to clinical observations. Conversion rate of MCS to seconds is 86,400 second per MCS is selected as long as equivalent time of 1 MCS is much greater than $\Delta t_f$.

It was assumed that it takes much longer to result in a new possible capillary occlusion than it does to simulate the steady state of fluxes. The former, from clinical experience and animal experimentation, ranges from days to weeks to years, while the latter occur in seconds.

Some module parameters were well studied in published studies, such as those related to oxygen and VEGF. Beyond these, some model-specific parameters were introduced that are not described elsewhere, such as $k_{VEGF}^{prod}$ involved in VEGF synthesis, $m_{VEGF}^{thr}$ and $u^{thr}$ involved in the calculation of occlusion probability, and $m_{VEGF}^{thrE}$ involved in edema formation. Such parameters were mainly selected for convenience in order to produce qualitatively comparable model outputs. Therefore, to get a better understanding of the influence of several important parameters on model outputs, a number of parameters were varied one-at-a-time around their reference values and investigated how two model outputs at the end of the simulation, capillary patency index and mean retinal thickness change, were affected (FIG. 27). Note that the mean retinal thickness change parameter map has an abscissa with a maximum of only 5%. This may seem small but this is mean retinal thickness averaged over the entire area and retinal edema was generally localized. The parameters selected are: diffusion coefficient of VEGF $D_{VEGF}^{tis}$, critical blood flow velocity $u^{thr}$, critical VEGF level $m_{VEGF}^{thr}$, maximum synthesis rate of VEGF $k_{VEGF}^{prod}$, threshold of VEGF level to trigger edema $m_{VEGF}^{thrE}$, and maximum metabolic rate of oxygen $M_0$. All parameter variation simulations use CASE 1 parameters as a reference point denoted as "1×". Capillary patency index, calculated as fraction of patent (i.e., unoccluded) capillaries at the end of the simulation with magnitude ranging from 0% to 100%, measures the degree of progression of the capillary occlusion within the simulation. Higher value of $D_{VEGF}^{tis}$, higher value of $k_{VEGF}^{prod}$, higher value of $u^{thr}$, higher value of $M_0$ and lower value of $m_{VEGF}^{thr}$ result in comparably smaller capillary patency index in slightly different ways (FIG. 27). Increase of $D_{VEGF}^{tis}$ enhances the diffusing length of VEGF, while increase of $k_{VEGF}^{prod}$, on the other hand, increases synthesis rate of VEGF by Mueller cells. In contrast, increase of $u^{thr}$ or decrease of $m_{VEGF}^{thr}$ raises occlusion probability given a certain blood flow velocity or VEGF level respectively. Nevertheless, $m_{VEGF}^{thrE}$ shows little effect on the patency index, because it plays no role in probabilistic judgement on capillary occlusion.

Relative thickness change is calculated literally as percentage of variation in average magnitude along Z direction of the retinal tissue at the end of simulation. A higher value of $m_{VEGF}^{thrE}$, a higher value of $D_{VEGF}^{tis}$ and a lower value of $k_{VEGF}^{prod}$ all lead to less retinal thickening (FIG. 27). Apparently, $m_{VEGF}^{thrE}$ influences retinal thickness change significantly, by directly determining how persistently edema is formed. In contrast, $D_{VEGF}^{tis}$ and $k_{VEGF}^{prod}$ control VEGF availability, how fast VEGF diffuses and how fast it is produced respectively. A minor effect is also observed from change in $u^{thr}$, $m_{VEGF}^{thr}$ and $M_0$, which play an indirect role in edema formation. Because occluded capillaries don't actively leak though they may have leaked and resulted in FP in the past, rapid progression of capillary occlusion seems to decrease the amount of edema formation.

These parameter variation simulations provide more insight for some parameter selections by showing how a certain parameter at the cellular level would influence a model outcome at the tissue level. Such simulations support that the model can still produce plausible results with considerable variations of parameter values. This supports the validity of the model's fundamental structure, an adverse feedback mechanism governing retinal capillary occlusion and also means that as future experimental data for these parameters become available the model can be refined to improve morphological accuracy and provide greater quantitative predictive value for clinical applications.
Implementation of Simulations.

All simulations were executed using open-source software CompuCell3D

Results

Spatial Patterns of Disease Progression

It is important to maintain perspective regarding the model. While results in terms of an example run of the mode are initially presented here, CASE 1, as explained below, the model was run many times to explore the impact of the implemented stochastic events.

The configuration of cells and vessels has been initialized for a sector near the FAZ with dimensions of 510 μm×600 μm×50 μm, as determined from a patient ASOLO image. The sector during initialization is viewed in 3D with CAPs and MCs visualized (FIG. 17A). Completely initialized configuration shows that MCs and OTs are uniformly patterned between vessels from a 2D view (FIG. 17A). Under normal conditions, the blood flow is sourced from the arteriolar entrance, flows through the capillary network and exits via the venule. Because the model concentrates on a small arteriole-venule sector, side streams reflect capillaries connecting neighboring peri-foveal networks (FIG. 17B). Capillaries near the FAZ carried a relatively small blood flow, and therefore had a higher probability of occlusion based on the assumed occlusion mechanism. Cells near capillaries had abundant oxygen supply, while more distantly situated cells received less, but still sufficient, oxygen to support normal activities without ischemia (FIG. 17C). In the initial state VEGF production was assumed to be in the basal diabetic physiological range when retinal tissue was adequately oxygenated (FIG. 17D). This corresponds to a slight elevation of VEGF above the basal non-diabetic state; an elevation sufficient to induce the presence of a low level of ICAMs allowing diabetes induced leukostasis.

Once a first occlusion was initiated, the network topology changed reflecting the loss of that capillary and the steady state of oxygen tension and VEGF level were reestablished accordingly (FIGS. 18-20). Referring to FIG. 18A, the flow flow velocity map captures loss of a flow pathway due to capillary occlusion in week 0. As depicted in FIG. 18B, the second capillary spatially close to initial occlusion site became occluded in week 72. As depicted in FIG. 18C, several capillaries near FAZ and venule became occluded in week 124. As depicted in FIG. 18D, more than a quarter of the capillary network was obstructed by week 152. Color and the direction of arrows reflect the magnitude and orientation of velocities respectively. The redder the color is the greater the flow velocity. The unit for velocity is μm/s. "FAZ" in the figure refers to foveal avascular zone, "A" in red refers to arteriole, and "V" refers to venule.

Referring now to FIGS. 19A-19D, FIG. 19A depicts an oxygen tension map showing a localized hypoxic region near the occluded capillary in week 0. FIG. 19B depicts a hypoxic area of cells broadened to enclose a second occlusion site in week 72, but it's still restricted and confined spatially to the arteriole-venule sector. FIG. 19C depicts local insult by hypoxia propagated to break the terminal capillary near the venule and extended to the neighboring AV sector in week 124. FIG. 19D depicts a large area of hypoxia observed in week 152. Color reflects magnitude of oxygen tension. The redder the color the higher the oxygen tension is. The unit for oxygen tension is mmHg. "FAZ" in the figure refers to foveal avascular zone, "A" in red refers to arteriole, and "V" refers to venule.

Referring now to FIGS. 20A-20D, FIG. 20 depicts a VEGF level map showing localized synthesis of VEGF by Mueller cells in response to hypoxia in week 0. FIGS. 20B-20D depict an increasing number Mueller cells actively producing VEGF in weeks 72, 124, and 152, where the pattern of regions with high VEGF reproduced that of the area with low oxygen tension. Color reflects magnitude of VEGF level. The redder the color the higher the VEGF level is. VEGF level has arbitrary unit (A.U.). "FAZ" in the figure refers to foveal avascular zone, "A" in red refers to arteriole, and "V" refers to venule.

In week 0, a capillary was occluded (FIG. 18A) and consequently tissue surrounding it became poorly oxygenated (FIG. 19A). Within the model, the date of first capillary occlusion is always week 0. This is not the date of the initiation of diabetes. Certain Mueller cells become ischemic from this capillary occlusion and these hypoxic Mueller cells produce and release VEGF, which then develops local concentration peaks (FIG. 20A). Adjacent capillaries respond to the elevated concentration of VEGF, which increased their risk of occlusion via the ICAM mediated leukostasis mechanism not addressed separately in the model. Due to limited diffusion length of VEGF, distant capillaries are insensitive to such localized change. In week 72, secondary occlusions took place and the flow network became increasingly impaired (FIG. 18B). Consequentially, more Mueller cells had an insufficient oxygen supply and produced increased levels of VEGF (FIGS. 19B and 20B). At this point, the capillary damage appeared well bounded and confined in one arteriolar-venular sector. Notably, several cells in a neighboring area became hypoxic and produced elevated VEGF, possibly because their nearest vessel lost an important upstream branch, which carried significant oxygen supply before closure. However, there were still barriers composed of healthy cells and capillaries between the adjacent sectors. There then followed a series of capillary occlusions with minor enhancement in total volume inflow rate, until the damage in week 124 resulted in drop of inflow rate the first time since onset of initial injury.

Concomitant with the drop in total flow, the terminal venule between the two sectors was compromised (FIG. 18C, top of image) and a larger fraction of tissue was now hypoxic (FIG. 19C). In week 152, capillaries near the FAZ and the terminal venule were no longer patent (FIG. 18D), the FAZ is considerably enlarged, and roughly one third of the tissue was hypoxic and had an elevated VEGF environment (FIGS. 19D and 20D). It is noted that Sakata et al. (Ophthalmology. 2006; 113(8):1385-91). using a fluorescein angiography technique to measure perifoveal capillary blood velocity were able to show a significant negative correlation between capillary blood flow velocity and the size of the foveal avascular zone in diabetics without edema. In the present model, capillaries bordering the avascular zone show slowed flow, consistent with Sakata et al.

Edema Formation

Based on simple assumptions on the mechanism of edema formation (detailed in Edema Formation section in the Detailed Description of the Model section), the current model showed local retinal thickening (FIGS. 21A-21D). Referring to FIGS. 21A-21D, thickness of the retinal layer is represented by a color map at the end of year 0.5 (FIG. 21A), year 1 (FIG. 21A B), year 2 (FIG. 21A C) and year 3 (FIG. 21A D). Color represents the magnitude in Z axis. The bluer the color, the thicker a local retinal area is. Fluid appeared between year 1 and year 2, at the venous edge of the area of occlusion. The flow network is overlaid upon the color map to present patent flow paths at the time point of observation. Color bar only represents the thickness of tissue but not the flow velocities. "FAZ" in the figure refers to foveal avascular zone, "A" in red refers to arteriole, and "V" refers to venule.

A significant volume of fluid was observed 3 years post onset of initial capillary occlusion (FIG. 21D). Extravascular fluid was responsible for the increase in retinal thickness. Moreover, the spot where fluid was present correlated with the boundary of the ischemic region. The current study is limited to qualitative illustration of how retinal thickening can be caused by abnormal VEGF synthesis by Mueller cells. This is the canonical function of VEGF producing leakage from capillaries. In the model, edema is only a function of threshold VEGF levels and not a measure of local Starling-type relationships. It is reflective within the model of loci of active leakage at sites of intact, non-occluded capillaries which also have elevated VEGF above a particular threshold. Edema within the model is a prediction of expected locations of either retinal thickening or of retinal cystic structures as seen clinically on ocular coherence tomography. The model does not address the actual range of cysts since these can often be present in areas of retinal ischemia lacking active leakage by fluorescein angiography and thus can represent processes other than active leakage such as cellular necrosis or impaired retinal pigment epithelial pumping. The model does leave cysts present in areas in which capillaries had leaked but then subsequently become occluded similar to what occurs clinically.

Quantitative Global Measurement of Disease Progression

Figure 22A:
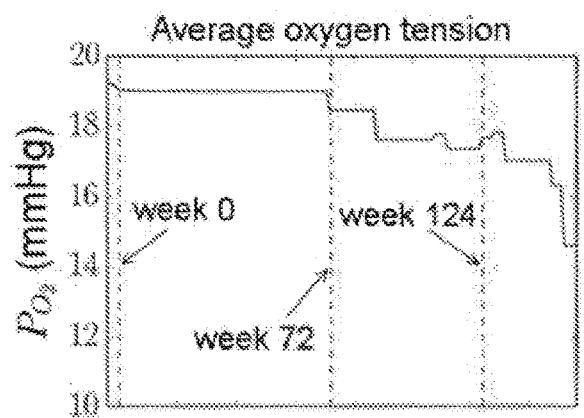
FIG. 22A depicts average oxygen tension over time for modeled CASE 1.
Figure 22B:
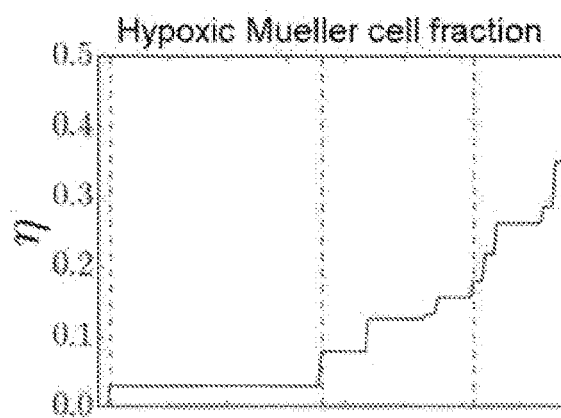
FIG. 22B depicts the growth of the hypoxic Mueller cell fraction over time for modeled CASE 1.
Figure 22C:
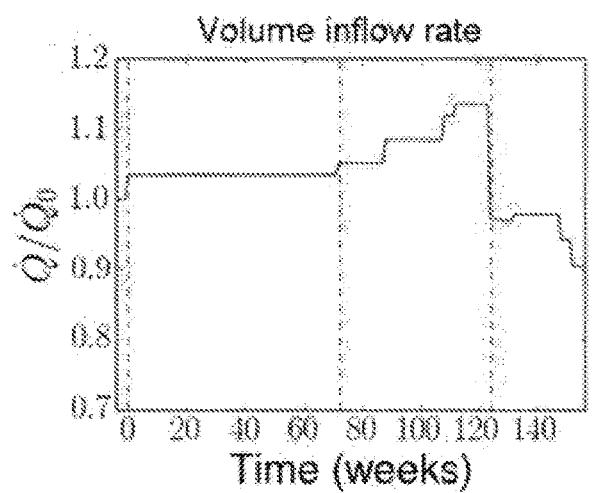
FIG. 22C depicts the total volume inflow rate over time for modeled CASE 1.
Figure 22D:
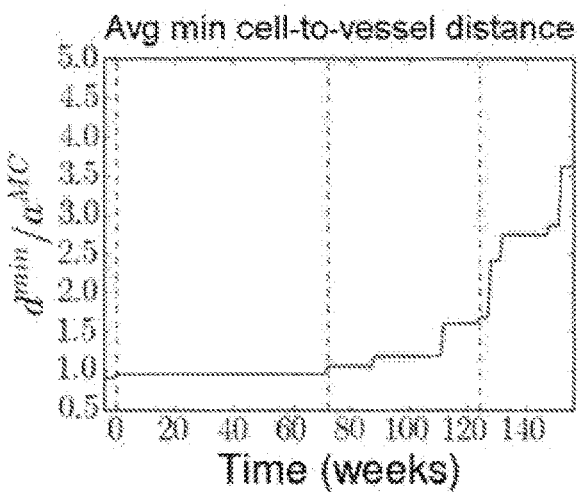
FIG. 22D depicts the average minimal cell-to-vessel distance over time for modeled CASE 1.

Following the onset of capillary closure, almost every additional occlusion caused average oxygen tension within cells to drop (FIG. 22A). The fraction of hypoxic Mueller cells went up nearly linearly from week 72 to week 152 (FIG. 22B). Distinct from the monotonic change in average oxygen tension and hypoxic fraction, the total volume inflow rate was non-monotonic, with continuous increases before a sharp decrease in week 124 and one more in week 152 (FIG. 22C). Early stages of increased inflow rate might be attributed to physiological response to loss of a selected group of blood flow pathways. Because oxygen tension is assumed to be constant within inlet capillary blocks, as would be physiologically expected, a higher volume inflow rate gives more oxygen carried into the system within a given period of time. This might suggest that at early stages of the disease with few capillary closures, the system would compensate for the oxygen insufficiency by increasing the blood flow. In contrast, at later stages of disease when many capillaries connecting the arteriole to the venule were occluded, total flow declined and occlusions seemed to occur more frequently. To better map the model to clinically observed symptoms, the present model used the scaled minimal cell-to-vessel distance $d^{min}/\alpha^{MC}$ as a metric to quantify disease progression spatially, where $\alpha^{MC}$ is the typical size of a Mueller cell (FIG. 22D). This is basically the number of Mueller cell diameters to a patent, or unoccluded, vessel. The $d^{min}/\alpha^{MC}$ increased monotonically with each additional capillary closure. Interestingly, the capillary occlusion that triggered a rapid drop of the total volume inflow at week 124 had a mild effect on $d^{min}/\alpha^{MC}$. This implied that topological location of a capillary segment was influential to the system blood flow supply, which might be neglected in a spatially-based metric.

Figure 23:
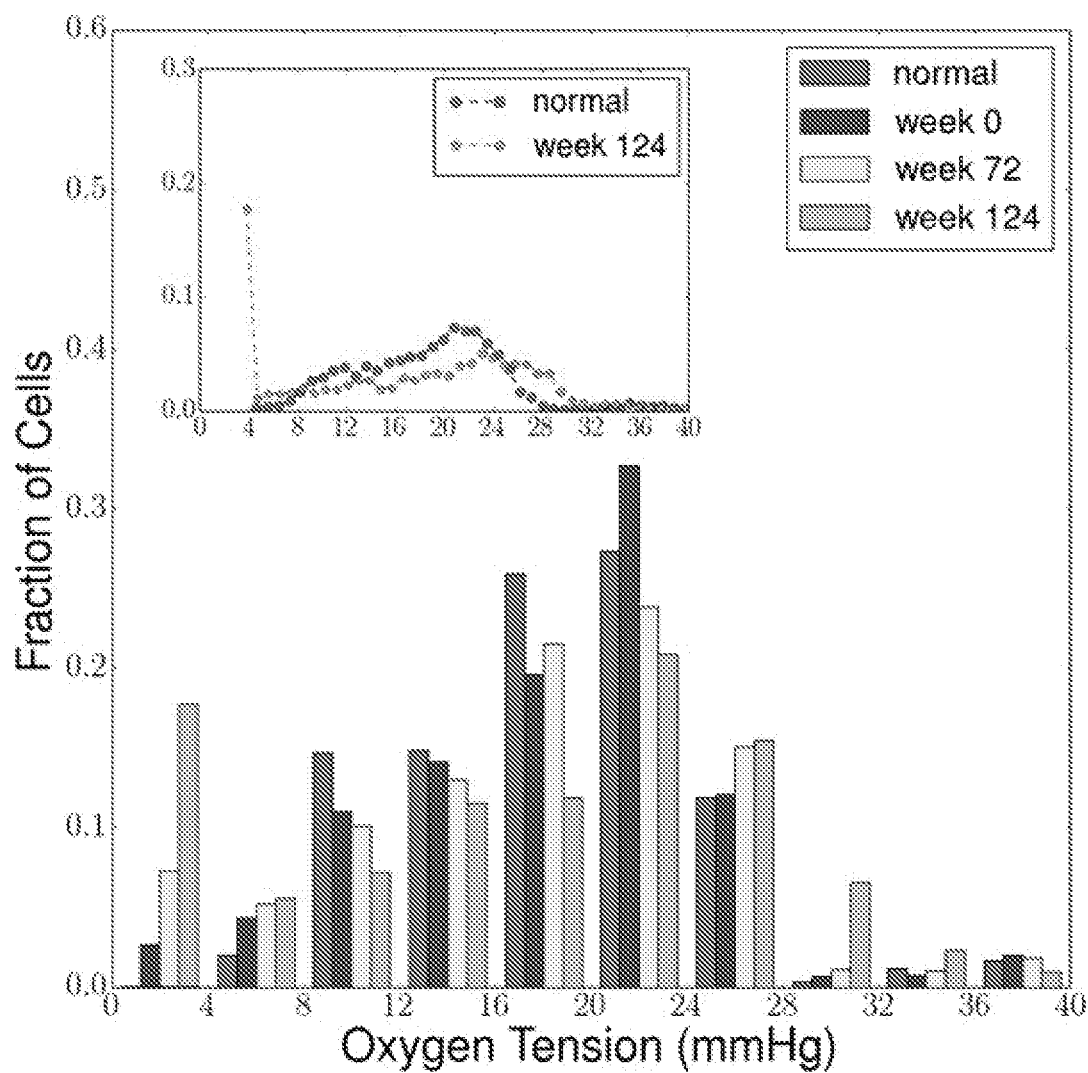
FIG. 23 depicts the cellular oxygen distribution over time for modeled CASE 1.

The distribution of oxygen tension within all cells exhibited an essentially unimodal shape under the normal condition where most cells had oxygen tensions of 10 to 25 mmHg, a small portion of cells located near vessels had higher levels ranging from 35 to 40 mmHg (FIG. 23) and no cells had an oxygen tension less than 4 mmHg $O_2$, i.e. no cells were ischemic. Capillary occlusions induced by elevation of VEGF gradually altered the distribution. An increasing number of cells turned hypoxic. The broad peak of cells at moderate levels of oxygen decreased and broadened with more cells both at lower oxygen levels and more cells from about 25-30 mmHg. This suggests that while the size of the hypoxic region in this tissue section was growing larger more cells were exposed to high oxygenation producing a bimodal oxygenation distribution.

This model's results are important both in terms of the images produced which bear a striking resemblance to those seen clinically and also as summarized in graphs showing changes occurring over time in a single run of the model for a specific initial capillary closure (FIGS. 18-23). The pattern of capillary loss near the FAZ with expansion over time is very similar to what is seen in diabetic patients. The pattern of mixed ischemia and edema in the perifoveal area is also that usually seen clinically. The curve in FIG. 22C is the most interesting in that flow rises from baseline levels for a period of time by as much as 13% and then declines. Clearly in end stage diabetic retinopathy with the entire capillary network occluded, the flow will go down. It is less clear that earlier stages in loss of the capillary network will result in increased total flow. This occurs because the model has some dilation of capillaries as a consequence of the adaptation module which would increase flows and also partially due to changes in network structure. The literature on blood flow in diabetes has been inconsistent due to measurements on diabetics at different stages of disease with a number of different technologies imaging flow in different locations (see Burgansky-Eliash et al., Retina. 2012; 32(1):112-9). The data from the Retinal Function Imager (RFI) measures flow velocities in small perifoveal vessels and seems most comparable to the vessel sizes in the model. This data is consistent with the model in that it shows an increased retinal blood flow velocity in diabetic patients without clinically seen morphological changes (Burgansky-Eliash et al., 2012). This would be similar to patients in the first year or two of the simulation (approximately 100 weeks).The percent increase in blood flow over controls was about 15% in (Burgansky-Eliash et al., 2012), quantitatively similar to the model's results. Physiologically this is possibly secondary to increased vasodilator mechanisms due to tissue hypoxia (Gardiner et al., Microcirculation. 2007; 14(1):25-38) and increased nitric oxide synthase (do Carmo et al., Gen Pharmacol. 1998; 30(3):319-24) and possibly network changes which could have occurred even though the patients did not have clinically visible changes. The model replicates this effect though it does not explicitly utilize any analogous mechanisms. This pattern of increased macular blood flow accompanied by edema (FIG. 21) is consistent with the regional distribution of diabetic lesions emphasized by (Skov et al., Graefes Arch Clin Exp Ophthalmol. 2011; 249(3):407-12). Burgansky-Eliash 2010 (Retina. 2010; 30(5):765-73) has RFI data on patients with non-proliferative diabetic retinopathy which show decreased blood flow at this stage of clinical retinopathy comparable to the blood flow decrease seen in the later weeks of this simulation. There is also clinical data on venous oxygen saturation in diabetes showing that venous oxygen saturation in diabetes is elevated over that seen in normal (Hammer et al., Graefes Arch Clin Exp Ophthalmol. 2009; 247(8):1025-30). This model did not specifically treat venous oxygen levels but as blood flows were rising with a constant input oxygen saturation occurring simultaneously with a rise in hypoxic retinal cells, retinal oxygen extraction must be lower resulting in elevated venous oxygen saturation. The oxygen map shows this qualitatively as an expanded reddish tissue area (top right corner near "V" FIG. 9C vs 9A) of elevated oxygen saturation around the venule. Hammer et al. interpret this elevation in venous oxygen levels to be due to a shortened arterio-venous passage time resulting in reduced oxygen extractio.

Figure 24A:
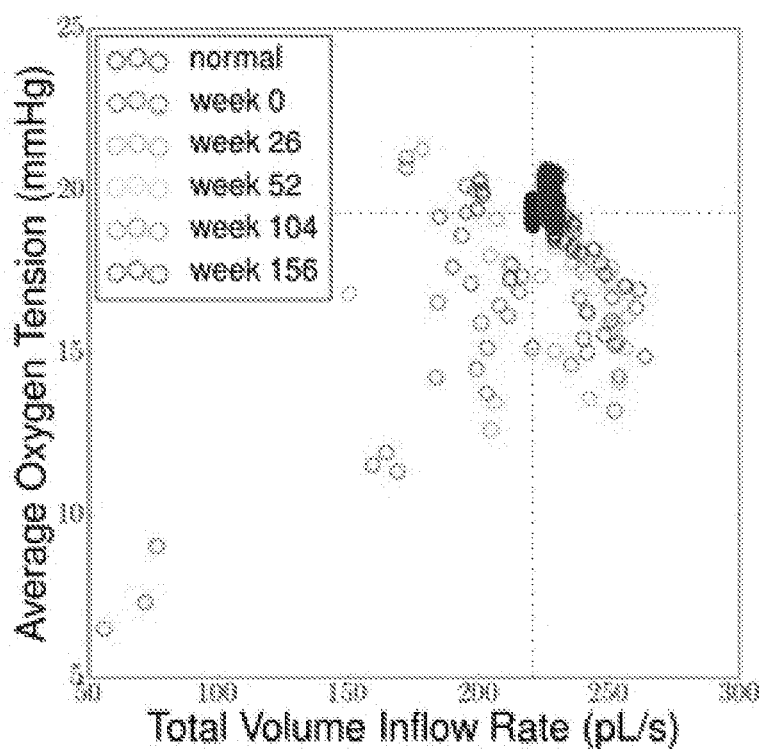
FIGS. 24A-24B depict flow-oxygen phase diagrams of 362 simulations for modeled CASE 1.
Figure 24B:
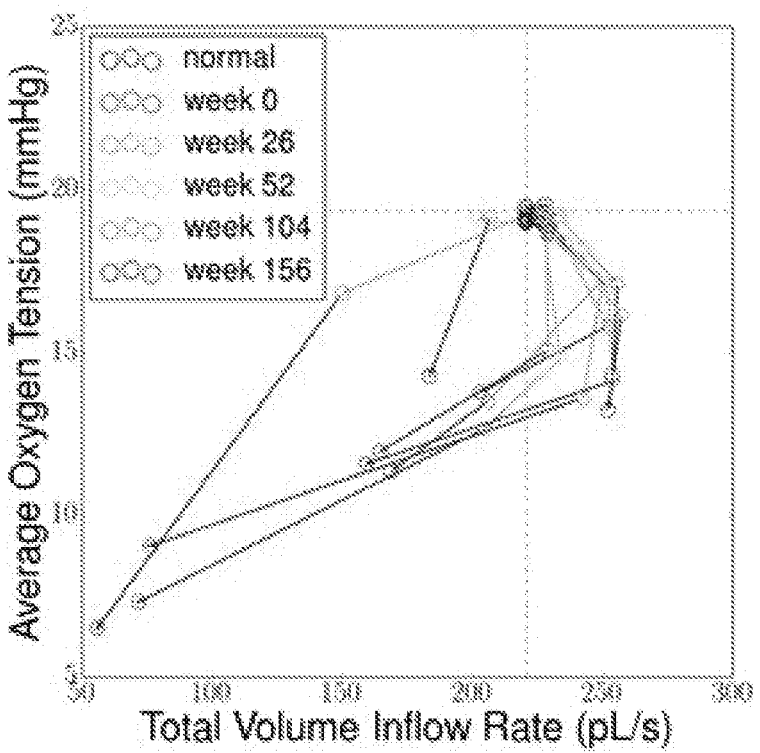

Replicate Simulations 362 replications of the macular capillary sector simulation were performed on a supercomputer to pursue the consequences of different initial occlusion sites and explored the evolution of progression states in a flow-oxygen phase diagram (FIGS. 24A-24B). The probabilistic aspect of the capillary occlusions means that repeated runs of the model will not produce identical patterns of capillary loss but similarity of replications will be strongly influenced by network structure. In the flow-oxygen phase diagram, the normal condition (circles in dark blue) were clustered in a confined range, which showed that all simulations had similar equilibrium oxygen tension and total inflow rates initially as expected (FIG. 24A). Circles gradually became scattered, because different simulations randomly picked different occlusion sites resulting in different disease progression trajectories. At 156 weeks, most simulations landed not far from the initial oxygen-flow states, which corresponded to situations without derived occlusions. On the contrary, some simulations showed distant end-point states situated mainly in low oxygen territory, which represented exacerbating progressive capillary occlusions. Of all such simulations, temporal trajectories were visualized (FIG. 24B) if the simulations showed less than 75% total inflow rate or oxygen tension in year three. Most such simulations followed a clockwise trajectory temporally, starting from equilibrium state, transiting via low-oxygen and high-flow zone and ending in the low-oxygen and low-flow territory of the phase diagram, which indicated a severely damaged end-point of the capillary network. The rest seemed to pursue a temporal pattern of evolution but still remained in a transition stage. These graphs show the results of typical runs of the model. This might illustrate a general picture of how retinopathy progresses in terms of system oxygenation and total blood supply. Note that clinically, many diabetics do not develop clinically significant retinopathy whereas a minority has significant propagation of capillary closure. This model would indicate that this variability of progression could have a significant element of probability, 'bad luck', in terms of which capillary was initially an occluded, in addition to other aspects of diabetic control and genetic/epigenetic factor.

Figure 25A:
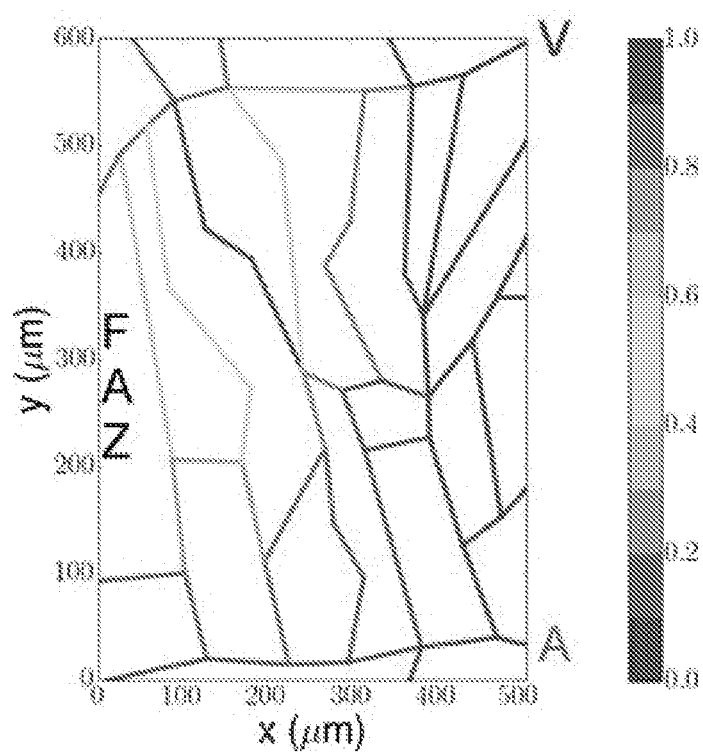
FIG. 25A depicts a patency map of the macular capillary network for modeled CASE 1 initial occlusion site. Color represents the frequency of a capillary segment being patent after 3 years of simulated time since the initial occlusion. Warmer color corresponds to less vulnerability to occlusion, or higher capillary patency.
Figure 25B:
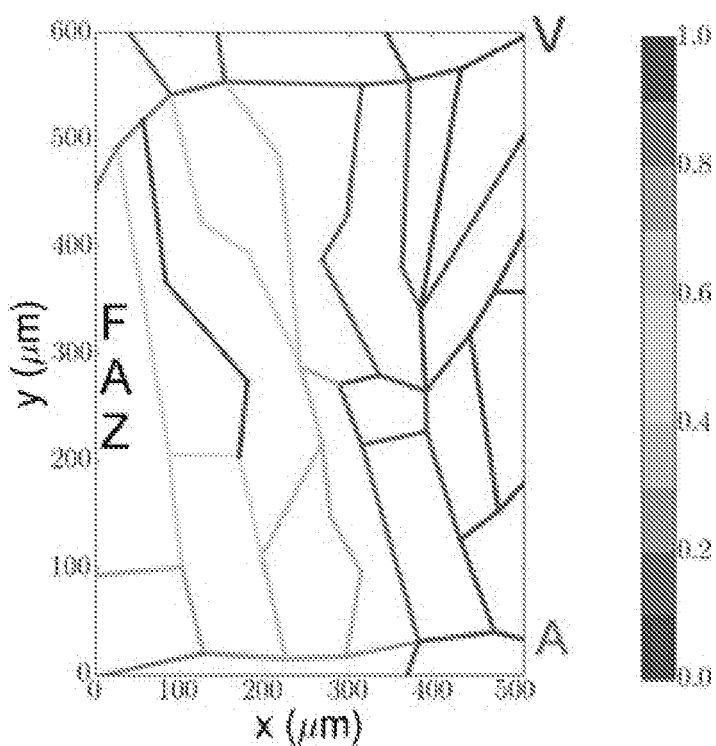
FIG. 25B depicts a patency map of the macular capillary network for modeled CASE 2 initial occlusion site. Color represents the frequency of a capillary segment being patent after 3 years of simulated time since the initial occlusion. Warmer color corresponds to less vulnerability to occlusion, or higher capillary patency.

The vulnerability of the capillary network given a certain initial occlusion site was further summarized (FIGS. 25A-25B). Among all capillary segments carrying relatively slow blood flow, initial occlusion of two capillaries near the FAZ seemed to be most influential in triggering derived occlusions, while occlusions of others had a less significant impact. Both cases showed a spatially relevant patency distribution, with capillaries closer to the initial occlusion site bearing a higher frequency of occlusion. Not uncommonly, capillaries near the terminal FAZ venule and arteriole were also candidates of occlusion. Closure of these capillaries was likely to propagate injury to neighboring foveal arteriolar-venular sectors. These runs show similar results and show that certain portions of this subject's capillary network are vulnerable to occlusion whereas others seem to be more resilient. Those more resilient areas tended to possess more densely situated capillaries and therefore the area of ischemia produced by a capillary occlusion is small and consequentially so is the resultant increase in local VEGF production and the probability of propagation. Occlusion or survival of a capillary is highly influenced by the local capillary network structure. This phenomenon seen in these results may be the result of more dense capillary networks further from the fovea where the visual impediment consequent to blood vessel opacity is less significant perhaps allowing more closely spaced capillaries. This pattern of loss of perifoveal capillaries, clinically called enlargement of the FAZ, is a commonly seen clinical pattern of macular ischemia development.

All methods disclosed and claimed herein can be executed without undue experimentation in light of the present disclosure. While the methods have been described in terms of embodiments, it is apparent to those of skill in the art that variations may be applied to the methods and in the steps or in the sequence of steps of the methods described herein without departing from the concept, spirit and scope herein. All modifications apparent to those skilled in the art are deemed to be within the spirit, scope and concept as defined by the appended claims.

What is claimed is:

1. A method for treating or preventing retinal vascular disease or preventing progression of retinal ischemia in a subject, the method comprising:
   identifying one or more areas of peripheral retina, macula, or both peripheral retina and macula predicted to cause progression of ischemia following occlusion of a capillary or capillary segment at or near the one or more areas; and
   applying one or more photocoagulation burns to the one or more areas of peripheral retina, macula, or both peripheral retina and macula predicted to cause progression of ischemia following occlusion of a capillary or capillary segment at or near the one or more areas.

2. The method according to claim 1, where the one or more areas of the macula predicted to cause progression of ischemia following occlusion of a capillary or capillary segment at or near the one or more areas are identified by modelling the subject's macular capillary anatomy, generating a risk map for each capillary or capillary segment, and selecting one or more capillaries or capillary segments predicted by the risk map for each capillary or capillary segment to cause progression of ischemia if occluded.

3. The method according to claim 2, wherein one or more capillaries or capillary segments are selected when a risk map for a capillary or capillary segment indicates a frequency of occlusion of surrounding capillaries of about 0.2 or greater following simulation.

4. The method according to claim 3, further comprising selecting one or more capillaries or capillary segments to be modelled by the method of claim 2 or claim 3, wherein the one or more capillaries or capillary segments are selected by determining a distance from each capillary or capillary segment of the subject's macular capillary anatomy to the next nearest capillary or capillary segment and selecting one or more capillaries or capillary segments for modelling having a distance to the next nearest capillary or capillary segment greater than about 140 microns.

5. The method according to claim 1, further comprising determining the subject's macular capillary anatomy.

6. The method according to claim 5, wherein the subject's macular capillary anatomy is determined by angiography, adaptive optics scanning laser ophthalmoscopy, or optical coherence tomography-angiography.

7. The method according to claim 1, wherein areas of the macula predicted to cause progression of ischemia following occlusion of a capillary or capillary segment at or near the one or more areas are identified by a computer system.

8. The method according to claim 1, wherein the one or more photocoagulation burns have a diameter of about 20 microns to about 100 microns.

9. The method according to claim 1, wherein the one or more photocoagulation burns have a diameter of about 50 microns.

10. The method according to claim 1, wherein the one or more photocoagulation burns are created by a laser.

11. The method according to claim 10, wherein creation of the one or more photocoagulation burns is computer guided.

12. The method according to claim 10, wherein creation of the one or more photocoagulation burns is automated.

13. A system comprising:
   a modelling computer system for identifying one or more areas of peripheral retina, macula, or both peripheral retina and macula predicted to cause progression of ischemia following occlusion of a capillary or capillary segment at or near the one or more areas, wherein the modelling computer system comprises a processor and one or more computer-readable media; and
   a photocoagulation laser system for applying one or more photocoagulation burns to the one or more areas of peripheral retina, macula, or both peripheral retina and macula, predicted by the processor and the one or more computer-readable media to cause progression of ischemia following occlusion of a capillary or capillary segment at or near the one or more areas.

14. The system of claim 13, wherein the one or more computer-readable media have computer executable instructions embodied thereon, wherein, when executed by the processor, the computer executable instructions cause the processor to identify the one or more areas of the peripheral retina, the macula, or both the peripheral retina and the macula predicted to cause progression of ischemia following occlusion of a capillary or capillary segment at or near the one or more areas.

15. The system of claim 13, wherein the modelling computer system is configured to receive an input of a subject's peripheral retinal capillary anatomy and/or function, macular capillary anatomy and/or function, or both peripheral retinal and macular capillary anatomy and/or function.

16. The system of claim 15, wherein the modelling computer system is configured to incorporate the subject's peripheral retinal capillary anatomy, macular capillary anatomy, or both peripheral retinal and macular capillary anatomy into a model for predicting progression of capillary occlusion.

17. The system of claim 16, wherein the modelling computer system is configured to run replicate simulations of the model.

18. The system according to claim 15, wherein the input of the subject's peripheral retinal capillary anatomy, macular capillary anatomy, or both peripheral retinal capillary and macular capillary anatomy is generated by angiography, adaptive optics scanning laser ophthalmoscopy, or optical coherence tomography-angiography.

19. The system of claim 13, wherein the modelling computer system is configured to model a subject's peripheral retinal capillary anatomy, macular capillary anatomy, or both peripheral retinal and macular capillary anatomy, generate a risk map for each capillary or capillary segment, and select one or more capillaries or capillary segments predicted by the risk map for each capillary or capillary segment to cause progression of ischemia if occluded.

20. The system of claim 19, wherein the modelling computer system is configured to select one or more capillaries or capillary segments when the risk map generated for a capillary or capillary segment indicates a frequency of occlusion of surrounding capillaries of about 0.2 or greater.

21. The system of claim 20, wherein the modelling computer system is configured to select one or more capillaries or capillary segments to be modelled, wherein the one or more capillaries or capillary segments are selected by determining a distance from each capillary or capillary segment of the subject's peripheral retinal capillary anatomy, macular capillary anatomy, or both peripheral retinal capillary and macular capillary anatomy to the next nearest capillary or capillary segment and selecting one or more capillaries or capillary segments for modelling having a distance to the next nearest capillary or capillary segment greater than about 140 microns.

22. The system according to claim 13, wherein the system further comprises an imaging system.

23. The system according to claim 22, wherein the imaging system is selected from the group consisting of an angiography system, AOSLO system and an OCT-A system.

24. The system according to claim 13, wherein the photocoagulation laser system is configured to apply one or more photocoagulation burns having a diameter of about 20 microns to about 100 microns to the one or more one or more areas of peripheral retina, macula, or both peripheral retina and macula.

25. The system according to claim 13 wherein the system comprises a subsystem, the subsystem comprising a dedicated Application Specific Integrated Circuit (ASIC) or a Field Programmable Gate Array (FPGA).

26. The system according to claim 13, wherein the modelling computer system comprises one or more subsystems implemented in whole or in part as software or firmware instructions defining the operation of the one or more subsystems.

27. The system according to claim 13, wherein the photocoagulation laser system is configured to apply the one or more photocoagulation burns in a computer guided manner or an automated manner.

28. A method performed on a computer system that automatically predicts one or more areas of peripheral retina, macula, or both peripheral retina and macula of a subject likely to cause progression of ischemia following occlusion of a capillary or capillary segment at or near the one or more areas, the method comprising:
   inputting a capillary network of the peripheral retina, macula, or both peripheral retina and macula of the subject;
   modelling the capillary network of the peripheral retina, macula, or both peripheral retina and macula;
   generating a risk map for each capillary or capillary segment of the capillary network of the peripheral retina, macula, or both peripheral retina and macula; and
   predicting, based on the risk map, one or more capillaries or capillary segments that are likely to cause progression of ischemia if occluded.

29. The method of claim 28, wherein modelling the capillary network of the peripheral retina, macula, or both peripheral retina and macula comprises:

a) predicting blood flow directions and rates through the capillary network of the peripheral retina, macula, or both peripheral retina and macula;
b) simulating oxygen fluxes within and/or near the capillary network of the peripheral retina, macula, or both peripheral retina and macula;
c) simulating VEGF fluxes within and/or near the capillary network of the peripheral retina, macula, or both peripheral retina and macula;
d) predicting a probability of occlusion of a capillary or capillary segment of the capillary network of the peripheral retina, macula, or both peripheral retina and macula; and
e) repeating steps a)-d).

30. The method of claim 29, wherein predicting the probability of occlusion of the capillary or capillary segment of the capillary network of the peripheral retina, macula, or both peripheral retina and macula comprises determining whether local VEGF levels at or near the capillary or capillary segment exceed a pre-defined VEGF threshold and blood flow velocity is below a pre-defined velocity threshold, wherein when VEGF levels exceed the pre-defined VEGF threshold, and blood flow velocity is below the pre-defined velocity threshold, the capillary or capillary segment is predicted to be occluded.

31. The method of claim 29, wherein the modelling continues until all capillaries or capillary segments of the capillary network of the peripheral retina, macula, or both peripheral retina and macula are occluded, or if no occlusion occurs, until a new occlusion occurs or until modelling ceases.

32. The method of claim 29, wherein generating the risk map for each capillary or capillary segment of the capillary network of the peripheral retina, macula, or both peripheral retina and macula comprises compiling the probabilities of occlusion for each capillary or capillary segment of the capillary network of the peripheral retina, macula, or both peripheral retina and macula from iterative modelling simulations.

33. The method of claim 32, wherein one or more capillaries or capillary segments are selected when determined to have a probability of occlusion of about 0.2 or greater.

34. The method of claim 28, further comprising selecting capillaries or capillary segments to be modelled, wherein the one or more capillaries or capillary segments are selected to be modelled by determining a distance from each capillary or capillary segment of the subject's peripheral retinal capillary anatomy, macular capillary anatomy, or both peripheral retinal capillary and macular capillary anatomy to the next nearest capillary or capillary segment and selecting one or more capillaries or capillary segments for modelling having a distance to the next nearest capillary or capillary segment greater than about 140 microns.

35. One or more computer-readable media having computer-executable instructions thereon for performing the method of claim 28, wherein, when executed by a processor, the computer-executable instructions cause the processor to perform the method.

* * * * *